(12) United States Patent
Frankard et al.

(10) Patent No.: US 7,807,872 B2
(45) Date of Patent: Oct. 5, 2010

(54) DOWN REGULATION OF PLANT CYCLIN-DEPENDENT KINASE INHIBITORS

(75) Inventors: Valérie Marie-Noëlle S. Frankard, Brussels (BE); Adrian Marius Peres Bota, Brakel (BE); Anne-Marie Droual, Lille (FR); Vladimir Mironov, Ghent (BE); Dirk Inze, Moorsel-Aalst (BE); Yves Hatzfeld, Lille (FR)

(73) Assignee: CropDesign N.V., Zwijnaarde-Gent (BE)

( * ) Notice: Subject to any disclaimer, the term of this patent is extended or adjusted under 35 U.S.C. 154(b) by 867 days.

(21) Appl. No.: 10/333,006

(22) PCT Filed: Jun. 29, 2001

(86) PCT No.: PCT/IB01/01492

§ 371 (c)(1),
(2), (4) Date: Jan. 14, 2003

(87) PCT Pub. No.: WO02/28893

PCT Pub. Date: Apr. 11, 2002

(65) Prior Publication Data

US 2004/0019926 A1     Jan. 29, 2004

Related U.S. Application Data

(60) Provisional application No. 60/218,471, filed on Jul. 14, 2000, provisional application No. 60/241,219, filed on Oct. 13, 2000.

(51) Int. Cl.
*C12N 15/82* (2006.01)
(52) U.S. Cl. ...................................................... 800/286
(58) Field of Classification Search ................... 800/286
See application file for complete search history.

(56) References Cited

U.S. PATENT DOCUMENTS

| 5,750,862 | A | * | 5/1998 | John ........................... 800/320 |
| 6,465,718 | B1 | * | 10/2002 | Inze et al. .................... 800/290 |

FOREIGN PATENT DOCUMENTS

| WO | WO 98/41642 | | 9/1998 |
| WO | WO 99/13083 | | 3/1999 |
| WO | WO 99 14331 | * | 3/1999 |
| WO | WO 99/14331 | * | 3/1999 |
| WO | WO 99/64599 | | 12/1999 |
| WO | WO 99/66055 | | 12/1999 |
| WO | WO 00/60087 | | 10/2000 |
| WO | WO 00/69883 | | 11/2000 |
| WO | WO 01/20020 | | 3/2001 |

OTHER PUBLICATIONS

Wang H. et al. ICK1, a cyclin-dependent protein kinase inhibitor from *Arabidopsis thaliana* interacts with both Cdc2a and CycD3, and its expression is induced by abscisic acid. Plant J. Aug. 1998;15(4):501-10.*
Sandler S.J. et al. Inhibition of gene expression in transformed plants by antisense RNA. Plant Molecular Biology, 1988, vol. 11, No. 3, pp. 301-310.*
van der Krol A.R et al. Inhibition of flower pigmentation by antisense CHS genes: promoter and minimal sequence requirements for the antisense effect. Plant Mol Biol. Apr. 1990;14(4):457-66.*
Waterhouse et al. Virus resistance and gene silencing: killing the messenger. Trends Plant Sci. Nov. 1999;4(11):452-457.*
Wang H. et al. The emerging importance of cyclin-dependent kinase inhibitors in the regulation of the plant cell cycle and related processes, Canadian Journal of Botany, vol. 84, No. 4, Apr. 1, 2006 , pp. 640-650.*
Allona et al. (1998) "266 Loblolly pine C Pinus taeda cDNA clone IC4A, mRNA sequence" *EMBL* Accession No. AA556411.
Buell et al. (2000) "Oryza sativa chromosome 10 BAC OSJNBb0094K03 genomic sequence, complete sequence" *EMBL* Accession No. AC069145.
Casale et al. (1999) "MAP kinase activation by hypoosmotic stress of tobacco cell suspensions: towards the oxidative burst response?", *The Plant Journal*, 19(3):297-307.
Cho et al. (1999) "Cell cycle control study in plant: control of plant growth by G1 specific cyclin D1 and a novel D1 and D3 specific cyclin dependent kinase inhibitor, p23ack1", *Molecular Biology of the Cell*, 10:432a.
de Almeida, et al. (1999) "Molecular markers and cell cycle inhibitors show the importance of cell cycle progression in nematode-induced galls and syncytia", *Plant Cell*, 11:793-808.
den Boer et al. (2000) "Triggering the cell cycle in plants" *Trends Cell Biol.*, 10:245-250.
Fountain et al. (1997) "Chenopodium rubrum G1 cyclin-dependent kinase inhibitor mRNA. complete cds" *EMBL* Accession No. AJ002173.
Karimi et al. (1999) "ARMI: Application for engineered resistance to plant-parasitic nematodes" *Med. Fac. Landbouww. Univ. Gent*, 64:439-442.
Kovtun et al. (2000) "Functional analysis of oxidative stress-activated mitogen-activiated protein kinase cascade in plants", *PNAS* 97(6):2940-2945.
Lui et al. (2000) "The *Arabidopsis* Cdc2a-interacting protein ICK2 is structurally related to ICK1 and is a potent inhibitor of cyclin-dependent kinase activity in vitro" *The Plant Journal*, 21(4):379-385.
Planchais et al. (1997) "Roscovitine, a novel cyclin-dependent kinase inhibitor, characterizes restriction point and G2/M transition in tobacco BY-2 cell suspension" *The Plant Journal*, 12(1):191-202.
Schultz et al. (1997) "Characterisation and expression of a rice RAD23 gene" *Plant Mol. Biol.*, 34:557-562.
Vereecke et al. (2000) "The *Rhodococcus fascians*-plant interaction: morphological traits and biotechnological applications", *Planta*, 210:241-251.
Walbot et al. (2000) "82900IE06.x1 829—Silk infected with Fusarium Zea mays cDNA, MRNA sequence", *EMBL* Accession No. AW267370.
Wang et al. (1997) "A plant cyclin-dependent kinase inhibitor gene" *Nature*, 386:451-452.
Wang et al. (1997) *Arabidopsis thaliana* cyclin-dependent kinase inhibitor protein (ICK1) mRNA, complete cds. *EMBL*, Accession No. U94772.
Wang et al. (1998) "ICK1, a cyclin-dependent protein kinase inhibitor from *Arabidopsis thaliana* interacts with both Cdc2a and CycD3, and its expression is induced by abscisic acid", *The Plant Journal*, 15(4):501-510.
Wang et al. (2000) "Expression of the plant cyclin-dependent kinase inhibitor ICK1 affects cell division, plant growth and morphology", *The Plant Journal*, 24(5):613-623.

* cited by examiner

*Primary Examiner*—Cynthia Collins
(74) *Attorney, Agent, or Firm*—Ann R. Pokalsky, Esq.; Dilworth & Barrese, LLP

(57) ABSTRACT

The present invention provides isolated nucleic acid molecules encoding plant cyclin dependent kinase inhibitors (ICKs). The nucleic acid molecules may be used to down-regulate expression of a plant ICK, thereby providing useful plant phenotypes.

6 Claims, 24 Drawing Sheets

```
   1    GGCACGAGGC GGCGCAG(ATGGGCAAGTACA TGAGGAAGTT CAGGGGGGCC
  51    ACGGGGGAGG AGTTGGCCGC CATGGAGGTC ACGCAGGTGG TTGGCGTCCG
 101    GACGAGGTCG AGGTCGGCAG CGGCGGCGGG CGCGACGACG ACGAAGGTGC
 151    AGGCGGCGTC GGCGGCGTCC ACCAGGAGGA GGAAGGCGCT GCTGCCGACG
 201    GCGGTCGTGG GGACTACTCG CCGTGACGGC GGGAGCTGCT ACCTCCAGCT
 251    GAGGAGCCGC ATGCTGTTCA TGGCCCCGCC GAGGCCGGCG CCGGCCGCGA
 301    GGGCTCCGGT TGTAGCGGAG GCGGCGGGTT CCGGGAACGG AGCGGCGGCG
 351    CATGCGGCGG CTGGCCTCTC GCGTTGCTCC AGCACGGCGT CGTCCGTGGA
 401    CGCGGCGGCT CAGGACAGGA GCCTCGCGTG CCGCTCCGAC GTCGCGGAGG
 451    CAGGCAGCGA GCATGTCCCG GAGGGCTCCG CGAGCGACTC GGCGAGCGGC
 501    CGTGACCGCG AGAGGAGAGA AACAACTCCA TCAAGCTTTC TCCCCGGCGA
 551    GGTGAGCGAT CTGGAGTCGG ATCTGGCTGG AGGACAGAAG CGCAGCCGTC
 601    CACTACCTTC TGCGGCAACA GCCTCAGCAC AGCAAGCCAC GCGGCCGAAG
 651    ATTCCGCCGG CCGCCGAGAT CGAGGCGTTC TTCGCGGCGG CCGAGGAGGC
 701    TGAGGCCAAG CGCTTCGCCG CCAAGTACAA CTTCGACGTC GTTCGCGGCG
 751    TGCCCCTCGA CGCCGGTCGG TTCGAGTGGA CTCCGGTGGT CAGCAGCCGA
 801    AGCTGA)AGCGAGCGTGCAGA TTAAGCGGAA GCTAGAAAGG AAGGTACAGG
 851    GGGGCGCCGT GTAGAAAGGG AAGGCGAGCT AGAGAGAGGA GAAGAAGAAG
 901    AAAAGATGCT CATCCAAAGG GAATAAACGG GAAAAGTGGG AGACTACAAA
 951    AAAAGAAGCA TTATAGCCTA ACAACCACCG ATTCGACTCT TTTTTCTTTC
1001    ACATTTTCTT TGCATTTTTA CTCTTACTGT GTACTAGAAA GTAGTAGCAG
1051    TAGTAAACTA GTAATTCGTC CCAGTATTTA TCAGAGGTTT ATCTCGATAG
1101    GAATAGATAT ATTATCCCCT[TACTGTAATT GCCTCCATCT TGTATTTGGA
1151    TGGAAATTAA ATTTACTGTA CAGCAGCAGC AGCTGTTCTG CAAGTTTAAG
1201    TTAACCATCA CCGTTTTATT ACTT]AAAAAAAAAAAAAAA AA
```

FIGURE 1

```
  1  GAAACCCTAG CCCCCTCCCA TCCCGAGTCC CGACCGCC(ATGGGCAAGTAC
 51  ATGCGCAAGG CCAAGGTGGT GGTCTCCGGC GAGGTGGTGG CCGCCGCCGT
101  CATGGAGCTC GCCGCGGCGC CGCTCGGGGT GCGCACCCGC GCCCGCTCCC
151  TCGCGCTGCA GAAGAGGCAG GGCGGGGAGT ACCTCGAGCT CAGGAGCCGC
201  AGGCTCGAGA AGCTCCCTCC TCCCCCGCCG CCGCCGCCGA GGAGGAGGGC
251  GACGGCTGCG GCTGCGACTG CTGATGCGAC GGCGACGGAG AGCGCGGAGG
301  CGGAGGTGTC GTTCGGGGGG GAGAACGTCC TCGAGCTGGA GGCCATGGAA
351  AGGAATACCA GGGAGACGAC ACCTTGCAGC TTGATCAGGG ACCCCGATAC
401  GATTAGCACC CCTGGATCTA CCACAAGGCG CAGCCACTCG AGTTCTCATT
451  GCAAGGTGCA AACACCCGTG CGCCACAACA TTATTCCAGC ATCAGCAGAG
501  CTGGAAGCGT TCTTCGCYGC CGAAGAGCAA CGGCAACGAC AGGCTTTCAT
551  CGACAAGTAT AACTTTGATC CTGTGAATGA CTGCCCTCTT CCCGGCCGRT
601  TTGAATGGGT CAAGCTAGAC TGA)TAGATTTTCAGGAAAAG AAGGGCACCA
651  TGGACCTCTC TGCTCCCTCC ACAGTAGTAG CGTGGCAGAG GCGCTTACCG
701  TCAAGTTAGC TTTGATCCTG TTGTAAAAAT TTAGGGTTAG CCTGTAGACT
751  CAATGGTCAA TGTGAACATA CAGAACTGAT GCTGAGTTAC AACCCTAATC
801  CCTCAACTAC AATGTAACCC TTAACAGCTC ATTCTGTAAG GAACCACCTC
851  CTCCTCTAGG GCCTAGCTAG CCTTATCATC TGTTATTACC AGTTGCTGGA
901  TTAATGAAGT TAGATCTAGA TATTGTGTCA CAGTTTAACC TGTTGTGTGT
951  GTGGTGGTAG CATTGGCATT GGCAATGGGG TATGGCAGTG TGTGTGTGGT
1001 GCTGCACTGC ACCTCCCGAA GTGCTGTAAT TTTTGTCTAT ACTTCTGCTA
1051 AAAAAAAAAA AAAAAA
```

FIGURE 2

```
                    1                                       40
ALFALFA ICK   (1)   MGKYMKKLKSKSESPSPNSTPTPSPSPSPTPITTNSPPPT
AtICK1        (1)   MVRKYRKAKGIVEAGVSS---------------TYMQL
AtICK2        (1)   MAAVRRRERDVVEENGVTTTTVK----------RRK
AtICK3        (1)   MGKYMKSKITGDISVME---------------VSKA
AtICK4        (1)   MGKYIRKSKIDGAGAGAGGGGGGGGGESSIALMDVVSPS
AtICK5        (1)   MGKYIKKSKVAGAVSVKD--------------KSH
AtICK6        (1)   MSERKRELAEEASSTSFSP-------------LKKTK
AtICK7        (1)   ----MSETKPKRDSEYEGS-------------NIKRMR
CHENOPOD ICK  (1)   MAAAATPTSSPAKKIKKVS--------------KSS
OsICK2        (1)   MGKYMRKFRGATGEELAAMEVTQVVGVRTR------SRSA
OsICK4        (1)   MGKYMRKAKVVVSGEVVA---A------------AVMEL
OsICK5        (1)   MGKKKKRDGAAARRQARVVVGG-------------VRTR 41                                      80
ALFALFA ICK   (41)  TPNSSDGVRTRARTLALENSNN-----------------
AtICK1        (24)  RSRRIVYVRSEKSSSVSVVGDN-----------------
AtICK2        (27)  MEEEVDLVESRIILSPCVQATN-----------------
AtICK3        (23)  TA-PSPGVRTRAAKTLALKRLN-----------------
AtICK4        (41)  SS-SSLGVLTRAKSLALQQQQQRCLLQKPSSPSSLPPTSA
AtICK5        (22)  P--PALGFRTRAAAAKNLALHR-----------------
AtICK6        (25)  LNDSSDSSPDSHDVIVFAVSSS-----------------
AtICK7        (22)  LDDDDDVLRSPTRTLSSSSSSS-----------------
CHENOPOD ICK  (23)  YN--IPQLRSRRKNLSAP--EN-----------------
OsICK2        (35)  AAAGATTTKVQAASAASTRRRK-----------------
OsICK4        (25)  AA-APLGVRTRARSLALQKRQG-----------------
OsICK5        (27)  AAVTARRVVASAEEGCGLVGRG-----------------

81                                     120
ALFALFA ICK   (63)  ----------QNQNLSVSSDSYLQLRNRRLKR------P
AtICK1        (46)  ------------------GVSSSCSGSNEYKK----KEL
AtICK2        (49)  -------------RGGIVARNSAGASETSVVIVRRRDSPP
AtICK3        (44)  --------SSAADSALPNDSSCYLQLRSRRLEKPSSLIEP
AtICK4        (80)  SPNPPSKQKMKKKQQQMNDCGSYLQLRSRRLQK----KPP
AtICK5        (42)  ---------LRSHSDEADSFNYLQLRSRRLVK----LPL
AtICK6        (47)  ------------------SVASSAALASDECSVTIG-GEE
AtICK7        (44)  ---------------LAYSVSDSGGFCSVALSE----EED
CHENOPOD ICK  (41)  --------------------EAELETTPLEVAAVVEEE
OsICK2        (57)  ----ALLPTAVVGTTRRDGGSCYLQLRSRMLFMAPPRPAP
OsICK4        (46)  ------------------GEYLELRSRRLEK----LPP
OsICK5        (49)  --------GGGGSGGDDGEGGCYLRLRSRRLPFVAAVVS
```

FIGURE 3

```
                       121                                      160
ALFALFA ICK   (86)  LIRQHSAKRNKGHDGNPKS------PIGDSIAEEKTVQK
     AtICK1   (63)  IHLEEEDKDG---------------DTETSTYRRGTKRK
     AtICK2   (76)  VEEQCQIEEEDS-------------SVSCCSTSEEKSKR
     AtICK3   (76)  KQPPRVHRSGIKESGSRSRVDSVNSVPVAQSSNEDECFDN
     AtICK4  (116)  IVVIRSTKRRKQQRRNETCGRNPNPRSNLDSIRGDGSRSD
     AtICK5   (68)  LTNTRKQQKQ---------------QLIPSVNQCQTK--
     AtICK6   (68)  SDQSSSISSGCFTS-E---------SKEIAKNSSSFGVD
     AtICK7   (65)  DHLSSSISSGCS-------------SSETNEIATRLP
CHENOPOD ICK  (59)  EVANCSSSEVITTARSDFP------PSCCSSNYDQLS--
      OsICK2  (93)  AARAPVVAEAAGSGNG---------AAAHAAAGLSRCSST
      OsICK4  (62)  PPPPPPR-RR---------------ATAAAATADATATE
      OsICK5  (81)  SRREEALGDSVAEAAS----------SSSSRAVELLGC 161                                      200
ALFALFA ICK  (119)  SPEPENAEFKEN---------------------AED-TE
     AtICK1   (87)  LFENLREEEKEE----------------------LSKSM
     AtICK2  (102)  RIEFVDLEENNG----------------------DDR
     AtICK3  (116)  FVSVQVSCGENS----------------------LGFESR
     AtICK4  (156)  SVSESVVFGKDKDLISEINKDPTFGQNFFDLEEEHTQSFN
     AtICK5   (90)  --NPRASSGPAK----------------------K---LE
     AtICK6   (97)  LEDHQIETETET----------------------S-TFIT
     AtICK7   (89)  FSDLEAHEISET----------------------EISTLLT
CHENOPOD ICK  (90)  SSEPEVVKDDDG----------------------LGNRTA
      OsICK2 (124)  ASSVDAAAQDRSLACRSDVAEAGSEHVPEGSASDSASGRD
      OsICK4  (85)  SAEAEVSFGGEN----------------------VLELEAME
      OsICK5 (109)  SGEEEAMAEKXS----------------------ATTPSS 201                                      240
ALFALFA ICK  (136)  RSARETTPVHLIM-RADVLRPPRPITRRTFPTEAN-----
     AtICK1  (104)  ENYSSEFESAVKE-SLDCCCSGRKTMEETVTAEEE-----
     AtICK2  (117)  ETETSWIYDDLNK-SEESMNMDSSSVAVEDVESRR-----
     AtICK3  (134)  HSTRESTPCNFVE-DMEIMVTPGSSTRSMCRAT----KE
     AtICK4  (196)  RTTRESTPCSLIR-RPEIMTTPGSSTKLNICVSESNQRED
     AtICK5  (103)  PDTTTEEACGDNE-RISRSDCNFGDKGFDLESE-------
     AtICK6  (114)  SNFRKETSPVSEG-LGETTTEMESSSATKRKQP-------
     AtICK7  (108)  NNFRKQGISSSEN-LGETAEMDSATTEMRDQRKTE-----
CHENOPOD ICK (108)  DPEVESGEASSKQ-KESHRTEAREATKLDDQDYP-----A
      OsICK2 (164)  RERRETTPSSFLPGEVSDLESDLAGGQKRSRPLPSAATAS
      OsICK4 (105)  RNTRETTPCSLIR-DPDTTSTPGSTRRSHSSS---HCKV
      OsICK5 (127)  RRPPGDADSSDAESNQEAKQQMCRRSSTTSAAAFHAGATT
```

FIGURE 3 (cont'd)

```
                      241                                       280
ALFALFA ICK  (170)  PKTEQP-TIPISREFEEFCAKHEAEQQRE---FMEKYNFD
    AtICK1   (138)  EKAKLMTEMPTESEIEDFFVEAEKQLKEK---FKKKYNFD
    AtICK2   (151)  RLRKSLHETVKEAELEDFFQVAEKDLRNKLLECSMKYNFD
    AtICK3   (168)  YTREQDNVIPTTSEMEEFFAYAEQQQQRL---FMEKYNFD
    AtICK4   (235)  SLSRSHRRRPTTPEMDEFFSGAEEEQQKQ---FIEKYNFD
    AtICK5   (135)  NRSMISDSKSIQSEIEDFFASAEQQQQRF---FIQKYNFD
    AtICK6   (146)  ----GVRKTPTAAEIEDLFSELESQDDKKK-QFIEKYNFD
    AtICK7   (142)  -KKKKMEKSPTQAELDDFFSAAERYEQKR---FTEKYNYD
CHENOPOD ICK (142)  TKSTVQIKMPSDSEIEEFFAVAEKDLQKR---FSEKYNFD
    OsICK2   (204)  AQQATRPKIPPAAEIEAFFAAAEEAEAKR---FAAKYNFD
    OsICK4   (141)  QTPVRHNIIPASAELEAFFAAEEQRQRQA---FIDKYNFD
    OsICK5   (167)  RSFRMMAPPAAAAEIEEFLAAAERSEAER---FAAKYNFD 281                   305
ALFALFA ICK  (206)  PVTEQPLPG----RYETEKVSP---
    AtICK1   (175)  FEKEKPLEG----RYEWVKLE----
    AtICK2   (191)  FEKDEPLGGG---RYEWVKLNP---
    AtICK3   (205)  IVNDIPLSG----RYEWVQVKP---
    AtICK4   (272)  PVNEQPLPG----REEWTKVDD---
    AtICK5   (172)  IVSDNPLPG----RYEWVKVMP---
    AtICK6   (181)  IVNDEPLEG----RYKWDRL-----
    AtICK7   (178)  IVNDTPLEG----RYQWVSLKP---
CHENOPOD ICK (179)  IVKDVPLKG----RYDWVPTNP---
    OsICK2   (241)  VVRGVPLDAG---REEWTPVVSSRS
    OsICK4   (178)  PVNDCPLPG----REEWVKLD----
    OsICK5   (204)  VVRGVPLDAGGAGREEWTAVGSG--
```

FIGURE 3 (cont'd)

```
       OsICK2 (121) SSTASSVDAAAQDRSLACRSDVAEAGSEHVPEGS-ASDSA
OsICK3 partial   (1) ------------------------------LITLSVC
       OsICK4  (61) PPPPPPPRRRATAAAATADATATESAEAEVSFGGENVLEL
       OsICK5  (73) FVAAAVVSSRREEALGDSVAEAASSSSSRAVELLGCSGEE
        PtICK   (1) ----------------------------------------
 SbICK partial   (1) -------------------------------VFNAFKSCLY
ZmICK1 partial   (1) ----------------------GYGDHVPDVVXASNSG
ZmICK2 partial   (1) --------------------------------------ES OsICK2 (160) SGRDRERRETTPSS--FLPGEVSDLESDLAGGQKRSRPLP
OsICK3 partial   (8) HTLTLTLINSCFYSLQFRKSLKPNSCSREVAAEHAGEHKH
       OsICK4 (101) EAMERNTRETTPCSLIRDPDTISTPGSTTRRSHSS---SH
       OsICK5 (113) EAMAEKXSATTPSSRRPPGDADSSDAESNQEAKQQMCRRS
        PtICK   (1) ----------------------------------------
 SbICK partial  (11) IYIYKQTKDAPDDRRRLRRGRGESEGETREREPLQ---GP
ZmICK1 partial  (17) SVPDRERRETTPSSSRAHGGELSDLESDLVGRQK---TGC
ZmICK2 partial   (3) EAMGRNTRETTPCSLINS-EMISTPGSTTRSSHSS---HR OsICK2 (198) SAATASAQQA--------TRPKIPPAAEIEAFFAAAEEAE
OsICK3 partial  (48) NPAAAAAAGR--------RPPLSPPEAEIEAFFAAAELAE
       OsICK4 (138) CKVQTPVRHN--------I---IPASAELEAFFAAAEEQRQ
       OsICK5 (153) STTSAAAFHAGATTRSFRMMAPPAAAAEIEEFLAAAERSE
        PtICK   (1) ---QNEGRS-------------APTSHEMEEFFAGAEQQQ
 SbICK partial  (48) RRRQTPSPPP--------PPPPPPTEAEIEAFFAAAELAE
ZmICK1 partial  (54) SSSPATTTSA--------AELIVPPAQEIQEFFAAAEAAH
ZmICK2 partial  (39) RVKAPPVHA-----------IPSSTEMNEYFAAAEQRRQ OsICK2 (230) AKRFAAKYNFDVVRGVPLDAG---RFEWTPVVSSRS
OsICK3 partial  (80) RRRFAEKY----------------------------
       OsICK4 (167) RQAFIDKYNFDPVNDCPLPG----RFEWVKID----
       OsICK5 (193) AERFAAKYNFDVVRGVPLDAGGAGRFEWTAVGSG--
        PtICK  (25) QRLFIERYNYDPVNDLPLSG----RYEWVRLRP---
 SbICK partial  (80) RRRFAEAYNYDVALDCPLEG----RFEWTPVNI---
ZmICK1 partial  (86) AKRFASKYNFDFVRGVPLDAG---RFEWTPGVSI--
ZmICK2 partial  (66) QQAFIDKYNFDPVNDCPLPG----RFEWVKID----
```

FIGURE 4

```
p21Cip1 - Cy-1   13 -  C G S K A C R R L F G P V D S
p21Cip1 - Cy-2  150 -  F Y H S K R R L I F S K R K P
p27Kip1          24 -  P K P S A C R N L F G P V D H
p57Kip2          25 -  V R T S A C R S L F G P V D H
Cdc25A            5 -        P S P A P R R L L F A C S P P
p107            652 -  T A G S A K R R L F G E D P P
E2F1            416 -  E E G E G I R D L F D C D F G
CONSENSUS                            R X H F
```

FIGURE 6

ICK1 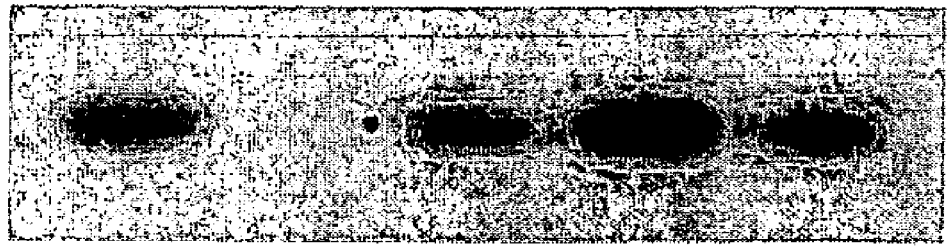
ICK2 
ICK4 
R    L    STM    ST    S
FIGURE 7

(A)

```
   1 GAAACCCTAG CCCCCTCCCA TCCCGAGTCC CGACCGCC(ATGGGCAAGTAC
  51 ATGCGCAAGG CCAAGGTGGT GGTCTCCGGC GAGGTGGTGG CCGCCGCCGT
 101 CATGGAGCTC GCCGCGGCGC CGCTCGGGGT GCGCACCCGC GCCCGCTCCC
 151 TCGCGCTGCA GAAGAGGCAG GGCGGGGAGT ACCTCGAGCT CAGGAGCCGC
 201 AGGCTCGAGA AGCTCCCTCC TCCCCCGCCG CCGCCGCCGA GGAGGAGGGC
 251 GACGGCTGCG GCTGCGACTG CTGATGCGAC GGCGACGGAG AGCGCGGAGG
 301 CGGAGGTGTC GTTCGGGGGG GAGAACGTCC TCGAGCTGGA GGCCATGGAA
 351 AGGAATACCA GGGAGACGAC ACCTTGCAGC TTGATCAGGG ACCCCGATAC
 401 GATTAGCACC CCTGGATCTA CCACAAGGCG CAGCCACTCG AGTTCTCATT
 451 GCAAGGTGCA AACACCCGTG CGCCACAACA TTATTCCAGC ATCAGCAGAG
 501 CTGGAAGCGT TCTTCGCYGC CGAAGAGCAA CGGCAACGAC AGGCTTTCAT
 551 CGACAAGTAT AACTTTGATC CTGTGAATGA CTGCCCTCTT CCCGGCCGRT
 601 TTGAATGGGT CAAGCTAGACTGA)TAGATTT TCAGGAAAAG AAGGGCACCA
 651 TGGACCTCTC TGCTCCCTCC ACAGTAGTAG CGTGGCAGAG GCGCTTACCG
 701 TCAAGTTAGC TTTGATCCTG TTGTAAAAAT TTAGGGTTAG CCTGTAGACT
 751 CAATGGTCAA TGTGAACATA CAGAACTGAT GCTGAGTTAC AACCCTAATC
 801 CCTCAACTAC AATGTAACCC TTAACAGCTC ATTCTGTAAG GAACCACCTC
 851 CTCCTCTAGG GCCTAGCTAG CCTTATCATC TGTTATTACC AGTTGCTGGA
 901 TTAATGAAGT TAGATCTAGA TATTGTGTCA CAGTTTAACC TGTTGTGTGT
 951 GTGGTGGTAG CATTGGCATT GGCAATGGGG TATGGCAGTG TGTGTGTGGT
1001 GCTGCACTGC ACCTCCCGAA GTGCTGTAAT TTTTGTCTAT ACTTCTGCTA
1051 AAAAAAAAAA AAAAAAA
```

(B)

```
                  1                                              50
2-H ICK4    (1)   --------------------------------------------------
HYB ICK4    (1)   MGKYMRKAKVVVSGEVVAAAVMELAAAPLGVRTRARSLALQKRQGGEYLE 51                                             100
2-H ICK4    (1)   ---------------PRRRATAAAATADATATESAEAEVSFGGENVLEL
HYB ICK4   (51)   LRSRRLEKLPPPPPPPPRRRATAAAATADATATESAEAEVSFGGENVLEL 101                                            150
2-H ICK4   (35)   EAMERNTRETTPCSLIRDPDTISTPGSTTRRSHSSSHCKVQTPVRHNIIP
HYB ICK4  (101)   EAMERNTRETTPCSLIRDPDTISTPGSTTRRSHSSSHCKVQTPVRHNIIP 151                                            195
2-H ICK4   (85)   ASAELEAFFAAEEQRQRQAFIDKYNFDPVNDCPLPGRFEWVKLD-
HYB ICK4  (151)   ASAELEAFFAAEEQRQRQAFIDKYNFDPVNDCPLPGRFEWVKLD-
```

FIGURE 11

```
1-    MGKYMRKAKV  VVSGEVVAAA  VMELAAAPLG  VRTRARSLAL  QKRQGGEYLE
51-   LRSRRLEKLP  PPPPPPPRRR  ATAAAATADA  TATESAEAEV  SFGGENVLEL
101-  EAMER[IAPFV  SLNCVKNTWV  APSPKYPRVG  ATCLQGTKGV  PYERDEQVLR
151-  HFW]NTRETTP  CSLIRDPDTI  STPGSTTRRS  HSSSHCKVQT  PVRHNIIPAS
201-  AELEAFFAAE  EQRQRQAFID  KYNFDPVNDC  PLPGRFEWVK  LD
```

FIGURE 12

```
   1 GAAACCCTAG CCCCCTCCCC TCCCGAGTCC CGACCGCCAT GGGCAAGTAC
  51 ATGCGCAAGG CCAAGGTGGT GGTCTCCGGC GAGGTGGTGG CCGCCGCCGT
 101 CATGGAGCTC GCCGCGGCGC CGCTCGGGGT GCGCACCCGC GCCCGCTCCC
 151 TCGCGCTGCA GAAGAGGCAG GGCGGGGAGT ACCTCGAGCT CAGGAGCCGC
 201 AGGCTCGAGA AGCTCCCTCC TCCCCCGCCG CCGCCGCCGA GGAGGAGGGC
 251 GACGGCTGCG GCTGCGACTG CTGATGCGAC GGCGGCGGAG AGCGCGGAGG
 301 CGGAGGTGTC GTTCGGGGGG GAGAACGTCC TCGAGCTGGA GGCCATGGAA
 351 AGGTGGGGAT TCTCTCTCTC TTCTTATTGT GCGATTCTTT TTTTGTTTTT
 401 CGTGGGTTTC TTGGTTGGAT TGATTGGGGG AATCGCGTGA TTAGGGTTCA
 451 GGGTTTAAGC ACCGTACGGG AGTTCTTGGG GTTCGATGTT TCTATCCGGT
 501 TTTTCGCATC GGAAAATTTT GGGGATTTTT TTTCGGTGCG ATTGTGGCGC
 551 TCGGAATTCC TGTGGCCAGT TTTGGGGTTT CGAAAGTATC GAAATGGAGG
 601 CGAGGAATCT TTTTTTTTTC CATCACACGC GGTTGTAAAG CCCCGATGCT
 651 TTCTTGGTGG GATTCTTGTC CCTTTGCTAA TTGAGACATG CAATTCGTGC
 701 TTTCCTTGTT GCCTAAATTT GTTCTTTTTC CATGTTTCTT GTGGCGATAC
 751 AGCCTTTTCT TTTTGCCAAT TTCTTGTCCC TTAGCTTGTT TACAAGTTAG
 801 AACCCATTTT AACTTCTTTT GAAGAAGGGA AAAAAGAAG AAGAGAAGGT
 851 GTTCCCAAGT TTTAATCCAA ATGGTTGCAA GAACCACTTC TTTGCCCCCC
 901 AAATTTACCT CGAAGAATCC CCCAAATTT GTTATTGTTT TGGATGATAA
 951 AAAGGTAGGA ACTGTGCAGT AGTGCTCAAG CTCTCAACTC AAATCCCAAT
1001 TGAAACTTGA TCAATTGATT GAGCCCCCT CTTAGTGGGG TTACTCCCAG
1051 TGGCCATGGC CTCCTGCTTT TCCTTAGTGG AAGGGAAAAG CAGCATCCTT
1101 TCCTCCTGT TCTTTGTGTT TTGTTTGGGG GGTAGGGACC CCTCTCAATC
1151 TTTTACCAAT CAAAAGCCCT CACCTTTTGC AAGAAATTTC TCTCATAAAC
1201 ATCCTTCCCA AAGGCACCCC CCATCTCACC ACCCACCTCA AGGCCTCATT
1251 CTTGCAACTA ACTAGCCTGT CACTTCTCTG GGTTCTGGAA GGGTGATGAA
1301 ATGGCATGCC TTGGTAAAAC CATCTTCCTG GGCCATGCCC CCAAATTGTC
1351 ACCACCATTA AATGTTTGAG GTGAAAGGAG GGGGTCCTCC CCCTCCCCAC
1401 AAGTACTAGA AGTTGATTTG TTGGTGATCT TTGGTTCAAG CTAGGGGAT
1451 GGAAGAACAT TTTAGGATCA GCTAGCTAGG CTACTACTAC TACTACTTGC
1501 TTCTGCAGTT CTTGGCAGGA TAATATTTTT AGCTACTACT ACTGTATCTC
1551 ACAAGCTAGC AAACGTTCTT GGTTCTAGCA CTATCTTGTG GAGGTGGGGG
1601 ATCTTCCTCA GCCTAAACAG GTCAAGACC CTATTTTGCT GGCGTGTCCT
1651 TTGGTGTAGG ATAGCTCCAT TTGTTAGCTT GAATTGTGTG AAAAATACAT
1701 GGGTTGCACC ATCACCGAAG TACCCAAGAG TGGGGCAAC TTGCTTGCAA
1751 GGGACAAAGG GCGTGCCGTA TGAGAGAGAT GAGCAAGTGC TGCGTCATTT
1801 TTGGTTTGTC ATCTTGGGTG CAAGATCAAG CAGCAGGTGT CACAGGACTC
1851 ACCACAGCTT GGGCTGTCCT TGGTGCCCCA TGTCCAAGGG TGCATTCATT
1901 GCACCTCCTC TAGCCATGGC CTAATGGTGC ATACTTCTGT GCCTCAAGGA
1951 CTGTTGTCTT TGAACCATTG ATGGATATCT ATCTGCATCC ATTTGTTTTA
2001 ATCCTTGGAA GCACCATGCG TGGCCTAAAT AGTGTGATCT GAACAGTGAG
2051 CATCTAAGCT AGCCATGGCC CTCCAAGCA TTTGCCATGG TGGAAGCTGC
2101 AGTGCAGAGT CAGCATGTGG TGTTGTTGCT GGGCCACTGT TGGTGACCGT
2151 CCTACCACCT TTTGCATGCA GCAGCAGCCA GCAGCAGCTT CGGATGCCGG
2201 TGCTTGGGTC TCTAGGATGG AGTTATGGCC GGGGGATCA CCTCACCTGA
```

FIGURE 19

```
2251 GCTAGTCATG TGATTCAGAT ATGGGAGCTC CTTAGACCAA ACCATTTTCT
2301 TGTTTCACTT GGCCTTGTGT TTGGTTGTCC CCTAGCCTTT TTTTGGCATG
2351 TGAGATAAAC ATTCAGAGGT GGAACATGGT TTATTTTGCA GGACCACGGC
2401 GATGCTGATT TTTTTTCTCA ATATTACCGG TGCATTTTTC TTGTTTAGTT
2451 TTTGGTACAA AAGAAAAAAA AGCTTACGTT GCATGTTCTG TTTTAAATTT
2501 GTATGCTTTT GTTTCTTGCA GGAATACCAG GGAGACGACA CCTTGCAGCT
2551 TGATCAGGGA CCCCGATACG ATTAGCACCC CTGGATCTAC CACAAGGCGC
2601 AGCCACTCGA GTTCTCATTG CAAGGTGCAA ACACCCGTGC GCCACAACAT
2651 TATTCCAGCA TCAGCAGAGC TGGAAGCGTT CTTCGCTGCC GAAGAGCAAC
2701 GGCAACGACA GGCTTTCATC GACAAGTACG ATCTTGCTTT GCTCTTCTAT
2751 TATGTTCAGT AAATATATCC CTGGATGCAT TGTGATAATG TCCATGGCCT
2801 TGCAACTTAG AAATACTATA ATGGTGTATT ATCGCTGACT GACAATTTAA
2851 CTTCTTTGTC GTAATCTTCA GGTATAACTT TGATCCTGTG AATGACTGCC
2901 CTCTTCCCGG CCGGTTTGAA TGGGTCAAGC TAGACTGATA GATTTTCAGG
2951 AAAAGAAGGG CACCATGGAC CTCTCTGCTC CCTCCACAGT AGTAGCGTGG
3001 CAGAGGCGCT TACCGTCAAG TTAGCTTTGA TCCTGTTGTA AAAATTTAGG
3051 GTTAGCCTGT AGACTAATG GTCAATGTGA ACATACAGAA CTGATGCTGA
3101 GTTACAACCC TAATCCCTCA ACTACAATGT AACCCTTAAC AGCTCATTCT
3151 GTAAGGAACC ACCTCCTCCT CTAGGGCCTA GCTAGCCTTA TCATCTGTTA
3201 TTACCAGTTG CTGGATTAAT GAAGTTAGAT CTAGATATTG TGTCACAGTT
3251 TAACCTGTTC TGTGTGTGGT GGTAGCATTG GCATTGGCAA TGGGGTATGG
3301 CAGTGTGTGT GTGGTGCTGC ACTGCACCTC CCGAAGTGCT GTAATTTTTG
3351 TCTATACTTC TGCT
```

FIGURE 19 (cont'd)

```
   1  ATGGCGAACA AGAAGAAGCG CGACGGCGCG GCGGCGAGGA GGCAGGCGCG
  51  GGTGGTGGTC GGCGGCGTCC GTACGCGGGC CGCCGTCACG GCGAGGAGGG
 101  TGGTGGCGAG CGCGGAGGAG GGTTGTGGTT TGGTGGGCCG TGGCGGTGGC
 151  GGTGGCAGTG GCGGAGACGA TGGCGAGGGC GGATGCTATC TGCGTCTGCG
 201  GAGCAGGAGG CTGCCCTTCG TGGCGGCCGC GGTGGTGTCG TCGCGGAGGG
 251  AGGAGGCGCT CGGTGATTCG GTGGCGGAGG CGGCTTCGTC GTCGTCGTCG
 301  CGGGCGGTGG AATTGTTGGG CTGTTCTGGT GAGGAGGAGG CTATGGCCGA
 351  GAAGGTGATT GATGAGCCCT AGAATTCCTC CGCGGCTCGA GTGCTCGATC
 401  GCCCGCTTCC ATCTCTTGCT GAATGATGCG GCTTGGGATG TGGTGGTTTT
 451  GCAGGTTTGC ACGCAGGCAG GCGAGGATCA CGACGAGGAG AGCTCCGTCG
 501  GCGACTCCGG CTGCGGCCGC GAGAGGTGAT CGAGCTCCTC TCCACGCGTT
 551  CTTGCTTGTC CTTGACATGA TTAATTACAA CCGCCGTTCT CTCAATTGAA
 601  TTATCGCAAT TCAATCCAGG AGCGCGACGA CGCCGTCGAG CCGCCGGCCG
 651  CCGGGAGACG CGGACTCGAG CGACGCGGAG TCAAACCAGG AGGCCAAGCA
 701  GCAAATGTGC CGCCGGAGTT CGACGACCTC AGCAGCTGCA TTTCACGCGG
 751  GAGCGACGAC GAGGAGCTTC AGGATGATGG CACCGCCGGC GGCGGCGGCA
 801  GAGATCGAGG AGTTCCTCGC CGCTGCGGAG AGGTCCGAGG CCGAGCGCTT
 851  CGCCGCCAAG TGAGTGCTGC ATCACATATT GTCGTCCGTG CGTCGTGTCG
 901  TACATATCGT CGTCGTCGTC AAAATCGGCC TCGATCGCGA CATGCATGGC
 951  CGCATGGGAG CTGATTAACG TGCGCTCCTC CTCCTCAGGT ACAACTTCGA
1001  CGTGGTGCGC GGCGTGCCGC TCGACGCCGG CGGCGCCGGG CGGTTCGAAT
1051  GGACCGCGGT GGGCAGCGGC TGA
```

```
  1  ATGGGGAAGA AGAAGAAGCG CGACGGCGCG GCGGCGAGGA GGCAGGCGCG
 51  GGTGGTGGTC GGCGGCGTCC GTACGCGGGC CGCCGTCACG GCGAGGAGGG
101  TGGTGGCGAG CGCGGAGGAG GGTTGTGGTT TGGTGGGCCG TGGCGGTGGC
151  GGTGGCAGTG GCGGAGACGA TGGCGAGGGC GGATGCTATC TGCGTCTGCG
201  GAGCAGGAGG CTGCCCTTCG TGGCGGCCGC GGTGGTGTCG TCGCGGAGGG
251  AGGAGGCGCT CGGTGATTCG GTGGCGGAGG CGGCTTCGTC GTCGTCGTCG
301  CGGGCGGTGG AATTGTTGGG CTGTTCTGGT GAGGAGGAGG CTATGGCCGA
351  GAAGNNGAGC GCGACGACGC CGTCGAGCCG CCGGCCGCCG GGAGACGCGG
401  ACTCGAGCGA CGCGGAGTCA AACCAGGAGG CCAAGCAGCA AATGTGCCGC
451  CGGAGTTCGA CGACCTCAGC AGCTGCATTT CACGCGGGAG CGACGACGAG
501  GAGCTTCAGG ATGATGGCAC CGCCGGCGGC GGCGGCAGAG ATCGAGGAGT
551  TCCTCGCCGC TGCGGAGAGG TCCGAGGCCG AGCGCTTCGC CGCCAAGTAC
601  AACTTCGACG TGGTGCGCGG CGTGCCGCTC GACGCCGGCG GCGCCGGGCG
651  GTTCGAATGG ACCGCGGTGG GCAGCGGCTG A
```

B.

```
  1  MGKKKKRDGA AARRQARVVV GGVRTRAAVT ARRVVASAEE GCGLVGRGGG
 51  GGSGGDDGEG GCYLRLRSRR LPFVAAAVVS SRREEALGDS VAEAASSSSS
101  RAVELLGCSG EEEAMAEKXS ATTPSSRRPP GDADSSDAES NQEAKQQMCR
151  RSSTTSAAAF HAGATTRSFR MMAPPAAAAE IEEFLAAAER SEAERFAAKY
201  NFDVVRGVPL DAGGAGRFEW TAVGSG
```

FIGURE 21

DOWN REGULATION OF PLANT CYCLIN-DEPENDENT KINASE INHIBITORS

CROSS REFERENCE TO RELATED APPLICATIONS

This application is a section 371 application of PCT/IB01/01492, filed Jun. 29, 2001, which claims the benefit under 35 U.S.C. §119(e) of U.S. Provisional Application Nos. 60/218,471, filed Jul. 14, 2000 and 60/241,219, filed Oct. 13, 2000.

RELATED APPLICATIONS

This application claims priority to U.S. provisional patent application Ser. No. 60/218,471, filed Jul. 14, 2000 and to U.S. provisional patent application Ser. No. 60/241,219, filed Oct. 13, 2000. The contents of these provisional patent applications are incorporated herein by reference in their entirety.

BACKGROUND TO THE INVENTION

When eukaryotic cells, e.g., plant cells, divide they go through a highly ordered sequence of events collectively termed as the "cell cycle." Briefly, DNA replication or synthesis (S) and mitotic segregation of the chromosomes (M) occur with intervening gap phases (G1 and G2) and the phases follow the sequence G1-S-G2-M. Cell division is completed after cytokinesis, the last step of the M-phase. Cells that have exited the cell cycle and have become quiescent are said to be in the G0 phase. Cells at the G0 stage can be stimulated to re-enter the cell cycle at the G1 phase.

The transition between the different phases of the cell cycle is basically driven by the sequential activation/inactivation of a kinase, known as "cyclin-dependent kinase" or "CDK" by different molecules. Required for kinase activation are proteins called cyclins which are also important for targeting the kinase activity to a given (subset of) substrate(s). Other factors regulating CDK activity include CDK inhibitors (known as CKIs, ICKs, Kips, Cips, Inks, or KRPs, i.e., Kip-related proteins), CDK activating kinase (CAK), CDK phosphatase (Cdc25), and CDK subunit (CKS) (Mironov et al. (1999) *Plant Cell* 11, 509-522 and Reed (1996). *Prog. Cell Cycle Res.* 2, 15-27).

The existence of an inhibitor of mitotic CDKs was inferred from experiments with endosperm of maize seed (Grafi and Larkins (1995) *Science* 269, 1262-1264) but only recently were ICKs identified in plants. A total of seven *Arabidopsis*, one *Chenopodium rubrum*, and one alfalfa ICK cDNAs have to date been described. The encoded proteins are characterized by a stretch of approximately 35 carboxy-terminal amino acids showing homology to the amino-terminal cyclin/Cdk binding domain of animal ICKs of the $p21^{CiP1}/p27^{Kip1}/p57^{KiP2}$-types. Outside the carboxy-terminal region, the plant ICKs are unrelated to one another and no homologies have been detected with other protein sequences.

*Arabidopsis* ICK1 is able to inhibit the kinase activity of plant Cdc2, but not the kinase activity of human Cdc2 or of *S. cerevisiae* Cdc28. *Arabidopsis* ICK3 also inhibits plant Cdc2 kinase activity. ICK1 and ICK3 interact both with *Arabidopsis* Cdc2a (A-type Cdk) and cyclin D3, but not with *Arabidopsis* Cdc2b (B-type Cdk). ICK1 also interacts with cyclin D1 and cyclin D2, but not with cyclin A2, cyclin B1, cyclin B2, or PCNA. As determined by yeast two-hybrid assays, interaction between ICK1 and cyclin D3 is much stronger than between ICK1 and Cdc2a The carboxy-terminal region of ICK1 (homologous to the Cip1/Kip1,2 animal ICKs) is required for association with Cdc2a and cyclin D3. Binding to either of these partners is, however, strongly enhanced with an amino-terminally deletion mutant comprising the approximately 50 amino acid stretch upstream of the ICK1 cyclin/Cdk binding domain in conjunction with this domain. Wild-type ICK1 does not fit as tightly to Cdc2a or cyclin D3 as the foregoing deletion mutant, suggesting the presence of destabilizing elements in the amino-terminal region of ICK1.

ICK1 expression is highest in leaves and both abscisic acid and incubation at low temperature conditions, which inhibit plant cell division, induce the accumulation of ICK1 transcripts in *Arabidopsis* seedlings. Expression of ICK2 is most prominent in stems and in florescence apices, lowest in 1-week-old seedlings and upregulated by treatment with 0.1% NaCl (WO9914331, Lui et al. (2000) *Plant J.* 21, 379-385, Wang et al. (1997) *Nature* 386, 451-452, WO9964599).

Transgenic *Arabidopsis, Brassica napus* and *B. carinata* plants have been generated expressing ICK1 under the control of the AP2 promoter sustaining pollen-preferred expression or under the control of the anther-specific Bgl1 promoter. Increased ICK1 mRNA levels in AP2-ICK1 transgenic *Arabidopsis* plants (T1 and T2) correlated with phenotypic effects ranging from no visible petals to visible petals of reduced size to normal petals. Only plants with normal petals are self-fertile. Seed setting in the male sterile transgenic plants with the other phenotypes can be restored by fertilization with wild-type pollen. No significant male sterility was observed in Bgl1-ICK1 transgenic *Arabidopsis* plants. The effects of AP2-ICK1 and Bgl1-ICK1 were less severe and more pronounced, respectively, in transgenic *Brassica* plants (WO9964599).

Many different functions have been described for ICKs of animal origin and these include: differential inhibition of cyclin-Cdk kinase activity, regulation of cyclin-Cdk complex assembly, regulation of commitment of cells to divide by integrating mitogenic and antimitogenic signals, regulation of cell cycle progression, regulation of DNA replication and DNA repair, regulation of gene transcription, regulation of cyclin degradation, involvement in cell cycle withdrawal and cell differentiation, regulation of apoptosis, control of organ and organism size and regulation of endoreduplication (Nakayama and Nakayama 1998 *Bioesseys* 20, 1020-1029). Many of these functions have been attributed to the ICK domains outside the cyclin/Cdk binding regions.

In view of the unusually pronounced sequence heterogeneity between the ICKs of a single plant species and the differences in expression patterns, it can be expected that each of the plant ICKs serves a unique function in controlling plant development. Such plant ICK functions may include interference with cell cycle events similar as those regulated by ICKs in animals but as yet unidentified in plants.

SUMMARY OF THE INVENTION

The present invention is based, at least in part, on the discovery of novel molecules, referred to herein as "Inhibitors of Cyclin Dependent Kinases" or "ICK" nucleic acid and polypeptide molecules. The ICK nucleic acid and polypeptide molecules of the present invention are useful as modulating agents in regulating cell cycle progression in, for example, plants. The ICK nucleic acid and polypeptide molecules of the present invention are particularly useful in agriculture and plant cell and tissue culture.

In one aspect, the present invention features a method for modulating the cell cycle in a plant, e.g., *arabidopsis thaliana*, rice, wheat, maize, tomato, alfalfa, oilseed rape, soybean, sunflower, or canola, by introducing into the plant an ICK modulator, such that the cell cycle in the plant is modulated. In one embodiment, the plant is a monocot plant. In another embodiment, the plant is a dicot plant.

In one embodiment, the ICK modulator is a small molecule. In another embodiment, the ICK modulator is capable of modulating ICK polypeptide activity. For example, the ICK modulator can be an anti-ICK antibody or an ICK polypeptide comprising the amino acid sequence of SEQ ID NO:10, 11, 12, 13, 14, 15, 16, 17, 44, or 55, or a fragment thereof.

In another embodiment, the ICK modulator is capable of modulating ICK nucleic acid expression. For example, the ICK modulator can be an antisense ICK nucleic acid molecule, an ICK gene silencing molecule, a ribozyme, or a nucleic acid molecule comprising the nucleotide sequence of SEQ ID NO:1, 2, 3, 4, 5, 6, 7, 8, 9, 43, 45, 54 or 56, or a fragment thereof.

In another aspect, the invention features a method for modulating plant growth and/or plant cell fate and/or plant morphology and/or plant biochemistry and/or plant physiology by introducing into a plant an ICK modulator, such that said plant growth and/or plant cell fate and/or morphology and/or plant biochemistry and/or plant physiology is modulated.

In a further aspect, the invention features a method for improving tolerance to an environmental stress condition, e.g., drought, salt, temperature, or nutrient deprivation, in a plant by introducing into the plant an ICK modulator, such that tolerance to an environmental stress condition in the plant is improved.

In another aspect, the invention features a method for improving tolerance to a plant pathogen, e.g., a pathogenic bacterium such as *Agrobacterium tumefaciens*, plant pathogenic fungi including *Plasmodiophora brassicae, Crinipellis perniciosa, Pucciniastrum geoppertianum, Taphrina wiesneri, Ustilaga maydis, Exobasidium vaccinii, E. camelliae, Entorrhiza casparyana* and *Apiosporina morbosum*, that abuses the cell cycle in a plant by introducing into the plant an ICK modulator, such that tolerance to a plant pathogen that abuses the cell cycle in the plant is improved.

In a further aspect, the invention features a method for modulating ICK activity in a plant by introducing into the plant an ICK modulator, such that ICK activity in the plant is modulated.

The present invention also features a method for modulating the cell cycle in a plant cell by contacting the plant cell with an ICK modulator, such that the cell cycle in the plant cell is modulated.

In another aspect, the invention provides a method for modulating plant cell growth and/or plant cell fate and/or plant morphology and/or plant biochemistry and/or plant physiology by contacting a plant cell with an ICK modulator, such that plant cell growth and/or plant cell fate and/or plant morphology and/or plant biochemistry and/or plant physiology is modulated.

Methods for improving tolerance to an environmental stress condition in a plant cell and methods for improving tolerance to a plant pathogen that abuses the cell cycle in a plant cell are also provided by the present invention. These methods include contacting the plant cell with an ICK modulator, such that tolerance to an environmental stress condition or to a plant pathogen that abuses the cell cycle in the plant cell is improved.

Methods for modulating ICK activity in a plant cell are also provided. The methods include contacting the plant cell with an ICK modulator, such that ICK activity in the plant cell is modulated.

In another embodiment the invention provides transgenic plants (e.g., monocot or dicot plants) containing an isolated nucleic acid molecule of the present invention. For example, the invention provides transgenic plants containing a recombinant expression cassette including a plant promoter operably linked to an isolated nucleic acid molecule of the present invention (e.g., a nucleic acid molecule comprising the nucleotide sequence set forth in SEQ ID NO:9, SEQ ID NO:43, SEQ ID NO:45, SEQ ID NO:54 or SEQ ID NO:56). The present invention also provides seed, pollen, cuttings, and flowers from the transgenic plants. In another embodiment the invention provides methods of modulating, in a transgenic plant, the expression of the nucleic acids of the invention.

Isolated nucleic acid molecules which include the nucleotide sequence set forth in SEQ ID NO: 9, SEQ ID NO:43, SEQ ID NO:45, SEQ ID NO:54 or SEQ ID NO:56, or complements thereof, are also encompassed by the present invention.

In one aspect, the invention features an isolated nucleic acid molecule which encodes an ICK polypeptide comprising the amino acid sequence set forth in SEQ ID NO:10, 11, 12, 13, 14, 15, 16, 17, 44, or 55, or a complement of the isolated nucleic acid molecule.

In another aspect, the present invention features an isolated ICK polypeptide comprising the amino acid sequence of SEQ ID NO:10, 11, 12, 13, 14, 15, 16, 17, 44, or 55, or fragments thereof.

The proteins of the present invention or portions thereof, e.g., biologically active portions thereof, can be operably linked to a non-ICK polypeptide (e.g., heterologous amino acid sequences) to form fusion proteins. The invention further features antibodies, such as monoclonal or polyclonal antibodies, that specifically bind to the ICK polypeptides of the invention. In addition, the ICK polypeptides or biologically active portions thereof can be incorporated into pharmaceutical compositions, which optionally include pharmaceutically acceptable carriers.

In another aspect, the present invention provides a method for identifying a compound which binds to an ICK polypeptide of the present invention. The method includes contacting the polypeptide, or a cell expressing the polypeptide with a test compound; and determining whether the polypeptide binds to the test compound. In one embodiment, the binding of the test compound to the polypeptide is detected by direct detection of test compound/polypeptide binding. In another embodiment, the binding of the test compound to the polypeptide is detected by detection of binding using a competition binding assay. In yet another embodiment, the binding of the test compound to the polypeptide is detected using an assay for ICK activity.

In yet another aspect, the present invention provides a method for modulating the activity of an ICK polypeptides of the present invention. The method includes contacting the polypeptide or a cell expressing the polypeptide with a compound which binds to the polypeptide in a sufficient concentration to modulate the activity of the polypeptide.

In a further aspect, the present invention provides a method for identifying a compound which modulates the activity of an ICK polypeptide of the present invention. The method includes contacting an ICK polypeptide with a test compound; and determining the effect of the test compound on the activity of the polypeptide to thereby identify a compound which modulates the activity of the polypeptide.

Other features and advantages of the invention will be apparent from the following detailed description and claims.

BRIEF DESCRIPTION OF THE DRAWINGS

FIG. 1 depicts the nucleotide sequence of the full length OsICK2 cDNA (SEQ ID NO:9). The open reading frame (between rounded brackets) the start codon and the stop codon (underlined) are indicated. Also indicated are the polyadenylation sites (double underlined), the AU-rich elements or AREs (italic), and the extra 3'UTR region of SEQ ID NO:9 compared to SEQ ID NO:1 (underlined between square brackets).

FIG. 2 depicts the nucleotide sequence of the full length OsICK4 cDNA (SEQ ID NO:43). The open reading frame (between rounded brackets) the start codon and the stop codon (underlined) are indicated. Also indicated is the AU-rich element or ARE (italic).

FIG. 3 depicts an amino acid alignment of the full-length OsICK2 amino acid sequence (SEQ ID NO:10), the full-length OsICK4 amino acid sequence (SEQ ID NO:43) and the predicted full-length OsICK5 amino acid sequence (SEQ ID NO:55) with the amino acid sequences of other known plant ICKs: the seven *Arabidopsis* ICKs (ICK1 to ICK7), the *Medicago sativa* ICK (alfalfa ICK), and the *Chenopodium rubrum* ICK (Chenopod ICK). The alignment was made using ClustalW as part of the VNTI (version 5.5; InforMax Inc.) software using default parameter settings (blosum 62 scoring matrix; gap opening penalties for pairwise and multiple alignment=10; gap extension penalty for pairwise alignment=0.1; gap extension penalty for multiple alignment=0.05). Identical amino acid residues are indicated in black shaded boxes. Conserved amino acid residues are indicated in grey shaded boxes according to the groups (M,I,L,V), (A,G,S,T), (R,K,H), (F,W,Y), (D,E) and (N, Q).

FIG. 4 depicts an amino acid alignment of the relevant parts of the full-length OsICK2 amino acid sequence (SEQ ID NO:10), the full-length OsICK4 amino acid sequence (SEQ ID NO:43) and the predicted full-length OsICK5 amino acid sequence (SEQ ID NO:55) with the partial amino acid sequence of OsICK1 (SEQ ID NO:11), the partial amino acid sequence of OsICK3 (SEQ ID NO:12), the partial amino acid sequence of the *Zea mays* ICK1 (SEQ ID NO:14), the partial amino acid sequence of the *Zea mays* ICK2 (SEQ ID NO:15), the partial amino acid sequence of the *Sorghum bicolor* ICK (SEQ ID NO:16), and the partial amino acid sequence of the *Pinus taeda* ICK (SEQ ID NO: 17). The alignment was made using ClustalW as part of the VNTI (version 5.5; InforMax Inc.) software using default parameter settings (blosum 62 scoring matrix; gap opening penalties for pairwise and multiple alignment=10; gap extension penalty for pairwise alignment=0.1; gap extension penalty for multiple alignment=0.05). Identical amino acid residues are indicated in black shaded boxes. Conserved amino acid residues are indicated in grey shaded boxes according to the groups (M,I,L,V), (A,G,S,T), (R,K,H), (F,W,Y), (D,E) and (N, Q).

FIG. 6 depicts the Cy-box-regions present in different mammalian proteins and the derived consensus sequence. p21Cip1, p27Kip1 and p57kip2 are three types of mammalian cyclin-dependent kinase inhibitors. Cdc25A is a G1/S specific protein phosphatase which has Cdc2-related proteins as substrates. p107 belongs to the family of pocket proteins also including p130 and pRB. E2F1 is a transcriptional activator involved in activation of S-phase specific gene expression. X may be any amino acid and H may be M,I,L or V.

FIG. 7 is a blot depicting the expression of OsICK1 ('ICK1'), OsICK2 ('ICK2') and OsICK4 ('ICK4') in different tissues of rice plants. cDNA obtained by RT-PCR was subjected to DNA gel blot analysis with biotin-labeled probes specific for OsICK1, OsICK2 and OsICK4. (R: root tissue, L: leaf tissue, STM: stem meristem tissue, ST: stem tissue, S: seeds).

FIG. 11 depicts A comparison of the OsICK4 cDNA sequences (Panel A) and OsICK4 protein sequences (Panel B) obtained by (i) yeast two-hybrid interaction screening of rice two-hybrid cDNA library using Cdc2-Os1 as bait and by (ii) hybridization screening of the same library. The full-length OsICK4 cDNA sequence obtained by hybridization screening is given in Panel A with the ORF between brackets. Further indicated in Panel A is the part of the OsICK4 cDNA missing in the clone identified by yeast two-hybrid interaction cloning, said part being indicated in underlined italics. The corresponding full-length OsICK4 amino acid sequence is given in Panel B where it is identified as "HYB ICK4". Further indicated in Panel B is the part of the amino acid sequence encoded by the partial OsICK4 clone as outlined in Panel A. The partial amino acid sequence is identified in Panel B as "2-H ICK4". Amino acids common to both proteins are shaded in grey.

FIG. 12 shows the wrongly predicted OsICK4 protein sequence present in GenBank (GenBank accession number AC069145 version 5 of Sep. 30, 2000; protein ID=AAG16867.1). The 48 superfluous amino acids in the predicted protein sequence not present in the protein sequence derived (SEQ ID NO:44) from the experimentally obtained OsICK4 cDNA (SEQ ID NO:43) are indicated between square brackets and as underlined boldface characters.

FIG. 19 depicts the genomic fragment corresponding to the full-length OsICK4 cDNA.

FIG. 20 depicts the genomic fragment corresponding to the predicted full-length OsICK5 cDNA. The depicted fragment (SEQ ID NO:56) corresponds to the inverse complement of nucleotides 6331 to 7403 of GenBank accession number AP003525.1 as available on Jun. 26, 2001. Indicated in grey shaded boxes are the positions of the primers (SEQ ID NO:57 and 58) used to amplify the OsICK5 genomic fragment.

FIG. 21 depicts the predicted full-length OsICK5 cDNA sequence (SEQ ID NO:54; panel A) and the full-length OsICK5 protein sequence deduced thereof (SEQ ID NO:55; panel B). Uncertain residues in the predicted cDNA are indicated by 'N' and marked by a grey shaded box. The translation of the uncertain nucleotide residues in the cDNA result in an uncertain amino acid residue 'X' in the deduced protein sequence also marked by a grey shaded box. Further indicated in panel (A) in grey shaded boxes are the positions of the primers (SEQ ID NO:57 and 58) used to amplify the OsICK5 cDNA. Indicated in black shaded boxes are the start and the stop codon.

DETAILED DESCRIPTION OF THE INVENTION

Figure 5:
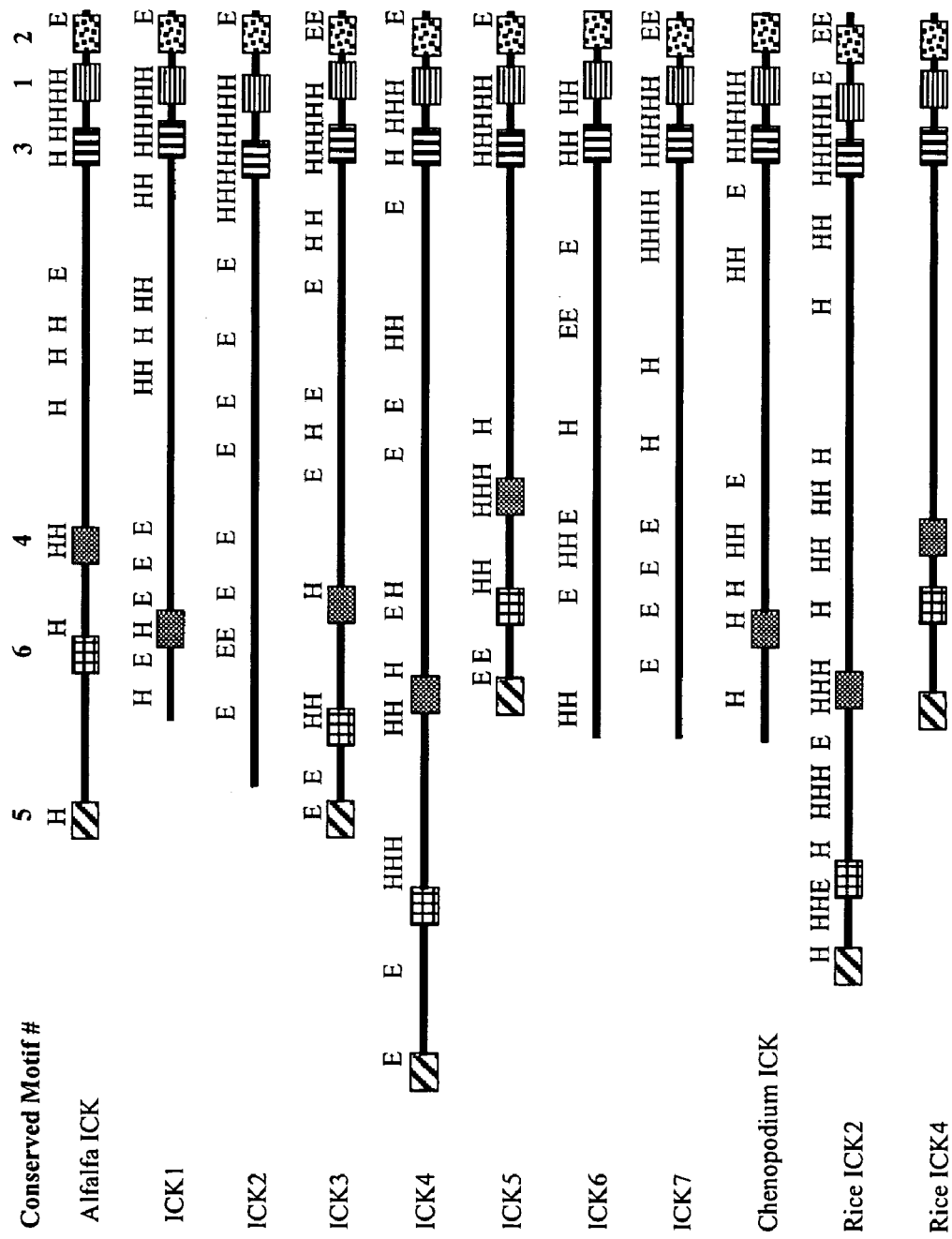
FIG. 5 is a schematic representation of the motifs conserved in plant ICK molecules (using the same numbering indicated in Table 1). Further indicated in FIG. 4 are the secondary structure elements predicted to be present in the plant ICK molecules. (H: predicted α-helical structure in a stretch of at least 4 consecutive amino acid residues. E: predicted extended β-sheet structure in a stretch of at least 4 consecutive amino acids).

The present invention is based, at least in part, on the discovery of novel molecules, referred to herein as "Inhibitors of Cyclin Dependent Kinases" or "ICK" nucleic acid and polypeptide molecules. In particular, the present invention is based on the discovery of the first monocotyledonous (monocot), e.g., cereal, ICK molecule. The ICK molecules of the present invention were identified by database mining using the "GRYEW" amino acid motif as a query sequence. This motif is present at the carboxyl-terminus of all known plant ICK molecules.

As used herein, the terms "Inhibitors of Cyclin Dependent Kinases" and "ICK" include molecules of the present invention which are capable of inhibiting the activity of a Cyclin Dependent Kinase (CDK), e.g., a plant CDK. CDKs are a group of serine/threonine kinases which regulate the progression of the cell cycle in eukaryotes, e.g., plants. CDKs are typically complexed with cyclins forming an enzyme complex, CDK being the catalytic subunit and cyclin being the regulatory subunit of the enzyme complex (Wang, H. (1997) *The Plant Journal* 15(4):501-510). ICK molecules of the present invention, e.g., ICK molecules from a monocot plant such as rice, typically have one or more of the following activities: inhibition of CDK activity (e.g., cyclin-CDK activity); regulation of cyclin-CDK complex assembly; regulation of the commitment of cells to divide, e.g., by integrating mitogenic and antimitogenic signals; regulation of cell cycle progression; regulation of DNA replication and/or DNA repair; they regulate gene transcription; regulation of cyclin degradation; involvement in cell cycle withdrawal and/or cell differentiation; regulation of cell death, e.g., apoptosis; control of organ (e.g., plant organ) and/or organism (e.g., plant organism) size; and regulation of endoreduplication.

As used herein, the term "cell cycle" includes the cyclic biochemical and structural events associated with growth, division, and proliferation of cells, and in particular with the regulation of the replication of DNA and mitosis. The cell cycle is divided into periods called: $G_0$, $Gap_1$ ($G_1$), DNA synthesis (S), $Gap_2$ ($G_2$), and mitosis (M). Normally these four phases occur sequentially, however, the term cell cycle also includes modified cycles wherein one or more phases are absent resulting in a modified cell cycle such as endomitosis, acytokinesis, polyploidy, polyteny, and endoreduplication.

As used herein, the term "plant" includes whole plants, plant organs (e.g., leaves, stems, or roots), plant tissue, plant seeds, and plant cells and progeny thereof. The class of plants which can be used in the methods of the invention is generally as broad as the class of higher plants amenable to transformation techniques, including both monocotyledonous and dicotyledonous plants. Particularly preferred plants are *Arabidopsis thaliana*, rice, wheat, barley, sorghum, maize, tomato, potato, cotton, alfalfa, oilseed rape, soybean, cotton, sunflower or canola. The term plant also includes monocotyledonous (monocot) plants and dicotyledonous (dicot) plants including a fodder or forage legume, ornamental plants, food crops, trees, or shrubs selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea fronuosa*, *Cadaba farinosa*, *Calliandra* spp, *Camellia sinensis*, *Canna indica*, *Capsicum* spp., *Cassia* spp., *Centroema pubescens*, *Chaenomneles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Diheteropogon amplectens*, *Dioclea* spp, *Dolichos* spp., *Dorycnium rectum*, *Echinochloa pyramidalis*, *Ehrartia* spp., *Eleusine coracana*, *Eragrestis* spp., *Erythrina* spp., *Eucalyptus* spp., *Euclea schimperi*, *Eulalia villosa*, *Fagopyrum* spp., *Feijoa sellowiana*, *Fragaria* spp., *Flemingia* spp, *Freycinetia banksii*, *Geranium thunbergii*, *Ginkgo biloba*, *Glycine javanica*, *Gliricidia* spp, *Gossypium hirsutum*, *Grevillea* spp., *Guibourtia coleosperma*, *Hedysarum* spp., *Hemarthia altissima*, *Heteropogon contortus*, *Hordeum vulgare*, *Hyparrhenia rufa*, *Hypericum erectum*, *Hyperthelia dissoluta*, *Indigo incarnata*, *Iris* spp., *Leptarrhena pyrolifolia*, *Lespediza* spp., *Lettuca* spp., *Leucaena leucocephala*, *Loudetia simplex*, *Lotonus bainesii*, *Lotus* spp., *Macrotyloma axillare, Malus* spp., *Manihot esculenta, Medicago sativa, Metasequoia glyptostroboides, Musa sapientum, Nicotianum* spp., *Onobrychis* spp., *Ornithopus* spp., *Oryza* spp., *Peltophorum africanum, Pennisetum* spp., *Persea gratissima, Petunia* spp., *Phaseolus* spp., *Phoenix canariensis, Phormium cookianum, Photinia* spp., *Picea glauca, Pinus* spp., *Pisum sativum, Podocarpus totara, Pogonarthria fleckii, Pogonarthria squarrosa, Populus* spp., *Prosopis cineraria, Pseudotsuga menziesii, Pterolobium stellatum, Pyrus communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys verticillata, Sequoia sempervirens, Sequoiadendron giganteum, Sorghum bicolor, Spinacia* spp., *Sporobolus fimbriatus, Stiburus alopecuroides, Stylosanthios humilis, Tadehagi* spp, *Taxodium distichum, Themeda triandra, Trifolium* spp., *Triticum* spp., *Tsuga heterophylla, Vaccinium* spp., *Vicia* spp., *Vitis vinifeia, Watsonia pyramidata, Zantedeschia aethiopica, Zea mays*, amaranth, artichoke, asparagus, broccoli, brussel sprout, cabbage, canola, carrot, cauliflower, celery, collard greens, flax, kale, lentil, oil seed rape, okra, onion, potato, rice, soybean, straw, sugarbeet, sugar cane, sunflower, tomato, squash, and tea, amongst others, or the seeds of any plant specifically named above or a tissue, cell or organ culture of any of the above species.

The term "plant cell", as used herein includes seeds, e.g., seed suspension cultures, embryos, cells from meristematic regions, cells from callus tissue, cells from leaves, cells from roots, cells from shoots, gametophytes, sporophytes, pollen, and microspores.

The ICK molecules of the present invention are involved in cell cycle regulation in plants. Accordingly, the ICK molecules of the present invention, or derivatives thereof, may be used to modulate the cell cycle in a plant by, for example, modulating the activity or level of expression of ICK; altering the rate of the cell cycle or phases of the cell cycle; or altering entry into and out of the various cell cycle phases. In plants, the ICK molecules of the present invention may be used in agriculture to, for example, improve the growth characteristics of a plant such as the growth rate of a plant; the size of specific tissues or organs in a plant; or the architecture or morphology of a plant. The ICK molecules of the present invention may also be used in agriculture to increase crop yield, improve tolerance to environmental stress conditions (such as drought, salt, temperature, or nutrient deprivation), improve tolerance to plant pathogens that abuse the cell cycle, or as targets to facilitate the identification of inhibitors or activators of ICKs that may be useful as herbicides or plant growth regulators.

As used herein, the term "cell cycle associated disorders" includes a disorder, disease or condition which is caused or characterized by a misregulation (e.g., downregulation or upregulation), abuse, arrest, or modification of the cell cycle. In plants cell cycle associated disorders include endomitosis, acytokinesis, polyploidy, polyteny, and endoreduplication which may be caused by external factors such as pathogens (nematodes, viruses, fungi, or insects), chemicals, environmental stress (e.g., drought, temperature, nutrients, or UV light) resulting in, for example, neoplastic tissue (e.g., galls, root knots) or inhibition of cell division/proliferation (e.g., stunted growth).

The present invention is based, at least in part, on the discovery of novel molecules, referred to herein as ICK protein and nucleic acid molecules, which comprise a family of molecules having certain conserved structural and functional features. The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of plant, e.g., rice, origin, as well as other, distinct proteins of plant, e.g., rice, origin or alternatively, can contain homologues of other plant, e.g. wheat or maize, or of non-plant origin. Members of a family may also have common functional characteristics.

In one embodiment of the invention, an ICK protein of the present invention, e.g., an ICK protein from a monocot plant such as rice, is identified based on the presence of at least one or more of the following motifs:

Motif 1: FXXKYNFD (SEQ ID NO:18), wherein X is any amino acid

Motif 2: [PL/]LXGRYEW (SEQ ID NO:19), wherein X is any amino acid and [P/L] means that either a proline or a leucine appear at the indicated position Motif 3: EXE[D/E]FFXXXE (SEQ ID NO:20), wherein X is any amino acid and [D/E] means that either an aspartate or a gluatamate appear at the indicated position Motif 4: YXQLRSRR (SEQ ID NO:21), wherein X is any amino acid Motif 5: MGKY[M/I][K/R]KX[K/R] (SEQ ID NO:22), wherein X is any amino acid, [M/I] means that either a methionine or an isoleucine appear at the indicated position, and [K/R] means that either a lysine or an arginine appear at the indicated position Motif 6: SXGVRTRA (SEQ ID NO:23), wherein X is any amino acid (The foregoing motifs are summarized in Table 1 and graphically represented in FIG. 4).

In a preferred embodiment, an ICK molecule of the present invention, e.g., an ICK molecule from a monocot plant such as rice, contains two, three, four, five, or, more preferably, all six of the foregoing motifs. All six motifs are present in the full-length OsICK2 (SEQ ID NO:10), full-length OsICK4 (SEQ ID NO:44) and predicted full-length OsICK5 (SEQ ID NO:55) proteins of the present invention. Although motifs 2 and 5 are present in the predicted full-length OsICK5 protein, they deviate from the consensus sequences.

Motifs 1, 2, and 3 are typically found in the carboxyl-terminal region of plant ICK proteins. This region is believed to be involved in the interaction of ICKs with both CDKs and cyclins (Chen et al. (1996) *Mol. Cell Biol* 16, 4673-4682, Matsuoka et al. (1995) *Genes Dev.* 9, 650-662, and Nakayama and Nakayama (1998) *Bioessays* 20, 1020-1029). Motifs 4, 5, and 6 are typically found in the amino-terminal region of plant ICK proteins.

TABLE 1

Conserved motifs in plant ICK proteins.
ICK1 to ICK7 denote the *Arabidopsis thaliana* ICKs.

| | Motif 1 | Motif 2 | Motif 3 | Motif 4 | Motif 5 | Motif 6 |
|---|---|---|---|---|---|---|
| Alfalfa ICK | 198-<br>FMEKYNFD | 211-<br>PLPGRYET | 182-<br>EFEEFCAKHE | 74-<br>YLQLRNRR | 1-<br>MGRYMKKLK | 45-<br>SDGVRTRA |
| ICK1 AC003040 | 167-<br>FKKKYNFD | 180-<br>PLEGRYEW | 151-<br>EIEOFEVEAE | 20-<br>YMQLRSRR | | |
| ICK2 AL132979 | 183-<br>CSMKYNFD | 197-<br>LGGGRYEW | 164-<br>ELEDFFQVAE | | | |
| ICK3 AB012242 | 197-<br>FMEKYNFD | 210-<br>PLSGRYEW | 181-<br>EMEEFFAYAE | 58-<br>YLQLRSRR | 1-<br>MGKYMKKSK | 26-<br>SPGVRTRA |
| ICK4 AC003974 | 264-<br>FIEKYNFD | 277-<br>PLPGRFEW | 248-<br>EMDEFFSGAE | 102-<br>YLQLRSRR | 1-<br>MGKYIRKSK | 44-<br>SLGVLTRA |
| ICK5 AB028609 | 164-<br>FIQKYNFD | 177-<br>PLPGRYEW | 148-<br>EIEDFFASAE | 54-<br>YLQLRSRR | 1-<br>MGKYIKKSK | 24-<br>ALGFRTRA |
| ICK6 AP000419 | 173-<br>FIEKYNFD | 186-<br>PLEGRYKW | 155-<br>EIEDLFSELE | | | |
| ICK7 AG011807 | 170-<br>FTEKYNYD | 183-<br>PLEGRYQW | 154-<br>ELDDFFSAAE | | | |
| *Chenopodium* ICK AJ002173 | 171-<br>FSEKYWFD | 184-<br>PLKGRYDW | 155-<br>EIEEFFAVAE | 25-<br>IPQLRSRR | | |
| OsICK2 | 233-<br>FAAKYNFD | 247-<br>LDAGRFEW | 217-<br>EIEAFFAAAE | 75-<br>YLQLRSRM | 1-<br>MGKYMRKFR | 24-<br>VVGVRTRS |
| OsICK1 | ----YNYD | PLQGRYEW | | | | |
| OsICK3 | FAEKY--- | | EIEAFFAAAE | | | |
| OsICK4 | 170-<br>FIDKYNFD | 183-<br>PLPGRFEW | 154-<br>ELEAFFAAEE | 48-<br>YLELRSRR | 1-<br>MGKYMRKAK | 28-<br>PLGVRTRA |
| OsICK5 | 196-<br>FAAKYNFD | 209-<br>PLDAGGAGRFEW | 180-<br>EIEEFLAAAE | 63-<br>YLRLRSRR | 1-<br>MGKKKRDG | 20-<br>VGGVRTRA |
| ZmICK1 | | FASKYNFD | LDAGRFEW | EIQEFFAAAE | | |
| ZmICK2 | | FIDEYNFD | PLPGRFEW | EMNEYFAAEQ | | |
| SbICK | | FAEAYNYD | PLEGRFEW | EIEAFAAAE | | |
| CONSENSUS | FX₂KYNFD | (P/L)LXGR[Y/F]EW | EXE(D/E)FFX₃E | YXGLRSRR | MGKY[M/I][K/R]KX[K/R] | SXGVRTRA |

The ICK proteins of the present invention from a monocot plant such as rice, in particular, are characterized by extensive α-helical stretches especially in between motifs 5 and 6 and in between motifs 6 and 4. Furthermore, in the ICK proteins of the present invention from a monocot plant such as rice, the region between motifs 4 and 3, only contains predicted α-helical segments and no extended β-sheets. These secondary structure characteristics of the ICK proteins from a monocot plant such as rice, are different from those found in alfalfa ICK and *Arabidopsis* ICKs ICK3, ICK4 and ICK5.

In another embodiment of the invention, an ICK protein of the present invention, e.g., an ICK protein from a monocot plant such as rice, is identified based on the presence of a "Cy-box." As used herein, the term "Cy-Box" includes an amino acid sequence of about 5 amino acid residues in length having the consensus sequence RXHuF (SEQ ID NO:24), wherein X is any amino acid and Hu is a hydrophobic uncharged amino acid, such as M, I, L or V (see FIG. 5). Cy-boxes are typically involved in the interaction of ICKs with cyclins. Amino acid residues 81-84 of the OsICK2 protein (SEQ ID NO: 10) are predicted to comprise a Cy-box (RMLF).

In another embodiment of the invention, an ICK protein of the present invention, e.g., an ICK protein from a monocot plant such as rice, is identified based on the presence of a "nuclear localization sequence." As used herein, the term "nuclear localization sequence" includes an amino acid sequence of about 4-20 amino acid residues in length, which serves to direct a protein to the nucleus. Typically, the nuclear localization sequence is rich in basic amino acids, such as arginine (R) and lysine (K). A nuclear localization signal may have one or more of the sequences depicted in Table 2. Nuclear localization signals are described in, for example, Gorlich D. (1998) EMBO 5.17:2721-7, the contents of which are incorporated herein by reference. Amino acid residues 54-57 of the OsICK2 protein (SEQ ID NO: 10) comprise a nuclear localization sequence. The Os ICK4 protein (SEQ ID NO:44) comprises multiple nuclear localization sequences as indicated in Table 2. Also the predicted full-length OsICK5 (SEQ ID NO:55) protein comprises an amino-terminal nuclear localization region (see Table 2).

TABLE 2

Potential nuclear localization sequences (NLSs) identified in plant ICKs using the PSORT/Prediction of protein localization sites software (http://psort.nibb.ac.jp).

| | NLS type | |
|---|---|---|
| ICK | 4-residue pattern | Robbins & Dingwall consensus |
| Alfalfa ICK | | 80[a]-RRLKRPLIRQHSAKRNK |
| Chenopodium ICK | | 15-KKVSKSSYNIPQLRSRR |
| ICK2 | 23-KRRK | |
| ICK4 | 123-KRRK | 108-RRLQKKPPIVVIRSTKR |
| | 240-HRRR | 112-KKPPIVVIRSTKRRKQQ |
| | 241-RRRP | |
| ICK5 | | 60-RRLVKLPLLTNTRKQQK |
| ICK7 | 5-KPKR | |
| | 142-KKKK | |
| OsICK2[b] | 54-RRRK | |

TABLE 2-continued

Potential nuclear localization sequences (NLSs) identified in plant ICKs using the PSORT/Prediction of protein localization sites software (http://psort.nibb.ac.jp).

| | NLS type | |
|---|---|---|
| ICK | 4-residue pattern | Robbins & Dingwall consensus |
| OsICK5 | 3-KKKK | |
| | 4-KKKR | |

[a]Position of the first amino acid of the site in the amino acid sequence of the indicated ICK.
[b]Identification of the OsICK2 NLSs was done manually, i.e., the protein sequence was not analyzed using the public PSORT software on the indicated Website.

PSORT uses the following two rules to detect it: 4 residue pattern composed of basic amino acids (K or R), or composed of three basic amino acids (K or R) and H or P; a pattern starting with P and followed within 3 residues by a basic segment containing 3 K or R residues out of 4 residues. Another type of nuclear targeting signal is the type of *Xenopus* nucleoplasmin proposed by Robbins et al. (J. Robbins, S. M. Dilworth, R. A. Laskey, and C. Dingwall, Cell, 64, 615, 1991). The pattern is: 2 basic residues, 10 residue spacer, and another basic region consisting of at least 3 basic residues out of 5 residues.

In a further embodiment of the invention, an ICK protein of the present invention, e.g., an ICK protein from a monocot plant such as rice, is identified based on the presence of a "PEST sequence." As used herein, the term "PEST sequence" includes an amino acid sequence which is enriched in the amino acid residues proline (P), glutamate (E), serine (S) and threonine (T) and which is present in proteins with a high proteolytic turnover rate. PEST sequences are described in, for example, Rogers et al. (1986) *Science* 234, 364-368, the contents of which are incorporated herein by reference. Amino acid residues 167-191 of the OsICK2 protein, amino acid residues 117-131 of the OsICK4 protein and amino acid residues 128-145 of the predicted full-length OsICK5 protein comprise potential PEST sequences (see Table 3).

TABLE 3

Potential PEST sequences identified in the plant ICKs using the PESTFIND software downloaded from http://ebi.ac.uk and run on a local server.

| ICK | Potential PEST sequences | PEST score |
|---|---|---|
| Alfalfa ICK | 11[a]-KSESPSPNSTPTPSPSPSPTPITTNSPPPTTPNSSDGVR | +24.12 |
| Chenopodium ICK | 105-RTADPEVESGEASSK | +11.43 |
| ICK2 | 71-RDSPPVEEQCQIEEEDSSVSCCSTSEEK | +15.46 |
| ICK4 | 243-RPTTPEMDEFFSGAEEQQK | +9.21 |
| ICK5 | 100-KLEPDTTTEEACGDNER | +13.68 |
| ICK6 | 24-KLNDSSDSSPDSH | +12.76 |
| | 118-KETSPVSEGLGETTTEMESSSATK | +15.73 |
| | 149-KTPTAAEIEDLFSELESQDDK | +8.59 |
| OsICK2 | 167-RETTPSSFLPGEVSDLESDLAGGQK | +4.75 |

TABLE 3-continued

Potential PEST sequences identified in the plant ICKs
using the PESTFIND software downloaded from
http://ebi.ac.uk and run on a local server.

| ICK | Potential PEST sequences | PEST score |
|---|---|---|
| OsICK4 | 117-RDPDTISTPGSTTR | +13.74 |
| OsICK5 | 128-RPPGDADSSDAESNQEAK | +13.12 |

<sup>a</sup>Position of the first amino acid of the site in the amino acid sequence of the indicated ICK.

Isolated ICK proteins of the present invention, e.g., ICK proteins from a monocot plant such as rice, have an amino acid sequence sufficiently identical to the amino acid sequence of SEQ ID NO:10, 11, 12, 13, 14, 15, 16, 17, 44 or 55, or are encoded by a nucleotide sequence sufficiently identical to SEQ ID NO: 1, 2, 3, 4, 5, 6, 7, 8, 9, 43, 45, 54 or 56. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% identity, preferably 60% identity, more preferably 70%-80%, and even more preferably 90-95% identity across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70-80%, or 90-95% identity and share a common functional activity are defined herein as sufficiently identical.

As used interchangeably herein, an "ICK activity", "biological activity of ICK" or "functional activity of ICK", refers to an activity exerted by an ICK protein, polypeptide or nucleic acid molecule on an ICK responsive cell or tissue, or on an ICK protein substrate, as determined in vivo, or in vitro, according to standard techniques. In one embodiment, an ICK activity is a direct activity, such as an association with an ICK-target molecule, e.g., a CDK or a cyclin molecule. Such interactions have been experimentally demonstrated in the current invention. As used herein, a "target molecule" or "binding partner" is a molecule with which an ICK protein binds or interacts in nature, such that ICK-mediated function is achieved. An ICK target molecule can be a non-ICK molecule, e.g., a CDK or a cyclin molecule, or an ICK protein or polypeptide of the present invention. In an exemplary embodiment, an ICK target molecule is an ICK ligand. Alternatively, an ICK activity is an indirect activity, such as a cellular signaling activity mediated by interaction of the ICK protein with an ICK ligand. The biological activities of ICK are described herein. For example, the ICK proteins of the present invention can have one or more of the following activities: (1) they may inhibit CDK activity (e.g., cyclin-CDK activity); (2) they may regulate cyclin-CDK complex assembly; (3) they may regulate the commitment of cells to divide, e.g., by integrating mitogenic and antimitogenic signals; (4) they may regulate cell cycle progression; (5) they may regulate DNA replication and/or DNA repair; (6) they may regulate gene transcription; (7) they may regulate cyclin degradation; (8) they may be involved in cell cycle withdrawal and/or cell differentiation; (9) they may regulate cell death, e.g., apoptosis; (10) they may control organ (e.g., plant organ) and/or organism (e.g., plant organism) size; and (11) they may regulate endoreduplication.

Accordingly, another embodiment of the invention features isolated ICK proteins and polypeptides having an ICK activity. Preferred proteins are ICK proteins, e.g., ICK proteins from a monocot plant such as rice, having at least one or more of the following domains: a motif 1, a motif 2, a motif 3, a motif 4, a motif 5, a motif 6, a Cy-box, a nuclear localization sequence, or a PEST sequence, extensive α-helical stretches, e.g. in between motifs 5 and 6, in between motifs 6 and 4, and in between motifs 4 and 3, and, preferably, an ICK activity.

Additional preferred proteins, e.g., ICK proteins from a monocot plant such as rice, have at least one or more of the following domains: a motif 1, a motif 2, a motif 3, a motif 4, a motif 5, a motif 6, a Cy-box, a nuclear localization sequence, or a PEST sequence, extensive α-helical stretches, e.g., in between motifs 5 and 6, in between motifs 6 and 4, and in between motifs 4 and 3, and are, preferably, encoded by a nucleic acid molecule having a nucleotide sequence which hybridizes under stringent hybridization conditions to a nucleic acid molecule comprising the nucleotide sequence of SEQ ID NO: 1, 2, 3, 4, 5, 6, 7, 8, 9, 43, 45, 54 or 56.

The sequences of the present invention are summarized below, in Table 4.

TABLE 4

| CLONE | ORGANISM | DNA SEQUENCE | PROTEIN SEQUENCE |
|---|---|---|---|
| OsICK1 (AQ574895) | Oryza sativa | 2 | 11 |
| OsICK2 | Oryza sativa | 1 (partial length) 9 (full length) | 10 |
| OsICK3 (AQ365042) | Oryza sativa | 3 | 12 |
| OsICK4 (AC069145) | Oryza sativa | 4 (partial length) 43 (full length) 45 (genomic fragment) | 13 (partial length) 44 (full length) |
| OsICK5 (AP003525) | Oryza sativa | 54 (predicted cDNA) 56 (genomic fragment) | 55 (predicted protein) |
| ZmICK1 (AI737717) | Zea mays | 5 | 14 |
| ZmICK2 (AW267370) | Zea mays | 6 | 15 |
| SbICK (AF061282) | Sorghum bicolor | 7 | 16 |
| PtICK (AA556411) | Pinus taeda | 8 | 17 |

Various aspects of the invention are described in further detail in the following subsections:

I. Uses and Methods of the Invention

The nucleic acid molecules, proteins, protein homologues, and antibodies described herein can be used in agricultural methods and screening assays. The isolated nucleic acid molecules of the invention can be used, for example, to express an ICK protein (e.g., via a recombinant expression vector in a host cell), to detect ICK mRNA (e.g., in a biological sample) or a genetic alteration in an ICK gene, and to modulate ICK activity, as described further below. The ICK proteins can be used to treat disorders characterized by insufficient or excessive production of an ICK substrate or production of ICK inhibitors. In addition, the ICK proteins can be used to screen for naturally occurring ICK substrates, to screen for drugs or compounds which modulate ICK activity, as well as to treat disorders characterized by insufficient or excessive production of ICK protein or production of ICK protein forms which have decreased or aberrant activity compared to ICK wild type protein. Moreover, the anti-ICK antibodies of the invention can be used to detect and isolate ICK proteins, regulate the bioavailability of ICK proteins, and modulate ICK activity.

A. Agricultural Uses:

In another embodiment of the invention, a method is provided for modifying cell fate and/or plant development and/or plant morphology and/or biochemistry and/or physiology comprising the modification of expression in particular cells, tissues or organs of a plant, of a genetic sequence encoding an ICK, e.g., an ICK operably connected with a plant-operable promoter sequence.

Modulation of the expression in a plant of an ICK or a homologue, analogue or derivative thereof as defined in the present invention can produce a range of desirable phenotypes in plants, such as, for example, the modification of one or more morphological, biochemical, or physiological characteristics including: (i) modification of the length of the G1 and/or the S and/or the G2 and/or the M phase of the cell cycle of a plant; (ii) modification of the G1/S and/or S/G2 and/or G2/M and/or M/G1 phase transition of a plant cell; (iii) modification of the initiation, promotion, stimulation or enhancement of cell division; (iv) modification of the initiation, promotion, stimulation or enhancement of DNA replication; (v) modification of the initiation, promotion, stimulation or enhancement of seed set and/or seed size and/or seed development; (vi) modification of the initiation, promotion, stimulation or enhancement of tuber formation; (vii) modification of the initiation, promotion, stimulation or enhancement of fruit formation; (viii) modification of the initiation, promotion, stimulation or enhancement of leaf formation; (ix) modification of the initiation, promotion, stimulation or enhancement of shoot initiation and/or development; (x) modification of the initiation, promotion, stimulation or enhancement of root initiation and/or development; (xi) modification of the initiation, promotion, stimulation or enhancement of lateral root initiation and/or development; (xii) modification of the initiation, promotion, stimulation or enhancement of nodule formation and/or nodule function; (xiii) modification of the initiation, promotion, stimulation or enhancement of the bushiness of the plant; (xiv) modification of the initiation, promotion, stimulation or enhancement of dwarfism in the plant; (xv) modification of the initiation, promotion, stimulation or enhancement of senescence; (xvi) modification of stem thickness and/or strength characteristics and/or wind-resistance of the stem and/or stem length; (xvii) modification of tolerance and/or resistance to biotic stresses such as pathogen infection; and (xviii) modification of tolerance and/or resistance to abiotic stresses such as drought stress or salt stress.

Methods to effect expression of an ICK or a homologue, analogue or derivative thereof as defined in the present invention in a plant cell, tissue or organ, include either the introduction of the protein directly to a cell, tissue or organ such as by microinjection of ballistic means or, alternatively, introduction of an isolated nucleic acid molecule encoding the protein into the cell, tissue or organ in an expressible format. Methods to effect expression of an ICK or a homologue, analogue or derivative thereof as defined in the current invention in whole plants include regeneration of whole plants from the transformed cells in which an isolated nucleic acid molecule encoding the protein was introduced in an expressible format.

The present invention clearly extends to any plant produced by the inventive method described herein, and any and all plant parts and propagules thereof. The present invention extends further to encompass the progeny derived from a primary transformed or transfected cell, tissue, organ or whole plant that has been produced by the inventive method, the only requirement being that the progeny exhibits the same genotypic and/or phenotypic characteristic(s) as those characteristic(s) that (have) been produced in the parent by the performance of the inventive method.

Exploiting plant ICK functions to regulate plant growth and development can depend on methods comprising enhancing ICK gene expression or ectopic expression of ICK genes. For example, a method for exploiting plant ICK function comprises suppression of ICK gene expression, thus, relieving negative control on cell cycle progression and positive control on cell differentiation.

In a preferred embodiment of the invention the cell cycle progression rate is modified by downregulation of expression of a plant ICK protein or a homologue or derivative thereof as defined in the present invention. ICK molecules interact with and inhibit the activity of cell cycle control molecules, e.g., Cdc2-related protein kinases or cyclins. Accordingly, decreased levels of ICK molecules result in a significant acceleration of the cell cycle progression. Downregulation of the expression of ICK can promote and extend cell division activity in cells that normally become quiescent during the course of development and/or as a consequence of adverse growth conditions and/or as a consequence of stress conditions. Downregulation of expression of ICK can, thus, be expected to increase the frequency of the formation of lateral organs including leaves (resulting in increased bushiness), flowers (resulting in increased numbers of seeds or seed pods) and roots (resulting in increased numbers of lateral roots). The timing of lateral organ formation can also be altered, e.g., resulting in earlier flowering. Another expected effect of delaying cells to become quiescent is the delayed occurrence of senescence. Downregulation of expression of ICK is furthermore expected to enhance growth under conditions of, e.g., salt or drought stress.

When downregulation of expression of ICK is occurring at the whole plant level, an overall growth enhancing effect is to be expected, i.e., recombinant plants will grow faster and/or will reach a larger size. This is particularly useful to increase the yield of, e.g., fodder plants, forage plants, leguminous plants, and wood-producing plants. Alternatively, downregulation of expression of ICK at the whole plant level may result in local growth enhancing effects, e.g., due to local and specific expression of the plant cellular proteins specifically targeted by said ICK. When downregulation of expression of ICK is confined to single cells, tissues, or organs of a plant, the growth enhancing effect will be confined to the single cells, tissues or organs of the plant. Particularly useful are restrictions of downregulation of expression of ICK to tissues or organs including seeds, fruits, tubers, roots, shoots, stems, and nodules to increase yield and/or size of these tissues or organs.

Thus, a preferred embodiment of the present invention involves downregulation of expression of an ICK protein or a homologue or derivative thereof as defined herein, in a plant cell and/or tissue and/or organ to obtain enhanced growth and/or delayed senescence of the plant cell and/or tissue and/or organ, or to obtain enhanced formation of lateral organs from the plant tissue and/or organ.

In another preferred embodiment downregulation of expression of an ICK protein or a homologue or derivative thereof as defined herein, in a whole plant results in enhanced growth and/or in increased frequency of lateral organ formation and/or delayed senescence of the plant.

Plant cells in which expression of an ICK is downregulated are furthermore expected to be stimulated to go through endoreduplication cycles, i.e., passage through consecutive cell cycles including DNA replication but without intervening cytokinesis. Cells undergoing endoreduplication, thus, become polyploid.

Downregulation of expression of ICK can further be used to increase seed yield and/or seed size. Grain yield in crop plants is largely a function of the amount of starch produced in the endosperm of the seed. The amount of protein produced in the endosperm is also a contributing factor to grain yield (Traas et al. (1998) *Current Opin. Plant Biol.* 1, 498-503). In contrast, the embryo and aleurone layers contribute little in terms of the total weight of the mature grain. By virtue of being linked to cell expansion and metabolic activity, endoreduplication is generally considered to be an important factor for increasing yield. As grain endosperm development initially includes extensive endoreduplication (Olsen et al. (1999) *Trends Plant Sci.* 4, 253-257), enhancing, promoting or stimulating this process is likely to result in increased grain yield. Enhancing, promoting or stimulating cell division during seed development as described supra is an alternative way to increase grain yield. In another aspect, the present invention also features a method for the production of $SiO_2$ from the peels or husks of larger rice seeds. Methods for extraction and/or production of pure $SiO_2$ from rice seed peels or husks are known in the art (e.g. Gorthy and Pudukottah 1999) and units for production of $SiO_2$ from rice seed peels are being set up (visit e.g. http://bisnis.doc.gov/bisnis/leads/990604sp.htm). $SiO_2$ has many applications including electronics, perfume industry and pharmacology and silicone production.

Another embodiment of the current invention comprises cell cycle stage-specific, developmental stage-specific and/or tissue-specific downregulation of expression of an ICK protein or a homologue or derivative thereof as defined herein. Downregulation of ICK expression can be obtained by using nucleotide sequences distinguishing alternatively polyadenylated transcripts of ICK (see Example 4). This approach has potential advantages such as, e.g., the fact that a constitutive promoter can be used to downregulate expression of ICK instead of a cell cycle phase-specific, developmental stage-specific or tissue-specific promoter.

In yet another preferred embodiment of the invention the cell cycle progression rate is significantly modified by ectopic expression of an ICK protein or a homologue or derivative thereof as defined herein. As ICK molecules interact with and inhibit the activity of cell cycle control, e.g., CDK, molecules, elevated levels of ICK result in a significant inhibition of the cell cycle progression. Thus, effects opposite to those obtainable as described for downregulation of expression of ICK can be expected. These opposite effects have useful applications as described infra. Ectopic expression of ICK at the whole plant level can, e.g., create dwarfism. Ectopic expression of ICK in specific cells, tissues or organs can be used to inhibit side shoot formation in crops such as tomato. Ectopic expression of ICK may also confer enhanced resistance to pathogens causing neoplastic plant growth, such as plant pathogenic bacteria including *Agrobacterium tumefaciens, Rhodococcus fascians, Pseudomonas savastnoi, Xanthomonas campestris pv citri* and *Erwinia herbicola*, plant pathogenic fungi including *Plasmodiophora brassicae, Crinipellis perniciosa, Pucciniastrum geoppertianum, Taphrina wiesneri, Ustilaga maydis, Exobasidium vaccinei, E. camelliae, Entorrhiza casparyana* and *Apiosporina morbosum*.

Ectopic expression of an ICK molecule may also confer enhanced resistance or tolerance against pathogens which rely on endoreduplication events in the infected host cells to survive. The ectopic expression of ICK is expected to inhibit endoreduplication events. Pathogens relying on host cell endoreduplication to, for example, establish a feeding structure, include nematodes such as *Heterodera* species and *Meloidogyne* species.

As used herein, the terms "ectopic expression" or "ectopic overexpression" of a gene or a protein refer to expression patterns and/or expression levels of the gene or protein normally not occurring under natural conditions.

By "cell fate and/or plant development and/or plant morphology and/or biochemistry and/or physiology" is meant that one or more developmental and/or morphological and/or biochemical and/or physiological characteristics of a plant is altered by the performance of one or more steps pertaining to the invention described herein.

"Cell fate" includes the cell-type or cellular characteristics of a particular cell that are produced during plant development or a cellular process therefor, in particular during the cell cycle or as a consequence of a cell cycle process.

The term "plant development" or the term "plant developmental characteristic" or similar terms shall, when used herein, be taken to mean any cellular process of a plant that is involved in determining the developmental fate of a plant cell, in particular the specific tissue or organ type into which a progenitor cell will develop. Cellular processes relevant to plant development will be known to those skilled in the art. Such processes include, for example, morphogenesis, photomorphogenesis, shoot development, root development, vegetative development, reproductive development, stem elongation, flowering, and regulatory mechanisms involved in determining cell fate, in particular a process or regulatory process involving the cell cycle.

The term "plant morphology" or the term "plant morphological characteristic" or similar term will, when used herein, be understood by those skilled in the art to include the external appearance of a plant, including any one or more structural features or combination of structural features thereof. Such structural features include the shape, size, number, position, color, texture, arrangement, and patternation of any cell, tissue or organ or groups of cells, tissues or organs of a plant, including the root, stem, leaf, shoot, petiole, trichome, flower, petal, stigma, style, stamen, pollen, ovule, seed, embryo, endosperm, seed coat, aleurone, fiber, fruit, cambium, wood, heartwood, parenchyma, aerenchyma, sieve element, phloem or vascular tissue.

The term "plant biochemistry" or the term "plant biochemical characteristic" or similar term will, when used herein, be understood by those skilled in the art to include the metabolic and catalytic processes of a plant, including primary and secondary metabolism and the products thereof, including any small molecules, macromolecules or chemical compounds, such as but not limited to starches, sugars, proteins, peptides, enzymes, hormones, growth factors, nucleic acid molecules, celluloses, hemicelluloses, calloses, lectins, fibbers, pigments such as anthocyanins, vitamins, minerals, micronutrients, or macronutrients, that are produced by plants.

The term "plant physiology" or the term "plant physiological characteristic" or similar term will, when used herein, be understood to include the functional processes of a plant, including developmental processes such as growth, expansion and differentiation, sexual development, sexual reproduction, seed set, seed development, grain filling, asexual reproduction, cell division, dormancy, germination, light adaptation, photosynthesis, leaf expansion, fibber production, secondary growth or wood production, amongst others; responses of a plant to externally-applied factors such as metals, chemicals, hormones, growth factors, environment and environmental stress factors (e.g., anoxia, hypoxia, high temperature, low temperature, dehydration, light, day length, flooding, salt, heavy metals, amongst others), including adaptive responses of plants to said externally-applied factors.

The ICK molecules of the present invention are useful in agriculture. The nucleic acid molecules, proteins, protein homologues, and antibodies described herein can be used to modulate the protein levels or activity of a protein involved in the cell cycle, e.g., proteins involved in the G1/S and/or the G2/M transition in the cell cycle.

Thus, the ICK molecules of the present invention may be used to modulate, e.g., enhance, crop yields; modulate, e.g., attenuate, stress, e.g., heat or nutrient deprivation, tolerance; modulate tolerance to pests and diseases; modulate plant architecture; modulate plant quality traits; or modulate plant reproduction and seed development.

The ICK molecules of the present invention may also be used to modulate endoreduplication in storage cells, storage tissues, and/or storage organs of plants or parts thereof. The term "endoreduplication" includes recurrent DNA replication without consequent mitosis and cytokinesis. Preferred target storage organs and parts thereof for the modulation of endoreduplication are, for example, seeds (such as from cereals, oilseed crops), roots (such as in sugar beet), tubers (such as in potatoes) and fruits (such as in vegetables and fruit species). Increased endoreduplication in storage organs, and parts thereof, correlates with enhanced storage capacity and, thus, with improved yield. In another embodiment of the invention, the endoreduplication of a whole plant is modulated.

B. Screening Assays:

The invention provides a method (also referred to herein as a "screening assay") for identifying modulators, i.e., candidate or test compounds or agents (e.g., peptides, peptidomimetics, small molecules or other drugs) which bind to ICK proteins, have a stimulatory or inhibitory effect on, for example, ICK expression or ICK activity, or have a stimulatory or inhibitory effect on, for example, the expression or activity of an ICK substrate.

In one embodiment, the invention provides assays for screening candidate or test compounds which are substrates of an ICK protein or polypeptide or biologically active portion thereof. In another embodiment, the invention provides assays for screening candidate or test compounds which bind to or modulate the activity of an ICK protein or polypeptide or biologically active portion thereof, e.g., modulate the ability of ICK to interact with its cognate ligand. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc Natl Acad Sci USA 89:1865-1869) or on phage (Scott and Smith (1990) Science 249:386-390); (Devlin (1990) Science 249:404-406); (Cwirla et al. (1990) Proc. Natl. Acad. Sci. 87:6378-6382); (Felici (1991) J. Mol. Biol. 222:301-310); (Ladner supra).

In another embodiment, an assay is a cell-based assay comprising contacting a cell expressing an ICK target molecule (e.g., a plant cyclin dependent kinase) with a test compound and determining the ability of the test compound to modulate (e.g. stimulate or inhibit) the activity of the ICK target molecule. Determining the ability of the test compound to modulate the activity of an ICK target molecule can be accomplished, for example, by determining the ability of the ICK protein to bind to or interact with the ICK target molecule, or by determining the ability of the target molecule, e.g., the plant cyclin dependent kinase, to phosphorylate a protein.

The ability of the target molecule, e.g., the plant cyclin dependent kinase, to phosphorylate a protein can be determined by, for example, an in vitro kinase assay. Briefly, a protein can be incubated with the target molecule, e.g., the plant cyclin dependent kinase, and radioactive ATP, e.g., [$\gamma$-$^{32}$P] ATP, in a buffer containing $MgCl_2$ and $MnCl_2$, e.g., 10 mM $MgCl_2$ and 5 mM $MnCl_2$. Following the incubation, the immunoprecipitated protein can be separated by SDS-polyacrylamide gel electrophoresis under reducing conditions, transferred to a membrane, e.g., a PVDF membrane, and autoradiographed. The appearance of detectable bands on the autoradiograph indicates that the protein has been phosphorylated. Phosphoaminoacid analysis of the phosphorylated substrate can also be performed in order to determine which residues on the protein are phosphorylated. Briefly, the radiophosphorylated protein band can be excised from the SDS gel and subjected to partial acid hydrolysis. The products can then be separated by one-dimensional electrophoresis and analyzed on, for example, a phosphoimager and compared to ninhydrin-stained phosphoaminoacid standards.

Determining the ability of the ICK protein to bind to or interact with an ICK target molecule can be accomplished by determining direct binding. Determining the ability of the ICK protein to bind to or interact with an ICK target molecule can be accomplished, for example, by coupling the ICK protein with a radioisotope or enzymatic label such that binding of the ICK protein to an ICK target molecule can be determined by detecting the labeled ICK protein in a complex. For example, ICK molecules, e.g., ICK proteins, can be labeled with $^{125}$I, $^{35}$S, $^{14}$C, or $^3$H, either directly or indirectly, and the radioisotope detected by direct counting of radioemission or by scintillation counting. Alternatively, ICK molecules can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interaction between ICK and its target molecule, without the labeling of any of the interactants. For example, a microphysiometer can be used to detect the interaction of ICK with its target molecule without the labeling of either ICK or the target molecule. McConnell, H. M. et al. (1992) *Science* 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, determining the ability of the ICK protein to bind to or interact with an ICK target molecule can be accomplished by determining the activity of the target molecule. For example, the activity of the target molecule can be determined by detecting induction of a cellular second messenger of the target, detecting catalytic/enzymatic activity of the target an appropriate substrate, detecting the induction of a reporter gene (comprising a target-responsive regulatory element operatively linked to a nucleic acid encoding a detectable marker, e.g., chloramphenicol acetyl transferase), or detecting a target-regulated cellular response.

In yet another embodiment, an assay of the present invention is a cell-free assay in which an ICK protein or biologically active portion thereof is contacted with a test compound and the ability of the test compound to bind to the ICK protein or biologically active portion thereof is determined. Binding of the test compound to the ICK protein can be determined either directly or indirectly as described above. In a preferred embodiment, the assay includes contacting the ICK protein or biologically active portion thereof with a known compound which binds ICK to form an assay mixture, contacting the assay mixture with a test compound, and determining the ability of the test compound to interact with an ICK protein, wherein determining the ability of the test compound to interact with an ICK protein comprises determining the ability of the test compound to preferentially bind to ICK or biologically active portion thereof as compared to the known compound.

In another embodiment, the assay is a cell-free assay in which an ICK protein or biologically active portion thereof is contacted with a test compound and the ability of the test compound to modulate (e.g., stimulate or inhibit) the activity of the ICK protein or biologically active portion thereof is determined. Determining the ability of the test compound to modulate the activity of an ICK protein can be accomplished, for example, by determining the ability of the ICK protein to bind to an ICK target molecule by one of the methods described above for determining direct binding. Determining the ability of the ICK protein to bind to an ICK target molecule can also be accomplished using a technology such as real-time Biomolecular Interaction Analysis (BIA). Sjolander, S. and Urbaniczky, C. (1991) *Anal. Chem.* 63:2338-2345 and Szabo et al. (1995) *Curr. Opin. Struct. Biol.* 5:699-705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of an ICK protein can be accomplished by determining the ability of the ICK protein to further modulate the activity of an ICK target molecule (e.g., an ICK mediated signal transduction pathway component). For example, the activity of the effector molecule on an appropriate target can be determined, or the binding of the effector to an appropriate target can be determined as previously described.

In yet another embodiment, the cell-free assay involves contacting an ICK protein or biologically active portion thereof with a known compound which binds the ICK protein to form an assay mixture, contacting the assay mixture with a test compound, and determining the ability of the test compound to interact with the ICK protein, wherein determining the ability of the test compound to interact with the ICK protein comprises determining the ability of the ICK protein to preferentially bind to or modulate the activity of an ICK target molecule.

The cell-free assays of the present invention are amenable to use of both soluble and/or membrane-bound forms of proteins (e.g., ICK proteins or biologically active portions thereof). In the case of cell-free assays in which a membrane-bound form a protein is used it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either ICK or its target molecule to facilitate separation of complexed from uncomplexed forms of one or both of the proteins, as well as to accommodate automation of the assay. Binding of a test compound to an ICK protein, or interaction of an ICK protein with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/ICK fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or ICK protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of ICK binding or activity determined using standard techniques.

Other techniques for immobilizing proteins on matrices can also be used in the screening assays of the invention. For example, either an ICK protein or an ICK target molecule can be immobilized utilizing conjugation of biotin and streptavidin. Biotinylated ICK protein or target molecules can be prepared from biotin-NHS(N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with ICK protein or target molecules but which do not interfere with binding of the ICK protein to its target molecule can be derivatized to the wells of the plate, and unbound target or ICK protein trapped in the wells by antibody conjugation. Methods for detecting such complexes, in addition to those described above for the GST-immobilized complexes, include immunodetection of complexes using antibodies reactive with the ICK protein or target molecule, as well as enzyme-linked assays which rely on detecting an enzymatic activity associated with the ICK protein or target molecule.

In another embodiment, modulators of ICK expression are identified in a method wherein a cell is contacted with a candidate compound and the expression of ICK mRNA or protein in the cell is determined. The level of expression of ICK mRNA or protein in the presence of the candidate compound is compared to the level of expression of ICK mRNA or protein in the absence of the candidate compound. The candidate compound can then be identified as a modulator of ICK expression based on this comparison. For example, when expression of ICK mRNA or protein is greater (statistically significantly greater) in the presence of the candidate compound than in its absence, the candidate compound is identified as a stimulator of ICK mRNA or protein expression. Alternatively, when expression of ICK mRNA or protein is less (statistically significantly less) in the presence of the candidate compound than in its absence, the candidate compound is identified as an inhibitor of ICK mRNA or protein expression. The level of ICK mRNA or protein expression in the cells can be determined by methods described herein for detecting ICK mRNA or protein.

In yet another aspect of the invention, the ICK proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with ICK ("ICK-binding proteins" or "ICK-bp") and are involved in ICK activity. Such ICK-binding proteins are also likely to be involved in the propagation of signals by the ICK proteins or ICK targets as, for example, downstream elements of an ICK-mediated signaling pathway. Alternatively, such ICK-binding proteins are likely to be ICK inhibitors.

The two-hybrid system is based on the modular nature of most transcription factors, which consist of separable DNA-binding and activation domains. Briefly, the assay utilizes two different DNA constructs. In one construct, the gene that codes for an ICK protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an ICK-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the ICK protein.

This invention further pertains to novel agents identified by the above-described screening assays. Accordingly, it is within the scope of this invention to further use an agent identified as described herein in an appropriate plant or animal model. For example, an agent identified as described herein (e.g., an ICK modulating agent, an antisense ICK nucleic acid molecule, an ICK-specific antibody, or an ICK-binding partner) can be used in a plant or animal model to determine the efficacy, toxicity, or side effects of treatment with such an agent. Alternatively, an agent identified as described herein can be used in a plant or animal model to determine the mechanism of action of such an agent. Furthermore, this invention pertains to uses of novel agents identified by the above-described screening assays for the agricultural and therapeutic uses described herein.

C. Detection Assays

Portions or fragments of the cDNA sequences identified herein (and the corresponding complete gene sequences) can be used in numerous ways as polynucleotide reagents. For example, these sequences can be used to: map their respective genes on a chromosome; and, thus, locate gene regions associated with genetic disease; identify an individual from a minute biological sample (tissue typing); and aid in forensic identification of a biological sample. Once the sequence (or a portion of the sequence) of a gene has been isolated, this sequence can be used to map the location of the gene on a chromosome. This process is called chromosome mapping. Accordingly, portions or fragments of the ICK nucleotide sequences, described herein, can be used to map the location of the ICK genes on a chromosome. The mapping of the ICK sequences to chromosomes is an important first step in correlating these sequences with genes associated with disease.

Briefly, ICK genes can be mapped to chromosomes by preparing PCR primers (preferably 15-25 bp in length) from the ICK nucleotide sequences. Computer analysis of the ICK sequences can be used to predict primers that do not span more than one exon in the genomic DNA, thus complicating the amplification process. These primers can then be used for PCR screening of cell hybrids containing individual plant or human chromosomes. Only those hybrids containing the plant or human gene corresponding to the ICK sequences will yield an amplified fragment.

Other mapping strategies which can similarly be used to map an ICK sequence to its chromosome include in situ hybridization (described in Fan, Y. et al. (1990) *Proc. Natl. Acad. Sci. USA,* 87:6223-27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature,* 325:783-787.

Moreover, differences in the DNA sequences between plants affected and unaffected with a disease associated with the ICK gene, can be determined. If a mutation is observed in some or all of the affected plants but not in any unaffected plants, then the mutation is likely to be the causative agent of the particular disease. Comparison of affected and unaffected plants generally involves first looking for structural alterations in the chromosomes, such as deletions or translocations that are visible from chromosome spreads or detectable using PCR based on that DNA sequence. Ultimately, complete sequencing of genes from several plants can be performed to confirm the presence of a mutation and to distinguish mutations from polymorphisms.

II. Isolated Nucleic Acid Molecules

One aspect of the invention pertains to isolated nucleic acid molecules that encode ICK proteins or biologically active portions thereof, as well as nucleic acid fragments sufficient for use as hybridization probes to identify ICK-encoding nucleic acids (e.g., ICK mRNA) and fragments for use as PCR primers for the amplification or mutation of ICK nucleic acid molecules. As used herein, the term "nucleic acid molecule" is intended to include DNA molecules (e.g., cDNA or genomic DNA) and RNA molecules (e.g., mRNA), chimeric RNA/DNA oligonucleotides, and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated ICK nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO: 1, 2, 3, 4, 5, 6, 7, 8, 9, 43, 45, 54 or 56, or a portion thereof, can be isolated using standard molecular biology techniques and the sequence information provided herein. For example, using all or portion of the nucleic acid sequence of SEQ ID NO: 1, 2, 3, 4, 5, 6, 7, 8, 9, 43, 45, 54 or 56, as a hybridization probe, ICK nucleic acid molecules can be isolated using standard hybridization and cloning techniques (e.g., as described in Sambrook, J., Fritsch, E. F., and Maniatis, T. *Molecular Cloning: A Laboratory Manual.* 2nd, ed, Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1, 2, 3, 4, 5, 6, 7, 8, 9, 43, 45, 54 or 56 can be isolated by the polymerase chain reaction (PCR) using synthetic oligonucleotide primers designed based upon the sequence of SEQ ID NO: 1, 2, 3, 4, 5, 6, 7, 8, 9, 43, 45, 54 or 56, respectively.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to ICK nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO: 1, 2, 3, 4, 5, 6, 7, 8, 9, 43, 45, 54 or 56.

In another preferred embodiment, an isolated nucleic acid molecule of the invention comprises a nucleic acid molecule which is a complement of the nucleotide sequence shown in SEQ ID NO:1, 2, 3, 4, 5, 6, 7, 8, 9, 43, 45, 54 or 56, or a portion of any of these nucleotide sequences. A nucleic acid molecule which is complementary to the nucleotide sequence shown in SEQ ID NO: 1, 2, 3, 4, 5, 6, 7, 8, 9, 43, 45, 54 or 56, is one which is sufficiently complementary to the nucleotide sequence shown in SEQ ID NO:1, 2, 3, 4, 5, 6, 7, 8, 9, 43, 45, 54 or 56, respectively, such that it can hybridize to the nucleotide sequence shown in SEQ ID NO: 1, 2, 3, 4, 5, 6, 7, 8, 9, 43, 45, 54 or 56, respectively, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 95%, 98% or more identical to the nucleotide sequence (e.g., to the entire length of the nucleotide sequence) shown in SEQ ID NO:1, 2, 3, 4, 5, 6, 7, 8, 9, 43, 45, 54 or 56, or a portion of any of these nucleotide sequences.

Moreover, the nucleic acid molecule of the invention can comprise only a portion of the nucleic acid sequence of SEQ ID NO:1, 2, 3, 4, 5, 6, 7, 8, 9, 43, 45, 54 or 56, for example a fragment which can be used as a probe or primer or a fragment encoding a biologically active portion of an ICK protein. The nucleotide sequence determined from the cloning of the ICK gene allows for the generation of probes and primers designed for use in identifying and/or cloning other ICK family members, as well as ICK homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1, 2, 3, 4, 5, 6, 7, 8, 9, 43, 45, 54 or 56, or of a naturally occurring allelic variant or mutant of SEQ ID NO:1, 2, 3, 4, 5, 6, 7, 8, 9, 43, 45, 54 or 56. In an exemplary embodiment, a nucleic acid molecule of the present invention comprises a nucleotide sequence which is at least 100, 150, 200, 250, 300, 350, 400, 450, 500, 550, 600, 650, 700, 750, or 800 nucleotides in length and hybridizes under stringent hybridization conditions to a nucleic acid molecule of SEQ ID NO:1, 2, 3, 4, 5, 6, 7, 8, 9, 43, 45, 54 or 56.

Probes based on the ICK nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissues which misexpress an ICK protein, such as by measuring a level of an ICK-encoding nucleic acid in a sample of cells from a subject e.g., detecting ICK mRNA levels or determining whether a genomic ICK gene has been mutated or deleted.

A nucleic acid fragment encoding a "biologically active portion of an ICK protein" can be prepared by isolating a portion of the nucleotide sequence of SEQ ID NO:1, 2, 3, 4, 5, 6, 7, 8, 9, 43, 45, 54 or 56, which encodes a polypeptide having an ICK biological activity (the biological activities of the ICK proteins are described herein), expressing the encoded portion of the ICK protein (e.g., by recombinant expression in vitro) and assessing the activity of the encoded portion of the ICK protein.

The invention further encompasses nucleic acid molecules that differ from the nucleotide sequence shown in SEQ ID NO: 1, 2, 3, 4, 5, 6, 7, 8, 9, 43, 45, 54 or 56, due to the degeneracy of the genetic code and, thus, encode the same ICK proteins as those encoded by the nucleotide sequence shown in SEQ ID NO:1, 2, 3, 4, 5, 6, 7, 8, 9, 43, 45, 54 or 56. In another embodiment, an isolated nucleic acid molecule of the invention has a nucleotide sequence encoding an ICK protein.

In addition to the ICK nucleotide sequences shown in SEQ ID NO: 1, 2, 3, 4, 5, 6, 7, 8, 9, 43, 45, 54 or 56, it will be appreciated by those skilled in the art that DNA sequence polymorphisms that lead to changes in the amino acid sequences of the ICK proteins may exist within a population (e.g., a rice plant population). Such genetic polymorphism in the ICK genes may exist among individuals within a population due to natural allelic variation. As used herein, the terms "gene" and "recombinant gene" refer to nucleic acid molecules which include an open reading frame encoding an ICK protein, preferably a plant ICK protein, and can further include non-coding regulatory sequences, and introns. Such natural allelic variations include both functional and non-functional ICK proteins and can typically result in 1-5% variance in the nucleotide sequence of an ICK gene. Any and all such nucleotide variations and resulting amino acid polymorphisms in ICK genes that are the result of natural allelic variation and that do not alter the functional activity of an ICK protein are intended to be within the scope of the invention.

Natural allelic variants are further include molecules that comprise single nucleotide polymorphisms (SNPs) as well as small insertion/deletion polymorphisms (INDELs; the size of INDELs is usually less than about 100 bp). SNPs and INDELs form the largest set of sequence variants in naturally occurring polymorphic strains of most organisms. They are helpful in mapping genes and in discovery of genes and gene functions. They are furthermore helpful in the identification of genetic loci, e.g., plant genes, involved in determining processes such as growth rate, plant size and plant yield, plant vigor, disease resistance, stress tolerance and the like. Many techniques are nowadays available to identify SNPs and/or INDELs including (i) PCR followed by denaturing high performance liquid chromatography (DHPLC; e.g., Cho et al. (1999) *Nature Genet* 23, 203-207); (ii) constant denaturant capillary electrophoresis (CDCE) combined with high-fidelity PCR (e.g., Li-Sucholeiki et al. (1999) *Electrophoresis* 20, 1224-1232); (iii) denaturing gradient gel electrophoresis (Fischer and Lerman (1983) *Proc. Natl. Acad. Sci. USA* 80, 1579-1583); (iv) matrix-assisted laser desorption/ionization time-of-flight mass spectrometry (MALDI-TOF MS; e.g., Ross et al (2000) *Biotechniques* 29, 620-629); (v) real-time fluorescence monitoring PCR assays (Tapp et al (2000) *Biotechniques* 28, 732-738); (vi) Acrydite™ gel technology (Kenney et al (1998) *Biotechniques* 25; 516-521); (vii) cycle dideoxy fingerprinting (CddF; Langemeier et al (1994) *Biotechniques* 17, 484-490); (vii) single-strand conformation polymorphism (SSCP) analysis (Vidal-Puig and Moller (1994) *Biotechniques* 17, 490-496) and (ix) mini-sequencing primer extension reaction (Syvanen (1999) *Hum Mutat* 13, 1-10). The technique of 'Targeting Induced Local Lesions in Genomes' (TILLING; McCallum et al. (2000) *Nat. Biotechnol* 8, 455-457; *Plant Physiol* 123, 439-442), which is a variant of (i) supra, can also be applied to rapidly identify an altered gene in, e.g., chemically mutagenized plant individuals showing interesting phenotypes.

Differences in preferred codon usage are illustrated below for *Agrobacterium tumefaciens* (a bacterium), *A. thaliana*, *M. sativa* (two dicotyledonous plants) and *Oryza sativa* (a monocotyledonous plant). For example, the codon GGC (for glycine) is the most frequently used codon in *A. tumefaciens* (36.2‰), is the second most frequently used codon in *O. sativa* but is used at much lower frequencies in *A. thaliana* and *M. sativa* (9‰ and 8.4‰, respectively). Of the four possible codons encoding glycine the GGC codon is most preferably used in *A. tumefaciens* and *O. sativa*. However, in *A. thaliana* the GGA (and GGU) codon is most preferably used, whereas in *M. sativa* the GGU (and GGA) codon is most preferably used.

Moreover, nucleic acid molecules encoding other ICK family members and, thus, which have a nucleotide sequence which differs from the ICK sequences of SEQ ID NO:1, 2, 3, 4, 5, 6, 7, 8, 9, 43, 45, 54 or 56 are intended to be within the scope of the invention. For example, another ICK cDNA can be identified based on the nucleotide sequence of the plant ICK molecules described herein. Moreover, nucleic acid molecules encoding ICK proteins from different species and, thus, which have a nucleotide sequence which differs from the ICK sequences of SEQ ID NO: 1, 2, 3, 4, 5, 6, 7, 8, 9, 43, 45, 54 or 56 are intended to be within the scope of the invention. For example, a corn ICK cDNA can be identified based on the nucleotide sequence of a rice ICK.

Nucleic acid molecules corresponding to natural allelic variants and homologues of the ICK cDNAs of the invention can be isolated based on their homology to the ICK nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1, 2, 3, 4, 5, 6, 7, 8, 9, 43, 45, 54 or 56. In other embodiment, the nucleic acid is at least 30, 50, 100, 150, 200, 250, 300, 350, 400, 450, 500, 550, or 600 nucleotides in length. As used herein, the term "hybridizes under stringent conditions" is intended to describe conditions for hybridization and washing under which nucleotide sequences at least 30%, 40%, 50%, or 60% identical to each other typically remain hybridized to each other. Preferably, the conditions are such that sequences at least about 70%, more preferably at least about 80%, even more preferably at least about 85% or 90% identical to each other typically remain hybridized to each other. Such stringent conditions are known to those skilled in the art and can be found in *Current Protocols in Molecular Biology*, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at about 45° C., followed by one or more washes in 0.2×SSC, 0.1% SDS at 50° C., preferably at 55° C., more preferably at 60° C., and even more preferably at 65° C. Ranges intermediate to the above-recited values, e.g., at 60-65° C. or at 55-60° C. are also intended to be encompassed by the present invention. Preferably, an isolated nucleic acid molecule of the invention that hybridizes under stringent conditions to the sequence of SEQ ID NO: 1, 2, 3, 4, 5, 6, 7, 8, 9, 43, 45, 54 or 56 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the ICK sequences that may exist in nature, the skilled artisan will further appreciate that changes can be introduced by mutation into the nucleotide sequences of SEQ ID NO:1, 2, 3, 4, 5, 6, 7; 8, 9, 43, 45, 54 or 56, thereby leading to changes in the amino acid sequence of the encoded ICK proteins, without altering the functional ability of the ICK proteins. For example, nucleotide substitutions leading to amino acid substitutions at "non-essential" amino acid residues can be made in the sequence of an ICK protein. A "non-essential" amino acid residue is a residue that can be altered from the wild-type sequence of ICK without altering the biological activity, whereas an "essential" amino acid residue is required for biological activity. For example, amino acid residues that are conserved among the ICK proteins of the present invention, are predicted to be particularly unamenable to alteration. Furthermore, additional amino acid residues that are conserved between the ICK proteins of the present invention and other ICK family members are not likely to be amenable to alteration.

Accordingly, another aspect of the invention pertains to nucleic acid molecules encoding ICK proteins that contain changes in amino acid residues that are not essential for activity.

An isolated nucleic acid molecule encoding an ICK protein homologous to the ICK proteins of the present invention can be created by introducing one or more nucleotide substitutions, additions or deletions into the nucleotide sequence of SEQ ID NO:1, 2, 3, 4, 5, 6, 7, 8, 9, 43, 45, 54 or 56, such that one or more amino acid substitutions, additions or deletions are introduced into the encoded protein. Mutations can be introduced into SEQ ID NO: 1, 2, 3, 4, 5, 6, 7, 8, 9, 43, 45, 54 or 56 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in an ICK protein is preferably replaced with another amino acid residue from the same side chain family. Alternatively, in another embodiment, mutations can be introduced randomly along all or part of an ICK coding sequence, such as by saturation mutagenesis, and the resultant mutants can be screened for ICK biological activity to identify mutants that retain activity. Following mutagenesis of SEQ ID NO: 1, 2, 3, 4, 5, 6, 7, 8, 9, 43, 45, 54 or 56, the encoded protein can be expressed recombinantly and the activity of the protein can be determined. Another alternative embodiment comprises targeted in vivo gene correction or modification which can be achieved by chimeric RNA/DNA oligonucleotides (e.g. Yoon et al. (1996), *Proc. Natl. Acad. Sci. USA* 93, 2071-2076).

In a preferred embodiment, a mutant ICK protein can be assayed for the ability to: (1) inhibit CDK activity (e.g., cyclin-CDK activity); (2) regulate cyclin-CDK complex assembly; (3) regulate the commitment of cells to divide, e.g., by integrating mitogenic and antimitogenic signals; (4) regulate cell cycle progression; (5) regulate DNA replication and/or DNA repair; (6) regulate gene transcription; (7) regulate cyclin degradation; (8) modulate cell cycle withdrawal and/or cell differentiation; (9) regulate cell death, e.g., apoptosis; (10) control organ (e.g., plant organ) and/or organism (e.g., plant organism) size; and (11) regulate endoreduplication.

In addition to the nucleic acid molecules encoding ICK proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire ICK coding strand, or only to a portion thereof. In one embodiment, an antisense nucleic acid molecule is antisense to a "coding region" of the coding strand of a nucleotide sequence encoding ICK. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding ICK. The term "noncoding region" refers to 5' and 3' sequences which flank the coding region that are not translated into amino acids (i.e., also referred to as 5' and 3' untranslated regions).

Given the coding strand sequences encoding ICK disclosed herein, antisense nucleic acids of the invention can be designed according to the rules of Watson and Crick base pairing. The antisense nucleic acid molecule can be complementary to the entire coding region of ICK mRNA, but more preferably is an oligonucleotide which is antisense to only a portion of the coding or noncoding region of ICK mRNA. For example, the antisense oligonucleotide can be complementary to the region surrounding the translation start site of ICK mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection). Preferably, production of antisense nucleic acids in plants occurs by means of a stably integrated transgene comprising a promoter operative in plants, an antisense oligonucleotide, and a terminator.

Other known nucleotide modifications include methylation, cyclization and 'caps' and substitution of one or more of the naturally occurring nucleotides with an analog such as inosine. Modifications of nucleotides include the addition of acridine, amine, biotin, cascade blue, cholesterol, Cy3®, Cy5®, Cy5.5® Dabcyl, digoxigenin, dinitrophenyl, Edans, 6-FAM, fluorescein, 3'-glyceryl, HEX, IRD-700, IRD-800, JOE, phosphate psoralen, rhodamine, ROX, thiol (SH), spacers, TAMRA, TET, AMCA-S®, SE, BODIPY®, Marina Blue®, Pacific Blue®, Oregon Green®, Rhodamine Green®, Rhodamine Red®, Rhodol Green® and Texas Red®. Polynucleotide backbone modifications include methylphosphonate, 2'-OMe-methylphosphonate RNA, phosphorothiorate, RNA, 2'-OMeRNA. Base modifications include 2-amino-dA, 2-aminopurine, 3'-(ddA), 3'dA (cordycepin), 7-deaza-dA, 8-Br-dA, 8-oxo-dA, $N^6$-Me-dA, abasic site (dSpacer), biotin dT, 2'-OMe-5Me-C, 2'-OMe-propynyl-C, 3'-(5-Me-dC), 3'-(ddC), 5-Br-dC, 5-I-dC, 5-Me-dC, 5-F-dC, carboxy-dT, convertible dA, convertible dC, convertible dG, convertible dT, convertible dU, 7-deaza-dG, 8-Br-dG, 8-oxo-dG, $O^6$-Me-dG, S6-DNP-dG, 4-methyl-indole, 5-nitroindole, 2'-OMe-inosine, 2'-dI, $O^6$-phenyl-dI, 4-methyl-indole, 2'-deoxynebularine, 5-nitroindole, 2-aminopurine, dP (purine analogue), dK (pyrimidine analogue), 3-nitropyrrole, 2-thio-dT, 4-thio-dT, biotin-dT, carboxy-dT, $O^4$-Me-dT, $O^4$-triazol dT, 2'-OMe-propynyl-U, 5-Br-dU, 2'-dU, 5-F-dU, 5-I-dU, $O^4$-triazol dU.

The antisense nucleic acid molecules of the invention are typically introduced into a plant or administered to a subject or generated in situ such that they hybridize with or bind to cellular mRNA and/or genomic DNA encoding an ICK protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of introduction or administration of antisense nucleic acid molecules of the invention include transformation in a plant or direct injection at a tissue site in a subject. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a constitutive promoter or a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330). In another embodiment, the antisense nucleic acid molecule further comprises a sense nucleic acid molecule complementary to the antisense nucleic acid molecule. Gene silencing methods based on such nucleic acid molecules are well known to the skilled artisan (e.g., Grierson et al. (1998) WO 98/53083; Waterhouse et al. (1999) WO 99/53050).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave ICK mRNA transcripts to thereby inhibit translation of ICK mRNA. A ribozyme having specificity for an ICK-encoding nucleic acid can be designed based upon the nucleotide sequence of an ICK cDNA disclosed herein (i.e., SEQ ID NO: 1, 2, 3, 4, 5, 6, 7, 8, 9, 43, 45, 54 or 56). For example, a derivative of a *Tetrahymena* L-19 IVS RNA can be constructed in which the nucleotide sequence of the active site is complementary to the nucleotide sequence to be cleaved in an ICK-encoding mRNA. See, e.g., Cech et al. U.S. Pat. No. 4,987,071; and Cech et al. U.S. Pat. No. 5,116,742. Alternatively, ICK mRNA can be used to select a catalytic RNA having a specific ribonuclease activity from a pool of RNA molecules. See, e.g., Bartel, D. and Szostak, J. W. (1993) *Science* 261:1411-1418. The use of ribozymes for gene silencing in plants is known in the art (e.g., Atkins et al.

(1994) WO 94/00012; Lenne et al. (1995) WO 95/03404; Lutziger et al. (2000) WO 00/00619; Prinsen et al. (1997) WO 97/13865 and Scott et al. (1997) WO/97/38116).

Alternatively, ICK gene expression can be inhibited by targeting nucleotide sequences complementary to the regulatory region of the ICK (e.g., the ICK promoter and/or enhancers) to form triple helical structures that prevent transcription of the ICK gene in target cells. See generally, Helene, C. (1991) *Anticancer Drug Des.* 6(6):569-84; Helene, C. et al. (1992) *Ann. NY. Acad. Sci.* 660:27-36; and Maher, L. J. (1992) *Bioassays* 14(12):807-15.

In yet another embodiment, the ICK nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670-675.

PNAs of ICK nucleic acid molecules can be used for increasing crop yield in plants or in therapeutic and diagnostic applications. For example, PNAs can be used as antisense or antigene agents for sequence-specific modulation of gene expression by, for example, inducing transcription or translation arrest or inhibiting replication. PNAs of ICK nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of ICK can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of ICK nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973-88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119-11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. US.* 86:6553-6556; Lemaitre et al. (1987) *Proc. Natl. Acad. Sci. USA* 84:648-652; PCT Publication No. WO88/09810) or the blood-brain barrier (see, e.g., PCT Publication No. WO89/10134). In addition, oligonucleotides can be modified with hybridization triggered cleavage agents (See, e.g., Krol et al. (1988) *Bio-Techniques* 6:958-976) or intercalating agents. (See, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

III. Isolated ICK Proteins and Anti-ICK Antibodies

One aspect of the invention pertains to isolated ICK proteins, and biologically active portions thereof, as well as polypeptide fragments suitable for use as immunogens to raise anti-ICK antibodies. In one embodiment, native ICK proteins can be isolated from cells or tissue sources by an appropriate purification scheme using standard protein purification techniques. In another embodiment, ICK proteins are produced by recombinant DNA techniques. Alternative to recombinant expression, an ICK protein or polypeptide can be synthesized chemically using standard peptide synthesis techniques.

An "isolated" or "purified" protein or biologically active portion thereof is substantially free of cellular material or other contaminating proteins from the cell or tissue source from which the ICK protein is derived, or substantially free from chemical precursors or other chemicals when chemically synthesized. The language "substantially free of cellular material" includes preparations of ICK protein in which the protein is separated from cellular components of the cells from which it is isolated or recombinantly produced. In one embodiment, the language "substantially free of cellular material" includes preparations of ICK protein having less than about 30% (by dry weight) of non-ICK protein (also referred to herein as a "contaminating protein"), more preferably less than about 20% of non-ICK protein, still more preferably less than about 10% of non-ICK protein, and most preferably less than about 5% non-ICK protein. When the ICK protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of ICK protein in which the protein is separated from chemical precursors or other chemicals which are involved in the synthesis of the protein. In one embodiment, the language "substantially free of chemical precursors or other chemicals" includes preparations of ICK protein having less than about 30% (by dry weight) of chemical precursors or non-ICK chemicals, more preferably less than about 20% chemical precursors or non-ICK chemicals, still more preferably less than about 10% chemical precursors or non-ICK chemicals, and most preferably less than about 5% chemical precursors or non-ICK chemicals.

Biologically active portions of an ICK protein include peptides comprising amino acid sequences sufficiently homologous to or derived from the amino acid sequence of the ICK protein, which include less amino acids than the full length ICK proteins, and exhibit at least one activity of an ICK protein. Typically, biologically active portions comprise a domain or motif with at least one activity of the ICK protein. A biologically active portion of an ICK protein can be a polypeptide which is, for example, at least 10, 25, 50, 100 or more amino acids in length.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the GAP program in the GCG software package (available at http://www.gcg.com), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to ICK nucleic acid molecules of the invention. BLAST protein searches can be performed with the XBLAST program, score=50, wordlength=3 to obtain amino acid sequences homologous to ICK protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

The invention also provides ICK chimeric or fusion proteins. As used herein, an ICK "chimeric protein" or "fusion protein" comprises an ICK polypeptide operatively linked to a non-ICK polypeptide. An "ICK polypeptide" refers to a polypeptide having an amino acid sequence corresponding to ICK, whereas a "non-ICK polypeptide" refers to a polypeptide having an amino acid sequence corresponding to a protein which is not substantially homologous to the ICK protein, e.g., a protein which is different from the ICK protein and which is derived from the same or a different organism. The non-ICK polypeptide can, for example, be (histidine)$_6$-tag, glutathione S-transferase, protein A, maltose-binding protein, dihydrofolate reductase, Tag.100 epitope (EETARFQPGYRS; SEQ ID NO:37), c-myc epitope (EQKLISEEDL; SEQ ID NO:38), FLAG®-epitope (DYKDDDK; SEQ ID NO:39), lacZ, CMP (calnodulin-binding peptide), HA epitope (YPYDVPDYA; SEQ ID NO:40), protein C epitope (EDQVDPRLIDGK; SEQ ID NO:41) or VSV epitope (YTDIEMNRLGK; SEQ ID NO:42).

Within an ICK fusion protein the ICK polypeptide can correspond to all or a portion of an ICK protein. In a preferred embodiment, an ICK fusion protein comprises at least one biologically active portion of an ICK protein. In another preferred embodiment, an ICK fusion protein comprises at least two biologically active portions of an ICK protein. Within the fusion protein, the term "operatively linked" is intended to indicate that the ICK polypeptide and the non-ICK polypeptide are fused in-frame to each other. The non-ICK polypeptide can be fused to the N-terminus or C-terminus of the ICK polypeptide.

For example, in one embodiment, the fusion protein is a GST-ICK fusion protein in which the ICK sequences are fused to the C-terminus of the GST sequences. Such fusion proteins can facilitate the purification of recombinant ICK.

In another embodiment, the fusion protein is an ICK protein containing a heterologous signal sequence at its N-terminus. In certain host cells (e.g., plant or mammalian host cells), expression and/or secretion of ICK can be increased through use of a heterologous signal sequence.

The ICK fusion proteins of the invention can be incorporated into pharmaceutical compositions and administered to a plant or a subject in vivo. The ICK fusion proteins can be used to affect the bioavailability of an ICK substrate. Use of ICK fusion proteins may be useful agriculturally for the increase of crop yields or therapeutically for the treatment of cellular growth related disorders, e.g., cancer. Moreover, the ICK-fusion proteins of the invention can be used as immunogens to produce anti-ICK antibodies in a subject, to purify ICK ligands and in screening assays to identify molecules which modulate the interaction of ICK with an ICK substrate, e.g., a CDK molecule or a cyclin molecule.

Preferably, an ICK chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A ICK-encoding nucleic acid can be cloned into such an expression vector such that the fusion moiety is linked in-frame to the ICK protein.

The present invention also pertains to variants of the ICK proteins which function as either ICK agonists (mimetics) or as ICK antagonists. Variants of the ICK proteins can be generated by mutagenesis, e.g., discrete point mutation or truncation of an ICK protein. An agonist of the ICK proteins can retain substantially the same, or a subset, of the biological activities of the naturally occurring form of an ICK protein. An antagonist of an ICK protein can inhibit one or more of the activities of the naturally occurring form of the ICK protein by, for example, competitively modulating a cellular activity of an ICK protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the ICK protein.

In one embodiment, variants of an ICK protein which function as either ICK agonists (mimetics) or as ICK antagonists can be identified by screening combinatorial libraries of mutants, e.g., truncation mutants, of an ICK protein for ICK protein agonist or antagonist activity. In one embodiment, a variegated library of ICK variants is generated by combinatorial mutagenesis at the nucleic acid level and is encoded by a variegated gene library. A variegated library of ICK variants can be produced by, for example, enzymatically ligating a mixture of synthetic oligonucleotides into gene sequences such that a degenerate set of potential ICK sequences is expressible as individual polypeptides, or alternatively, as a set of larger fusion proteins (e.g., for phage display) containing the set of ICK sequences therein. There are a variety of methods which can be used to produce libraries of potential ICK variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential ICK sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of an ICK protein coding sequence can be used to generate a variegated population of ICK fragments for screening and subsequent selection of variants of an ICK protein. In one embodiment, a library of coding sequence fragments can be generated by treating a double stranded PCR fragment of an ICK coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the ICK protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of ICK proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify ICK variants (Arkin and Yourvan (1992) *Proc. Natl. Acad. Sci. USA* 89:7811-7815; Delgrave et al. (1993) *Protein Engineering* 6(3):327-331).

In one embodiment, cell based assays can be exploited to analyze a variegated ICK library. For example, a library of expression vectors can be transfected into a cell line which ordinarily synthesizes and secretes ICK. The transfected cells are then cultured such that ICK and a particular mutant ICK are secreted and the effect of expression of the mutant on ICK activity in cell supernatants can be detected, e.g., by any of a number of enzymatic assays. Plasmid DNA can then be recovered from the cells which score for inhibition, or alternatively, potentiation of ICK activity, and the individual clones further characterized.

An isolated ICK protein, or a portion or fragment thereof, can be used as an immunogen to generate antibodies that bind ICK using standard techniques for polyclonal and monoclonal antibody preparation. A full-length ICK protein can be used or, alternatively, the invention provides antigenic peptide fragments of ICK for use as immunogens. The antigenic peptide of ICK comprises at least 8 amino acid residues and encompasses an epitope of ICK such that an antibody raised against the peptide forms a specific immune complex with ICK. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of ICK that are located on the surface of the protein, e.g., hydrophilic regions.

An ICK immunogen typically is used to prepare antibodies by immunizing a suitable subject, (e.g., rabbit, goat, mouse or other mammal) with the immunogen. An appropriate immunogenic preparation can contain, for example, recombinantly expressed ICK protein or a chemically synthesized ICK polypeptide. The preparation can further include an adjuvant, such as Freund's complete or incomplete adjuvant, or similar immunostimulatory agent. Immunization of a suitable subject with an immunogenic ICK preparation induces a polyclonal anti-ICK antibody response.

Accordingly, another aspect of the invention pertains to anti-ICK antibodies. The term "antibody" as used herein refers to immunoglobulin molecules and immunologically active portions of immunoglobulin molecules, i.e., molecules that contain an antigen binding site which specifically binds (immunoreacts with) an antigen, such as ICK. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind ICK. The term "monoclonal antibody" or "monoclonal antibody composition", as used herein, refers to a population of antibody molecules that contain only one species of an antigen binding site capable of immunoreacting with a particular epitope of ICK A monoclonal antibody composition thus typically displays a single binding affinity for a particular ICK protein with which it immunoreacts.

Polyclonal anti-ICK antibodies can be prepared as described above by immunizing a suitable subject with an ICK immunogen. The anti-ICK antibody titer in the immunized subject can be monitored over time by standard techniques, such as with an enzyme linked immunosorbent assay (ELISA) using immobilized ICK. If desired, the antibody molecules directed against ICK can be isolated from the mammal (e.g., from the blood) and further purified by well known techniques, such as protein A chromatography to obtain the IgG fraction. At an appropriate time after immunization, e.g., when the anti-ICK antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem* .255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med*, 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with an ICK immunogen as described above, and the culture supernatants of the resulting hybridoma cells are screened to identify a hybridoma producing a monoclonal antibody that binds ICK.

Any of the many well known protocols used for fusing lymphocytes and immortalized cell lines can be applied for the purpose of generating an anti-ICK monoclonal antibody (see, e.g., G. Galfre et al. (1977) *Nature* 266:55052; Gefter et al. *Somatic Cell Genet.*, cited supra; Lerner, *Yale J. Biol. Med*., cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind ICK, e.g., using a standard ELISA assay.

Alternative to preparing monoclonal antibody-secreting hybridomas, a monoclonal anti-ICK antibody can be identified and isolated by screening a recombinant combinatorial immunoglobulin library (e.g., an antibody phage display library) with ICK to thereby isolate immunoglobulin library members that bind ICK. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246: 1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrad et al. (1991) *Bio/Technology* 9:1373-1377; Hoogenboom et al. (1991) *Nuc. Acid Res.* 19:4133-4137; Barbas et al. (1991) *Proc. Natl. Acad. Sci. USA* 88:7978-7982; and McCafferty et al. *Nature* (1990) 348:552-554.

Additionally, recombinant anti-ICK antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

An anti-ICK antibody (e.g., monoclonal antibody) can be used to isolate ICK by standard techniques, such as affinity chromatography or immunoprecipitation. An anti-ICK antibody can facilitate the purification of natural ICK from cells and of recombinantly produced ICK expressed in host cells. Moreover, an anti-ICK antibody can be used to detect ICK protein (e.g., in a cellular lysate or cell supernatant) in order to evaluate the abundance and pattern of expression of the ICK protein. These antibodies can also be used, for example, for the immunoprecipitation and immunolocalization of proteins according to the invention as well as for the monitoring of the synthesis of such proteins, for example, in recombinant organisms, and for the identification of compounds interacting with the protein according to the invention.

Anti-ICK antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

IV. Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequences of the present invention. Such a manufacture provides the nucleotide or amino acid sequences, or a subset thereof (e.g., a subset of open reading frames (ORI's)) in a form which allows a skilled artisan to examine the manufacture using means not directly applicable to examining the nucleotide or amino acid sequences, or a subset thereof, as they exist in nature or in purified form.

In one application of this embodiment, a nucleotide or amino acid sequence of the present invention can be recorded on computer readable media. As used herein "computer readable media" includes any medium that can be read and accessed directly by a computer. Such media include, but are not limited to: magnetic storage media, such as floppy discs, hard disc storage medium, and magnetic tape; optical storage media such a CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein "recorded" refers to a process of storing information on computer readable medium. The skilled artisan can readily adopt any of the presently known methods for recording information on a computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase Oracle, or the like. The skilled artisan can readily adapt any number of dataprocessor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identity fragments or regions of the sequences of the invention which match a particular target sequence or target motif.

As used herein, a "target sequence" can be any DNA or amino acid sequence of six or more nucleotide or two or more amino acids. A skilled artisan can readily recognize that the longer a target sequence is, the less likely a target sequence will be present as a random occurrence in the database. The most preferred sequence length of a target sequence is from about 10 to 100 amino acids or form about 30 to 300 nucleotide residues. However, it is well recognized that commercially important fragments, such as sequence fragments involved in gene expression and protein processing, may be shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software of conducting search means are and can be used in the computer-based systems of the present invention. Examples of such software include, but are not limited to, MacPatter (FMBL), BLASTN and BASIX (NCBIA).

For example, software which implements the BLAST (Altschul et al. (1990) *J. Mol. Biol.* 215:403-410) and BLAZE (Brutlag et al. (1993) *Comp. Chem.* 17:203-207) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzyme used in various reactions and in the production of commercially useful metabolites.

Furthermore, folding simulations and computer redesign of structural motifs of the protein of the invention can be performed using appropriate computer programs (Olszewski et al. 1996, Hoffman et al. 1995). Computer modeling of protein folding can be used for the conformational and energetic analysis of detailed peptide and protein models (Monge et al. 1995, Renouf and Hounsell 1995). In particular, the appropriate programs can be used for the identification of interactive sites of the ICK and cyclin-dependent kinases, its ligand or other interacting proteins by computer assisted searches for complementary peptide sequences (Fassina and Melli 1994). Further appropriate computer systems for the design of protein and peptides are described in the prior art, for example in Berry and Brenner (1994), Wodak (1987). Pabo and Suchanek (1986). The results obtained form the above-described computer analysis can be used for, e.g. the preparation of peptidomimetics of the proteins of the invention or fragments thereof.

Furthermore, a three-dimensional and/or crystallographic structure of the protein of the invention can be used for the design of peptidomimetic inhibitors of the biological activity of the protein of the invention (Rose et al. 1996, Rutenber et al. 1996).

V. Recombinant Expression Vectors and Host Cells

Another aspect of the invention pertains to vectors, preferably expression vectors, containing a nucleic acid encoding an ICK protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, e.g., a plant cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., ICK proteins, mutant forms of ICK proteins, fusion proteins, and the like).

The vectors of the invention comprise a selectable and/or scorable marker. Selectable marker genes useful for the selection of transformed plant cells, callus, plant tissue and plants are well known to those skilled in the art and comprise, for example, antimetabolite resistance as the basis of selection for dhfr, which confers resistance to methotrexate (Reiss, Plant Physiol. (Life Sci. Adv.) 13 (1994), 143-149); npt, which confers resistance to the aminoglycosides neomycin, kanamycin and paromycin (Herrera-Estrella, *EMBO J.* 2 (1983), 987-995) and hygro, which confers resistance to hygromycin (Marsh, *Gene* 32 (1984), 481-485). Additional selectable genes have been described, namely trpB, which allow cells to utilize indole in place of tryptophan; hisD, which allows cells to utilize histinol in place of histidine (Hartman, *Proc. Natl. Acad. Sci. USA* 85 (1988), 8047); mannose-6-phosphate isomerase which allows cells to utilize mannose (WO 94/20627) and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.) or deaminase from *Aspergillus terreus* which confers resistance to Blasticidin S (Tamura, *Biosci. Biotechnol. Biochem.* 59 (1995), 2336-2338).

Useful scorable markers are also known to those skilled in the art and are commercially available. Advantageously, the marker is a gene encoding luciferase (Giacomin, *Pl. Sci.* 116 (1996), 59-72; Scikantha, *J. Bact.* 178 (1996), 121), green fluorescent protein (Gerdes, *FEBS Lett.* 389 (1996), 4447) or β-glucuronidase (Jefferson, *EMBO J.* 6 (1987), 3901-3907). This embodiment is particularly useful for simple and rapid screening of cells, tissues and organisms containing a vector of the invention.

A "plant promoter" is a promoter capable of initiating transcription in plant cells. Exemplary plant promoters include, but are not limited to, those that are obtained from plants, plant viruses, and bacteria. Preferred promoters nay contain additional copies of one or more specific regulatory elements, to further enhance expression and/or to alter the spatial expression and/or temporal expression of a nucleic acid molecule to which it is operably connected. For example, copper-responsive, glucocorticoid-responsive or dexamethasone-responsive regulatory elements may be placed adjacent to a heterologous promoter sequence driving expression of a nucleic acid molecule to confer copper inducible, glucocorticoid-inducible, or dexamethasone-inducible expression respectively, on said nucleic acid molecule. Examples of promoters under developmental control include promoters that preferentially initiate transcription in certain tissues, such as leaves, roots, seeds, endosperm, embryos, fibers, xylem vessels, tracheids, or sclerenchyma. Such promoters are referred to as "tissue preferred." Promoters which initiate transcription only in certain tissue are referred to as "tissue specific." A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an ICK protein can be expressed in plant cells, bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual* 2nd, ed., Cold Spring Harbor Laboratory, Cold Spring Harbor Laboratory Press, Cold Spring Harbor, N.Y., 1989), and other laboratory manuals.

Means for introducing a recombinant expression vector of this invention into plant tissue or cells include, but are not limited to, transformation using $CaCl_2$ and variations thereof, in particular the method described by Hanahan (J. Mol. Biol. 166, 557-560, 1983), direct DNA uptake into protoplasts (Krens et al, Nature 296: 72-74, 1982; Paszkowski et al, EMBO J. 3:2717-2722, 1984), PEG-mediated uptake to protoplasts (Armstrong et al, Plant Cell Reports 9: 335-339, 1990) microparticle bombardment, electroporation (Fromm et al., Proc. Natl. Acad. Sci. (USA) 82:5824-5828, 1985), microinjection of DNA (Crossway et al., Mol. Gen. Genet. 202:179-185, 1986), microparticle bombardment of tissue explants or cells (Christou et al, Plant Physiol 87: 671-674, 1988; Klein et al. (1992) *Biotechnology* 24, 384-386), vacuum-infiltration of tissue with nucleic acid, or in the case of plants, T-DNA-mediated transfer from *Agrobacterium* to the plant tissue as described essentially by An et al. (EMBO J 4:277-284, 1985), Herrera-Estrella et al. (Nature 303: 209-213, 1983a; EMBO J. 2: 987-995, 1983b; In: Plant Genetic Engineering, Cambridge University Press, N.Y., pp 63-93, 1985), or in planta method using *Agrobacterium tumefaciens* such as that described by Bechtold et al., (*C.R. Acad. Sci. (Paris, Sciences de la vie/Life Sciences*) 316: 1194-1199, 1993) or Clough et al (*Plant J.* 16: 735-743, 1998). Methods for transformation of monocotyledonous plants are well known in the art and include *Agrobacterium*-mediated transformation (Cheng et al. (1997) WO 97/48814; Hansen (1998) WO 98/54961; Hiei et al. (1994) WO 94/00977; Hiei et al. (1998) WO 98/17813; Rikiishi et al. (1999) WO 99/04618; Saito et al. (1995) WO 95/06722), microprojectile bombardment (Adams et al. (1999) U.S. Pat. No. 5,969,213; Bowen et al. (1998) U.S. Pat. No. 5,736,369; Chang et al. (1994) WO 94/1-3822; Lundquist et al. (1999) U.S. Pat. No. 5,874,265/ U.S. Pat. No. 5,990,390; Vasil and Vasil (1995) U.S. Pat. No. 5,405,765; Walker et al. (1999) U.S. Pat. No. 5,955,362), DNA uptake (Eval et al. (1993) WO 93/181,168), microinjection of *Agrobacterium* cells (von Holt 1994 DE 4309203) and sonication (Finer et at (1997) U.S. Pat. No. 5,693,512). The vector DNA may further comprise a selectable marker gene to facilitate the identification and/or selection of cells which are transfected or transformed with a genetic construct. Suitable selectable marker genes contemplated herein include the ampicillin resistance ($Amp^r$), tetracycline resistance gene $Tc^r$), bacterial kanamycin resistance gene ($Kan^r$), phosphinothricin resistance gene, neomycin phosphotransferase gene (nptII), hygromycin resistance gene, β-glucuronidase (GUS) gene, chloramphenicol acetyltransferase (CAT) gene, green fluorescent protein (gfp) gene (Haseloff et al, 1997), and luciferase gene.

For microparticle bombardment of cells, a microparticle is propelled into a cell to produce a transformed cell. Any suitable ballistic cell transformation methodology and apparatus can be used in performing the present invention. Exemplary apparatus and procedures are disclosed by Stomp et al (U.S. Pat. No. 5,122,466) and Sanford and Wolf (U.S. Pat. No. 4,945,050). When using ballistic transformation procedures, the gene construct may incorporate a plasmid capable of replicating in the cell to be transformed. Examples of microparticles suitable for use in such systems include 1 to 5 μm gold spheres. The DNA construct may be deposited on the microparticle by any suitable technique, such as by precipitation.

A whole plant may be regenerated from the transformed or transfected cell, in accordance with procedures well known in the art. Plant tissue capable of subsequent clonal propagation, whether by organogenesis or embryogenesis, may be transformed with a gene construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem).

The term "organogenesis", as used herein, includes a process by which shoots and roots are developed sequentially from meristematic centres.

The term "embryogenesis", as used herein, includes a process by which shoots and roots develop together in a concerted fashion (not sequentially), whether from somatic cells or gametes.

Preferably, the plant is produced according to the methods of the invention by transfecting or transforming the plant with a genetic sequence, or by introducing to the plant a protein, by any art-recognized means, such as microprojectile bombardment, microinjection, *Agrobacterium*-mediated transformation (including in planta transformation), protoplast fusion, or electroporation, amongst others. Most preferably the plant is produced by *Agrobacterium*-mediated transformation. *Agrobacterium*-mediated transformation or agrolistic transformation of plants, yeast, moulds or filamentous fungi is based on the transfer of part of the transformation vector sequences, called the T-DNA, to the nucleus and on integration of said T-DNA in the genome of said eukaryote.

The term "*Agrobacterium*" as used herein, includes a member of the Agrobacteriaceae, more preferably *Agrobacterium* or Rhizobacterium and most preferably *Agrobacterium tumefaciens*.

The term "T-DNA", or "transferred DNA", as used herein, includes the transformation vector flanked by T-DNA borders which is, after activation of the *Agrobacterium* vir genes, nicked at the T-DNA borders and is transferred as a single stranded DNA to the nucleus of an eukaryotic cell.

As used herein, the terms "T-DNA borders", "T-DNA border region", or "border region" include either right T-DNA borders (RB) or left T-DNA borders (LB), which comprise a core sequence flanked by a border inner region as part of the T-DNA flanking the border and/or a border outer region as part of the vector backbone flanking the border. The core sequences comprise 22 bp in case of octopine-type vectors and 25 bp in case of nopaline-type vectors. The core sequences in the right border region and left border region form imperfect repeats. Border core sequences are indispensable for recognition and processing by the *Agrobacterium* nicking complex consisting of at least VirD1 and VirD2. Core sequences flanking a T-DNA are sufficient to promote transfer of the T-DNA As used herein, the term "T-DNA transformation vector" or "T-DNA vector" includes any vector encompassing a T-DNA sequence flanked by a right and left T-DNA border consisting of at least the right and left border core sequences, respectively, and used for transformation of any eukaryotic cell.

As used herein, the term "T-DNA vector backbone sequence" or "T-DNA vector backbone sequences" includes all DNA of a T-DNA containing vector that lies outside of the T-DNA borders and, more specifically, outside the nicking sites of the border core imperfect repeats.

The present invention includes optimized T-DNA vectors such that vector backbone integration in the genome of a eukaryotic cell is minimized or absent. The term "optimized T-DNA vector" as used herein includes a T-DNA vector designed either to decrease or abolish transfer of vector backbone sequences to the genome of a eukaryotic cell. Such T-DNA vectors are known to the one of skill in the art and include those described by Hanson et al. (1999) *Plant J.* 19:727-734, by Stuiver et al. (1999—WO9901563) and by Depicker et al. (2001—WO0144482).

The current invention clearly considers the inclusion of a DNA sequence encoding an ICK, homologue, analogue, derivative or immunologically active fragment thereof as defined supra, in any T-DNA vector comprising binary transformation vectors, super-binary transformation vectors, co-integrate transformation vectors, Ri-derived transformation vectors as well as in T-DNA carrying vectors used in agrolistic transformation.

As used herein, the term "binary transformation vector" includes a T-DNA transformation vector comprising: a T-DNA region comprising at least one gene of interest and/or at least one selectable marker active in the eukaryotic cell to be transformed; and a vector backbone region comprising at least origins of replication active in *E. coli* and *Agrobacterium* and markers for selection in *E. coli* and *Agrobacterium*.

The T-DNA borders of a binary transformation vector can be derived from octopine-type or nopaline-type Ti plasmids or from both. The T-DNA of a binary vector is only transferred to a eukaryotic cell in conjunction with a helper plasmid. As used herein, the term "helper plasmid" includes a plasmid that is stably maintained in *Agrobacterium* and is at least carrying the set of vir genes necessary for enabling transfer of the T-DNA. The set of vir genes can be derived from either octopine-type or nopaline-type Ti plasmids or from both.

As used herein, the term "super-binary transformation vector" includes a binary transformation vector additionally carrying in the vector backbone region a vir region of the Ti plasmid pTiBo542 of the super-virulent *A. tumefaciens* strain A281 (EP0604662, EP0687730). Super-binary transformation vectors are used in conjunction with a helper plasmid.

As used herein, the term "co-integrate transformation vector" includes a T-DNA vector at least comprising: a T-DNA region comprising at least one gene of interest and/or at least one selectable marker active in plants; and a vector backbone region comprising at least origins of replication active in *Escherichia coli* and *Agrobacterium*, and markers for selection in *E. coli* and *Agrobacterium*, and a set of vir genes necessary for enabling transfer of the T-DNA. The T-DNA borders and the set of vir genes of the T-DNA vector can be derived from either octopine-type or nopaline-type Ti plasmids or from both.

The term "Ri-derived plant transformation vector" includes a binary transformation vector in which the T-DNA borders are derived from a Ti plasmid and the binary transformation vector being used in conjunction with a 'helper' Ri-plasmid carrying the necessary set of vir genes.

The terms "agrolistics", "agrolistic transformation" or "agrolistic transfer" include a transformation method combining features of *Agrobacterium*-mediated transformation and of biolistic DNA delivery. As such, a T-DNA containing target plasmid is co-delivered with DNA/RNA enabling in planta production of VirD1 and VirD2 with or without VirE2 (Hansen and Chilton (1996) *Proc. Natl. Acad Sci. U.S.A* 93:14978-14983; Hansen et al. (1997) *Proc. Natl. Acad. Sci. U.S.A.* 94:111726-11730; Hansen and Chilton (1997)-WO9712046).

A host cell of the invention, such as a prokaryotic or eukaryotic host cell in culture, can be used to produce (i.e., express) an ICK protein. Accordingly, the invention further provides methods for producing an ICK protein using the host cells of the invention. In one embodiment, the method comprises culturing the host cell of invention (into which a recombinant expression vector encoding an ICK protein has been introduced) in a suitable medium such that an ICK protein is produced. In another embodiment, the method further comprises isolating an ICK protein from the medium or the host cell.

The host cells of the invention can also be used to produce transgenic plant or non-human transgenic animals in which exogenous ICK sequences have been introduced into their genome or homologous recombinant plants or animals in which endogenous ICK sequences have been altered. Such plants and animals are useful for studying the function and/or activity of an ICK and for identifying and/or evaluating modulators of ICK activity.

Trangenic Plants

As used herein, "transgenic plant" includes a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses as asexual propagation from the initial transgenic. The term "transgenic" as used herein does not encompass the alteration of the genome (chromosomal or extra-chromosomal) by conventional plant breeding methods or by naturally occurring event such as random cross-fertilization, non-recombinant viral infection, non-recombinant bacterial transformation, non-recombinant transposition, or spontaneous mutation.

A transgenic plant of the invention can be created by introducing an ICK-encoding nucleic acid into the plant by placing it under the control of regulatory elements which ensure the expression in plant cells. These regulatory elements may be heterologous or homologous with respect to the nucleic acid molecule to be expressed as well with respect to the plant species to be transformed. In general, such regulatory elements comprise a promoter active in plant cells. These promoters can be used to modulate (e.g. increase or decrease) ICK content and/or composition in a desired tissue. To obtain expression in all tissues of a transgenic plant, preferably constitutive promoters are used, such as the 35 S promoter of CaMV (Odell, Nature 313 (1985), 810-812) or promoters from such genes as rice actin (McElroy et al. (1990) Plant Cell 2:163-171) maize H3 histone (Lepetit et al. (1992) Mol. Gen. Genet 231:276-285) or promoters of the polyubiquitin genes of maize (Christensen, Plant Mol. Biol. 18 (1982), 675-689). In order to achieve expression in specific tissues of a transgenic plant it is possible to use tissue specific promoters (see, e.g., Stockhaus, EMBO J. 8 (1989), 2245-2251 or Table 5, below).

TABLE 5

| GENE SOURCE | EXPRESSION PATTERN | REFERENCE |
|---|---|---|
| I: CELL-SPECIFIC, TISSUE-SPECIFIC, AND ORGAN-SPECIFIC PROMOTERS | | |
| α-amylase (Amy32b) | aleurone | Lanahan et al, Plant Cell 4:203-211, 1992; Skriver et al, Proc Natl Acad Sci USA 88:7266-7270, 1991 |
| cathepsin β-like gene | aleurone | Cejudo et al, Plant Mol Biol 20:849-856, 1992 |
| Agrobacterium rhizogenes rolB | camblum | Nilsson et al, Physiol Plant 100:456-462, 1997 |
| AtPRP4 | flowers | http://salus.medium.edu/mmg/tierney/html |
| chalcone synthase (chsA) | flowers | Van der Meer et al, Plant Mol Biol 15:95-109, 1990 |
| LAT52 | anther | Twell et al, Mol Gen Genet 217:240-245, 1989 |
| apetala-3 | flowers | |
| chitinase | fruit (berries, grapes, etc) | Thomas et al. CSIRO Plant Industry, Urrbrae, South Australia, Australia; http://winetitles.com.au/gwrdc/csh95-1.html |
| rbcs-3A | green tissue (eg leaf) | Lam et al, Plant Cell 2:857-866, 1990; Tucker et al., Plant Physiol 113:1303-1308, 1992 |
| leaf-specific genes | leaf | Baszczynski et al, Nucl Acid Res 16:4732, 1988 |
| AtPRP4 | leaf | http://salus.medium.edu/mmg/tierney/html |
| chlorella virus adenine methyltransferase gene promoter | leaf | Mitra and Higgins, Plant Mol Biol 26:85-93, 1994 |
| aldP gene promoter from rice | leaf | Kagaya et al, Mol Gen Genet 248:668-674, 1995 |
| rbcs promoter from rice or tomato | leaf | Kyozuka et al, Plant Physiol 102:991-1000, 1993 |
| Pinus cab-6 | leaf | Yamamoto et al, Plant Cell Physiol 35:773-778, 1994 |

TABLE 5-continued

| GENE SOURCE | EXPRESSION PATTERN | REFERENCE |
|---|---|---|
| rubisco promoter | leaf | |
| cab (chlorophyll a/b/binding protein | leaf | |
| pea Blec4 gene | vegetative and floral epidermal tissues | Mandaci and Dobres, Plant Mol Biol 34:961-965 |
| SAM22 | senescent leaf | Crowell et al, Plant Mol Biol 18:459-466, 1992 |
| ltp gene (lipid transfer gene) | | Fleming et al, Plant J 2:855-862, 1992 |
| R. japonicum nif gene | nodule | U.S. Pat. No. 4,803,165 |
| B. japonicum nifH gene | nodule | U.S. Pat. No. 5,008,194 |
| GmENOD40 | nodule | Yang et al, Plant J 3:573-585, 1993 |
| PEP carboxylase (PEPC) | nodule | Pathirana et al, Plant Mol Biol 20:437-450, 1992 |
| leghaemoglobin (Lb) | nodule | Gordon et al, J Exp Bot 44:1453-1465, 1993 |
| Tungro bacilliform virus gene | phloem | Bhattacharyya-Pakrasi et al, Plant J 4:71-79, 1992 |
| pollen-specific genes | pollen; microspore | Albani et al, Plant Mol Biol 15:605, 1990; Albani et al, Plant Mol Biol 16:501, 1991 |
| Zm13 | pollen | Guerrero et al, Mol Gen Genet 224:161-168, 1993 |
| apg gene | microspore | Twell et al, Sex Plant Reprod 6:217-224, 1993 |
| maize pollen-specific gene | pollen | Hamilton et al, Plant Mol Biol 18:211-218, 1992 |
| sunflower pollen-expressed gene | pollen | Baltz et al, Plant J 2:713-721, 1992 |
| B. napus pollen-specific gene | pollen; anther; tapetum | Amoldo et al, J Cell Biochem, Abstract No. Y101, 204, 1992 |
| root-expressible genes | roots | Tingey et al, EMBO J 6:1, 1987 |
| tobacco auxin-inducible gene | root tip | Van der Zaal et al, Plant Mol Biol 16:983, 1991 |
| β-tubulin | root | Oppenheimer et al, Gene 63:87, 1988 |
| tobacco root-specific genes | root | Conkling et al, Plant Physiol 93:1203, 1990 |
| B. napus G1-3b gene | root | U.S. Pat. No. 5,401,836 |
| SbPRP1 | roots | Suzuki et al, Plant Mol Biol 21:109-119, 1993 |
| AtPRP1; AtPRP3 | roots; root hairs | http://salus.medium.edu/mmg/tierney/html |
| RD2 gene | root cortex | http://2.cnsu.edu/ncsu/research |
| TobRB7 gene | root vasculature | http://2.cnsu.edu/ncsu/research |
| AtPRP4 | leaves; flowers; lateral root primordia | http://salus.medium.edu/mmg/tierney/html |
| seed-specific genes | seed | Simon et al, Plant Mol Biol 5:191, 1985; Scofield et al, J Biol Chem 262:12202, 1987; Baszczynski et al, Plant Mol Biol 14:633, 1990 |
| Brazil Nut albumin | seed | Pearson et al, Plant Mol Biol 18:235-245, 1992 |
| legumin | seed | Ellis et al, Plant Mol Biol 10:203-214, 1988 |
| glutelin (rice) | seed | Takaiwa et al, Mol Gen Genet 208:15-22, 1986; Takaiwa et al, FEBS Lett 221:43-47, 1987 |
| zein | seed | Matzke et al, Plant Mol Biol 14:323-32 1990 |
| napA | seed | Stalberg et al, Planta 199:515-519, 1996 |
| wheat LMW and HMW glutenin-1 | endosperm | Mol Gen Genet 216:81-90, 1989; Nucl Acids Res 17:461-462, 1989 |
| wheat SPA | seed | Albanl et al, Plant Cell 9:171-184, 1997 |

TABLE 5-continued

| GENE SOURCE | EXPRESSION PATTERN | REFERENCE |
|---|---|---|
| cZ19B1, maize 19 kDa zein | seed | WO0011177 |
| ml1ps, maize myoinositol-1-Pi synthase | seed | WO0011177 |
| wheat α, β, γ-gliadins | endosperm | EMBO J 3:1409-1415, 1984 |
| barley ltr1 promoter | endosperm | |
| barley B1, C, D, hordein | endosperm | Theor Appl Gen 98:1253-1262, 1999; Plant J 4:343-355, 1993; Mol Gen Genet 250:750-60, 1996 |
| barley DOF | endosperm | Mena et al, Plant J 116:53-62, 1998 |
| blz2 | endosperm | EP99106056.7 |
| synthetic promoter | endosperm | Vicente-Carbajosa et al, Plant J 13:629-640, 1998 |
| rice prolamin NRP33 | endosperm | Wu et al, Plant Cell Physiol 39:885-889, 1998 |
| rice α-globulin Glb-1 | endosperm | Wu et al, Plant Cell Physiol 39:885-889, 1998 |
| maize END genes | endosperm | WO0012733 |
| barley END1 | endosperm | WO9808961 |
| barley NUC1 | nucellus | WO9808961 |
| rice OSH1 | embryo | Sato et al, Proc Natl Acad Sci USA 93:8117-8122, 1996 |
| rice α-globulin REB/OHP-1 | endosperm | Nakase et al, Plant Mol Biol 33:513-522, 1997 |
| rice ADP-glucose PP | endosperm | Trans Res 6:157-168, 1997 |
| maize ESR gene family | endosperm | Plant J 12:235-246, 1997 |
| sorgum γ-kafirin | endosperm | Plant Mol Biol 32:1029-1035, 1996 |
| KNOX | embryo | Postma-Haarsma et al, Plant Mol Biol 39:257-271, 1999 |
| rice oleosin | embryo and aleuron | Wu et al, J Biochem 123:386, 1998 |
| sunflower oleosin | seed (embryo and dry seed) | Cummins et al, Plant Mol Biol 19:873-876, 1992 |
| LEAFY | shoot meristem | Weigel et al, Cell 69:843-859, 1992 |
| *Arabidopsis thaliana* knat1 | shoot meristem | Accession number AJ131822 |
| *Malus domestica* kn1 | shoot meristem | Accession number Z71981 |
| CLAVATA1 | shoot meristem | Accession number AF049870 |
| stigma-specific genes | stigma | Nasrallah et al, Proc Natl Acad Sci USA 85:5551, 1988; Trick et al, Plant Mol Biol 15:203, 1990 |
| class I patatin gene | tuber | Liu et al, Plant Mol Biol 153:386-395, 1991 |
| PCNA rice | meristem | Kosugi et al, Nucl Acids Res 19:1571-1576, 1991; Kosugi and Ohashi, Plant Cell 9:1607-1619, 1997 |
| Pea TubA1 tubulin | Dividing cells | Stotz and Long, Plant Mol Biol 41:601-614, 1999 |
| *Arabidopsis* cdc2a | cycling cells | Chung and Parish, FEBS Lett 362:215-219, 1995 |
| *Arabidopsis* Rop1A | Anthers; mature pollen + pollen tubes | Li et al, Plant Physiol 118:407-417, 1998 |
| *Arabidopsis* AtDMC1 | Meiosis-associated | Klimyuk and Jones, Plant J 11:1-14, 1997 |
| Pea PS-IAA4/5 and PS-IAA6 | Auxin-inducible | Wong et al, Plant J 9:587-599, 1996 |
| Pea farnesyltransferase | Meristematic tissues; phloem near growing tissues; light- and sugar-repressed | Zhou et al, Plant J 12:921-930, 1997 |
| Tobacco (*N. sylvestris*) cyclin B1;1 | Dividing cells/ meristematic tissue | Trehin et al, Plant Mol.Biol. 35:667-672, 1997 |
| *Catharanthus roseus* Mitotic cyclins CYS (A-type) and CYM (B-type) | Dividing cells/ meristematic tissue | Ito et al, Plant J 11:983-992, 1997 |
| *Arabidopsis* cyc1At (=cyc B1;1) and cyc3eAt (A-type) | Dividing cells/ meristematic tissue | Shaul et al, Proc Natl Acad Sci USA 93:4868-4872, 1996 |
| *Arabidopsis* tef1 promoter box | Dividing cells/ meristematic tissue | Regad et al, Mol Gen Genet 248:703-711, 1995 |
| *Catharanthus roseus* cyc07 | Dividing cells/ meristematic tissue | Ito et al, Plant Mol Biol 24:863-878, 1994 |
| II: CONSTITUTIVE PROMOTERS | | |
| Actin | constitutive | McElroy et al, Plant Cell 2:163-171, 1990 |
| CAMV 35S | constitutive | Odell et al, Nature 313:810-812, 1985 |
| CaMV 19S | constitutive | Nilsson et al, Physiol Plant 100:456-462, 1997 |
| GOS2 | constitutive | de Pater et al, Plant J 2:837-844, 1992 |
| ubiquitin | constitutive | Christensen et al, Plant Mol Biol 18:675-689, 1992 |
| rice cyclophilin | constitutive | Buchholz et al, Plant Mol Biol 26:837-843, 1994 |
| maize histone H3 | constitutive | Lepetit et al, Mol Gen Genet 231:276-285, 1992 |
| alfalfa histone H3 | constitutive | Wu et al, Nucleic Acids Res 17:3057-3063, 1989; Wu et al, Plant Mol Biol 11:641-649, 1988 |
| actin 2 | constitutive | An et al, Plant J 10:107-121, 1996 |
| III: STRESS-INDUCIBLE PROMOTERS | | |
| P5CS (delta(1)-pyrroline-5-carboxylate syntase) | salt, water | Zhang et al, Plant Sci 129:81-89, 1997 |
| cor15a | cold | Hajela et al, Plant Physiol 93:1246-1252, 1990 |
| cor15b | cold | Wlihelm et al, Plant Mol Biol 23:1073-1077, 1993 |
| cor15a (−305 to +78 nt) | cold, drought | Baker et al, Plant Mol Biol 24:01-713, 1994 |
| rd29 | salt, drought, cold | Kasuga et al, Nature Biotechnol 18:287-291, 1999 |
| heat shock proteins, including artificial promoters containing the heat shock element (HSE) | heat | Barros et al, Plant Mol Biol 19 665-75, 1992. Marrs et al, Dev Genet14:27-41, 1993. Schoffl et al, Mol Gen Genet 217:246-53, 1989. |
| smHSP (small heat shock proteins) | heat | Waters et al, J Exp Bot 47:325-338, 1996 |
| wcs120 | cold | Ouellete et al, FEBS Lett 423:324-328, 1998 |
| ci7 | cold | Kirch et al, Plant Mol Biol 33:897-909, 1997 |
| Adh | cold, drought, hypoxia | Dolferus et al, Plant Physiol 105:1075-87, 1994 |
| pwsi18 | water: salt and drought | Joshee et al, Plant Cell Physiol 39:64-72, 1998 |
| ci21A | cold | Schneider et al, Plant Physiol 113:335-45, 1997 |
| Trg-31 | drought | Chaudhary et al, Plant Mol Biol 30:1247-57, 1996 |
| Osmotin | osmotic | Raghothama et al, Plant Mol Biol 23:1117-28, 1993 |

TABLE 5-continued

| GENE SOURCE | EXPRESSION PATTERN | REFERENCE |
|---|---|---|
| LapA | wounding, enviromental | WO99/03977 University of California/INRA |
| IV: PATHOGEN-INDUCIBLE PROMOTERS | | |
| RB7 | Root-knot nematodes (*Meloidogyne* spp.) | U.S. Pat. No. 5,760,386 - North Carolina State University; Opperman et al, Science 263:221-23, 1994 |
| PR-1, 2, 3, 4, 5, 8, 11 | fungal, viral, bacterial | Ward et al, Plant Cell 3:1085-1094, 1991; Reiss et al 1996; Lebel et al, Plant J 16:223-233, 1998; Melchers et al, Plant J 5:469-480, 1994; Lawton et al, Plant Mol Biol, 19:735-743, 1992 |
| HMG2 | nematodes | WO9503690 - Virginia Tech Intellectual Properties Inc. |
| Abi3 | Cyst nematodes (*Heterodera* spp.) | unpublished |
| ARM1 | nematodes | Barthels et al, Plant Cell 9:2119-2134, 1997 WO 98/31822 - Plant Genetic Systems |
| Att0728 | nematodes | Barthels et al, Plant Cell 9:2119-2134, 1997 PCT/EP98/07761 |
| Att1712 | nematodes | Barthels et al, Plant Cell 9,2119-2134, 1997 PCT/EP98/07761 |
| Gst1 | Different types of pathogens | Strittmatter et al, Mol Plant-Microbe Interact 9:68-73, 1996 |
| LEMMI | nematodes | WO 92/21757 - Plant Genetic Systems |
| CLE | geminivirus | PCT/EP99/03445 - CINESTAV |
| PDF1.2 | Fungal including *Alternaria brassicicola* and *Botrytis cinerea* | Manners et al, Plant Mol Biol, 38:1071-1080, 1998 |
| Thi2.1 | Fungal-*Fusarium oxysporum* f sp. *matthiolae* | Vignutelli et al, Plant J 14:285-295, 1998 |
| DB#226 | nematodes | Bird and Wilson, Mol Plant-Microbe Interact 7:419-442, 1994 WO 95.322888 |
| DB#280 | nematodes | Bird and Wilson, Mol Plant-Microbe Interact 7:419-442, 1994 WO 95.322888 |
| Cat2 | nematodes | Niebel et al, Mol Plant-Microbe Interact 8:371-378, 1995 |
| □Tub | nematodes | Aristizabal et al (1996), 8$^{th}$ International Congress on Plant-Microbe Interaction, Knoxville US B-29 |
| sHSP | nematodes | Fenoll et al (1997) in: Cellular and molecular aspects of plant-nematode interactions. Kluwer Academic, C. Fenoll, F. M. W. Grundler and S. A. Ohl (Eds.), |
| Tsw12 | nematodes | Fenoll et al (1997) in: Cellular and molecular aspects of plant-nematode interactions. Kluwer Academic, C. Fenoll, F. M. W. Grundler and S. A. Ohl (Eds.), |
| Hs1(pro1) | nematodes | WO 98/122335 - Jung |
| nsLTP | viral, fungal, bacterial | Molina and Garcia-Olmedo FEBS Lett, 316:119-122, 1993 |
| RIP | viral, fungal | Turner et al, Proc Natl Acad Sci USA 94:3866-3871, 1997 |

The promoters listed in the foregoing table are provided for the purposes of exemplification only and the present invention is not to be limited by the list provided therein. Those skilled in the art will readily be in a position to provide additional promoters that are useful in performing the present invention. The promoters listed may also be modified to provide specificity of expression as required.

Known are also promoters which are specifically active in tubers of potatoes or in seeds of different plants species, such as maize, *Vicia*, wheat, barley and the like. Inducible promoters may be used in order to be able to exactly control expression under certain environmental or developmental conditions such as pathogens, anaerobia, or light. Examples of inducible promoters include the promoters of genes encoding heat shock proteins or microspore-specific regulatory elements (WO96/16182). Furthermore, the chemically inducible Tet-system may be employed (Gatz, Mol. Gen. Genet 227 (1991); 229-237). Further suitable promoters are known to the person skilled in the art and are described, e.g., in Ward (Plant Mol. Biol. 22 (1993), 361-366). The regulatory elements may further comprise transcriptional and/or translational enhancers functional in plants cells. Furthermore, the regulatory elements may include transcription termination signals, such as a poly-A signal, which lead to the addition of a poly A tail to the transcript which may improve its stability.

In the case that a nucleic acid molecule according to the invention is expressed in the sense orientation, the coding sequence can be modified such that the protein is located in any desired compartment of the plant cell, e.g., the nucleus, endoplasmatic reticulum, the vacuole, the mitochondria, the plastids, the apoplast, or the cytoplasm.

Methods for the introduction of foreign DNA into plants are also well known in the art. These include, for example, the transformation of plant cells or tissues with T-DNA using *Agrobacterium tumefaciens* or *Agrobacterium rhizogenes*, the fusion of protoplasts, direct gene transfer (see, e.g., EP-A 164 575), injection, electroporation, biolistic methods like particle bombardment, pollen-mediated transformation, plant RNA virus-mediated transformation, liposome-mediated transformation, transformation using wounded or enzyme-degraded immature embryos, or wounded or enzyme-degraded embryogenic callus and other methods known in the art. The vectors used in the method of the invention may contain further functional elements, for example "left border"- and "right border"-sequences of the T-DNA of *Agrobacterium* which allow for stably integration into the plant genome. Furthermore, methods and vectors are known to the person skilled in the art which permit the generation of marker free transgenic plants, i.e., the selectable or scorable marker gene is lost at a certain stage of plant development or plant breeding. This can be achieved by, for example, cotransformation (Lyznik, Plant Mol. Biol. 13 (1989), 151-161; Peng, Plant Mol. Biol. 27 (1995), 91-104) and/or by using systems which utilize enzymes capable of promoting homologous recombination in plants (see, e.g., WO97/08331; Bayley, Plant Mol. Biol. 18 (1992), 353-361); Lloyd, Mol. Gen. Genet. 242 (1994), 653-657; Maeser, Mol. Gen. Genet. 230 (1991), 170-176; Onouchi, Nucl. Acids Res. 19 (1991), 6373-6378). Methods for the preparation of appropriate vectors are described by, e.g., Sambrook (Molecular Cloning; A Laboratory Manual, 2nd Edition (1989), Cold Spring Harbor Laboratory Press, Cold Spring Harbor, N.Y.).

Suitable strains of *Agrobacterium tumefaciens* and vectors, as well as transformation of Agrobacteria, and appropriate growth and selection media are described in, for example, GV3101 (pMK90RK), Koncz, Mol. Gen. Genet. 204 (1986), 383-396; C58C1 (pGV 3850kan), Deblaere, Nucl. Acid Res. 13 (1985), 4777; Bevan, Nucleic. Acid Res. 12(1984), 8711; Koncz, Proc. Natl. Acad. Sci. USA 86 (1989), 8467-8471; Koncz, Plant Mol. Biol. 20 (1992), 963-976; Koncz, Specialized vectors for gene tagging and expression studies. In: Plant Molecular Biology Manual Vol 2, Gelvin and Schilperoort (Eds.), Dordrecht, The Netherlands: Kluwer Academic Publ. (1994), 1-22; EP-A-120 516; Hoekema: The Binary Plant Vector System, Offsetdrukkerij Kanters B. V., Alblasserdam (1985), Chapter V, Fraley, Crit. Rev. Plant. Sci., 4, 1-46; An, EMBO J. 4 (1985), 277-287). Although the use of *Agrobacterium tumefaciens* is preferred in the method of the invention, other *Agrobacterium* strains, such as *Agrobacterium rhizogenes*, may be used, for example, if a phenotype conferred by said strain is desired.

Methods for the transformation using biolistic methods are known to the person skilled in the art; see, e.g., Wan, Plant Physiol. 104 (1994), 37-48; Vasil, Bio/Technology 11 (1993), 1553-1558 and Christou (1996) Trends in Plant Science 1, 423-431. Microinjection can be performed as described in Potrykus and Spangenberg (eds.), Gene Transfer To Plants. Springer Verlag, Berlin, N.Y. (1995).

The transformation of most dicotyledonous plants may be performed using the methods described above or using transformation via biolistic methods as, e.g. described above as well as protoplast transformation, electroporation of partially permeabilized cells, or introduction of DNA using glass fibers.

In general, the plants which are modified according to the invention may be derived from any desired plant species. They can be monocotyledonous plants or dicotyledonous plants, preferably they belong to plant species of interest in agriculture, wood culture or horticulture interest, such as crop plants (e.g., maize, rice, barley, wheat, rye, oats), potatoes, oil producing plants (e.g., oilseed rape, sunflower, pea nut, soy bean), cotton, sugar beet, sugar cane, leguminous plants (e.g., beans, peas), or wood producing plants, preferably trees.

The present invention also relates to a transgenic plant cell which contains (preferably stably integrated into its genome) a nucleic acid molecule of the present invention linked to regulatory elements which allow expression of the nucleic acid molecule in plant cells. The presence and expression of the nucleic acid molecule in the transgenic plant cells leads to the synthesis of an ICK protein and may lead to physiological and phenotypic changes in plants containing such cells.

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker which has been introduced with a polynucleotide of the present invention.

Plant cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture*, Macmiliilan Publishing Company, New York, pp. 124-176 (1983); and *Binding, Regeneration of Plants, Plant Protoplasts*, CRC Press, Boca Raton, pp. 21-73 (1985).

Transformed plant cells, calli or explant can be cultured on regeneration medium in the dark for several weeks, generally about 1 to 3 weeks to allow the somatic embryos to mature. Preferred regeneration media include media containing MS salts, such as PHI-E and PHI-F media. The plant cells, calli or explant are then typically cultured on rooting medium in a light/dark cycle until shoots and roots develop. Methods for plant regeneration are known in the art and preferred methods are provided by Kamo et al, (*Bot. Gaz.* 146(3):324-334, 1985), West et al, (*The Plant Cell* 5:1361-1369. 1993), and Duncan et al. (*Planta* 165:322-332, 1985).

Small plantlets can then be transferred to tubes containing rooting medium and allowed to grow and develop more roots for approximately another week. The plants can then be transplanted to soil mixture in pots in the greenhouse.

The regeneration of plants containing the foreign gene introduced by *Agrobacterium* from leaft explants can be achieved as described by Horsch et al., *Science,* 227:1229-1231 (1985). In this procedure, transformants are grown in the presence of a selection agent and in a medium that induces the regeneration of shoots in the plant species being transformed as described by Fraley et al., *Proc. Natl. Acad. Sci, USA.* 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.,* 38:467-486 (1987). The regeneration of plants from either single plant protoplasts or various explants is well known in the art. See, from example, *Methods for Plant Molecular Biology*, A. Weissbach and H. Weissback, eds., Academic Press, Inc., San Diego, Calif. (1988). This regeneration and growth process includes the steps of selection of transformant cells and shoots, rooting ht transformant shoots and growth of the plantlets in soil. For maize cell culture and regeneration see generally, *The Maize Handbook*, Freeling and Walbot, Eds., Springer, New York (1994); *Corn and Corn Improvement,* 3rd edition, Sprague and Dudley Eds., American Society of Agronomy, Madison, Wis. (1988).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype, (e.g., altered cell cycle content or composition).

Parts obtained from the regenerated plant, such as flowers, seeds, leaves, branches, fruit and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing the selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment of the invention is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered cell division relative to a control plant (i.e., native, non-transgenic). Back-crossing to a parental plant and out-crossing with a non-transgenic plant are also contemplated.

The present invention also relates to transgenic plants and plant tissue comprising transgenic plant cells according to the invention. Due to the (over)expression of an ICK molecule, e.g., at developmental stages and/or in plant tissue in which they do not naturally occur, these transgenic plants may show various physiological, developmental and/or morphological modifications in comparison to wild-type plants.

Therefore, part of this invention is the use of the ICK molecules to modulate the cell cycle and/or plant cell division and/or growth in plant cells, plant tissues, plant organs and/or whole plants. To the scope of the invention also belongs a method for influencing the activity of cell cycle control proteins such as CDKs and cyclins in a plant cell by transforming the plant cell with a nucleic acid molecule according to the invention and/or manipulation of the expression of the molecule.

Furthermore, the invention also relates to a transgenic plant cell which contains (preferably stably integrated into its genome) a nucleic acid molecule of the invention or part thereof, wherein the transcription and/or expression of the nucleic acid molecule or part thereof leads to reduction of the synthesis of an ICK. In a preferred embodiment, the reduction is achieved by an anti-sense, sense, ribozyme, co-suppression and/or dominant mutant effect. The reduction of the synthesis of a protein according to the invention in the transgenic plant cells can result in an alteration in, e.g., cell division. In transgenic plants comprising such cells this can lead to various physiological, developmental and/or morphological changes.

In yet another aspect, the invention relates to harvestable parts and to propagation material of the transgenic plants of the invention which either contain transgenic plant cells expressing a nucleic acid molecule according to the invention or which contain cells which show a reduced level of the described protein. Harvestable parts can be in principle any useful parts of a plant, for example, flowers, pollen, seedlings, tubers, leaves, stems, fruit, seeds, roots etc. Propagation material includes, for example, seeds, fruits, cuttings, seedlings, tubers, rootstocks, and the like.

VI. Agricultural Compositions

The ICK nucleic acid molecules, ICK proteins, and anti-ICK antibodies (also referred to herein as "active compounds") of the invention can be incorporated into compositions useful in agriculture and in plant cell and tissue culture. Plant protection compositions can be prepared by conventional means commonly used for the application of, for example, herbicides and pesticides. For example, certain additives known to those skilled in the art stabilizers or substances which facilitate the uptake by the plant cell, plant tissue or plant may be used.

The agricultural compositions can be included in a container, pack, or dispenser together with instructions for administration.

This invention is further illustrated by the following examples which should not be construed as limiting. The contents of all references, patents and published patent applications cited throughout this application, as well as the Figures and the Sequence Listing are incorporated herein by reference.

EXAMPLES

Unless stated otherwise in the example, all recombinant DNA techniques are performed according to protocols as described in Sambrook et al. (1989), Molecular cloning: A Laboratory Manual. Cold Spring Harbor Laboratory Press, NY or in Ausubel et al. (1999) Current Protocols in Molecular Biology, CD-ROM, John Wiley & Sons, Inc, NY. Standard material and methods for plant molecular work are described in Plant Molecular Biology Labfase (1993) by R. D. D. Croy, jointly published by BIOS Scientific Publications Ltd (UK) and Blackwell Scientific Publications (UK).

Example 1

Construction of the Rice Two-Hybrid cDNA Library

For the identification of ICKs, a two-hybrid system based on Gal4 transcriptional activation was developed with the aim of identifying CDC2Os1-interacting proteins. Total RNA was extracted from cell suspension cultures harvested at 0, 3, 6, 9, and 12 days after subculturing in fresh medium. These time-points correspond to cells in the lag phase following subculture, the exponential growth, and the late stationary phase. Equimolar amounts of total RNA (5×100 µg) from the different fractions were then pooled. The total RNA sample was used to purify 5 µg of polyA+mRNA using the Poly(A) Quik mRNA Isolation kit (Stratagene), based on oligo(dT) cellulose columns. Synthesis and subcloning of the cDNA into the HybriZAP-2.1 lambda vector were performed according to the manufacturer's guidelines (Stratagene). Approximately 2 million independent plaque-forming units were produced, with an average insert size of 1.0 kb. Bank amplification and mass excision to obtain phagemids used to transform yeast were done following the same instruction manual.

The rice Cdc2-Os1 gene was amplified using the following primers (sense: 5'-AGGGATGTTTAATACCACTAC-3', SEQ ID NO:33 and antisense primer: 5'-GCACAGT-TGAAGTGAACTTGC-3', SEQ ID NO:34) and the Pfx DNA polymerase (Promega). The PCR fragment was blunt end cloned into the SmaI site of pBD-Gal4 (Stratagene) bait vector in frame with the binding domain. The bait vector was introduced in yeast PJ69-4a according to the "Quick and Easy TRAFO Protocol" (Gietz, R. D. and R. A. Woods, (1994) High Efficiency transformation in Yeast (Invited Book Chapter) In: Molecular Genetics of Yeast: Practical Approaches, ed. J. A. Johnston, Oxford University Press pp. 121-134) and the transformants selected on dropout medium lacking tryptophane. These transformants were confirmed by PCR using the above mentioned primers.

Using the yeast two-hybrid assay, a number of Cdc2Os1-interacting clones were identified. Surprisingly, however, none of these clones was an ICK.

The lambdaHybriZAP-2.1 (Stratagene, La Jolla, Calif.) two-hybrid cDNA library made from the rice suspension culture as outlined above was deposited on Oct. 27, 2000 with the 'Belgian co-ordinated collections of micro-organisms' (BCCM-LMBP, University Gent, Laboratorium voor Moleculaire Biologie, K. L. Ledeganckstraat 35, B-9000 Gent, Belgium) according to the regulations of the Budapest Treaty. BCCM is recognized by the WIPO as an IDA. The accession number of the deposit is LMBP4268).

Example 2

Molecular Cloning of ICK Fragments

To overcome the aforementioned problem, public sequence databases (available at, for example, http://www.ncbi.nlm.nih.gov, http://www.tigr.org) were screened for the "GRYEW" amino acid motif located at the carboxy-termini of all known plant ICKs, using the advanced BLAST program with a high expect value (1000).

Using the foregoing database mining approach, four hits were obtained in Oryza sativa, one EST (partial cDNA, GenBank accession number AU075786, SEQ ID NO:1, termed OsICK2), two GSS (partial genomic sequences, GenBank accession number AQ574895, SEQ ID NO:2, termed OsICK1 and GenBank accession number AQ365042, SEQ ID NO:3, termed OsICK3), and one HTGS (high throughput genomic sequences, GenBank accession number AC069145, SEQ ID NO:4, termed OsICK4), none of them annotated as encoding a putative ICK protein. Four additional unannotated clones, two Zea mays ESTs (GenBank accession number AI737717, SEQ ID NO:5, termed ZmICK1; and GenBank accession number AW267370, SEQ ID NO:6, termed ZmICK2) a Sorghum bicolor BAC genomic clone (GenBank accession number AF061282, SEQ ID NO:7, termed SbICK), and a Pinus taeda cDNA (GenBank accession number AA556411, SEQ ID NO:8, termed PtICK) were identified as plant ICKs.

The following Primers were designed to perform a PCR to amplify the identified fragments:

```
OsICK1 yielding a 178 bp DNA fragment:
5'-TAACTCGATCCCCAGCCTCTCCCA-3' and (SEQ ID NO: 25)

5'-TACAATTACGACATTGCCCTCGAC-3'      (SEQ ID NO: 26)

OsICK2 yielding a 430 bp fragment:
5'-CCGCCGAGATCGAGGCGTTCTTCG-3' and (SEQ ID NO: 27)

5'-AAACCTCTGATAAATACTGGGACG-3'      (SEQ ID NO: 28)

OsICK3 yielding a 200 bp fragment:
5'-CTGTCACACACTCACACTCACACT-3' and (SEQ ID NO: 29)

5'-CGAAGAACGCCTCGATCTCC-3'          (SEQ ID NO: 30)

OsICK4 yielding a 271 bp fragment:
5'-GAATACCAGGGAGACGACACCTTGC-3'     (SEQ ID NO: 31)

5'-TCAGTCTAGGTTGACCCATTCAAAC-3'     (SEQ ID NO: 32)
```

The two-hybrid bank (in the form of plasmid) was used to amplify all of these fragments, which were then subcloned into the pUC18 SmaI site and transformed info E. coli following standard molecular biology techniques.

Example 3

Hybridization Screening of the Rice Two-Hybrid cDNA Library and Molecular Cloning of Full-Length OsICK2 cDNA Following plasmid purification from E. coli, the four fragments were isolated by restriction and gel-purified following art known techniques. The respective fragments were radioactively labelled with the aim to identify, via homologous hybridisation, the corresponding cDNAs in the two-hybrid library. Serial dilutions of a plasmid preparation (6 µg/µl) of the library was used as template for PCR amplification. For OsICK2, the 430 bp could be amplified until dilution 10-4. This dilution was used to transform XL-10 Gold (Stratagene) ultracompetent cells. Approximately 70,000 colonies were then screened with the labelled OsICK2 fragment. A number of putative positives colonies were re-screened via PCR using the OsICK2 primers. A total of 5 positive clones were finally obtained, one of which was further characterized. Sequencing of the insert indicated that this clone was indeed the OsICK2 fall length clone.

Example 4

Two Hybrid Screening and Hybridization Screening of the Rice Two-Hybrid cDNA Library and Molecular Cloning of Full-Length OsICK4 cDNA As described in Example 1, a first two-hybrid screening of the rice two-hybrid cDNA library using Cdc2-Os1 as bait did not yield any OsICKs as Cdc2-Os1 interactors. The two-hybrid screening was repeated in a second attempt to obtain OsICK clones via this methodology. In parallel, hybridization screening of the rice two-hybrid cDNA library was performed as described in Example 3 with the aim of obtaining a full-length OsICK4 cDNA.

Two-Hybrid Screening

Screening of a library prepared from an actively dividing rice cell suspension was accomplished by sequential transformation of yeast. PJ69-4a carrying pBD-cdc2Os-Gal4 was transformed with library DNA according to the protocol Matchmaker Two-Hybrid System (protocol#PT1020-1, version#PR4Y411) from CLONTECH Laboratories, Inc. After a library scale transformation (efficiency 17268 clones/µg DNA) a total number of 672 clones were recovered from selective medium (SD-TLH) lacking tryptophane, leucine and histidine. These clones were further selected on SD-TLA (lacking tryptophane, leucine and adenine) and SD-TLAH (lacking tryptophane, leucine, adenine and histidine). Nine clones were finally selected and sequenced. Among the nine clones a CDK inhibitor was identified which was a putative partial OsICK4 cDNA sequence missing the 5' end.

Hybridization Screening

Figure 10:
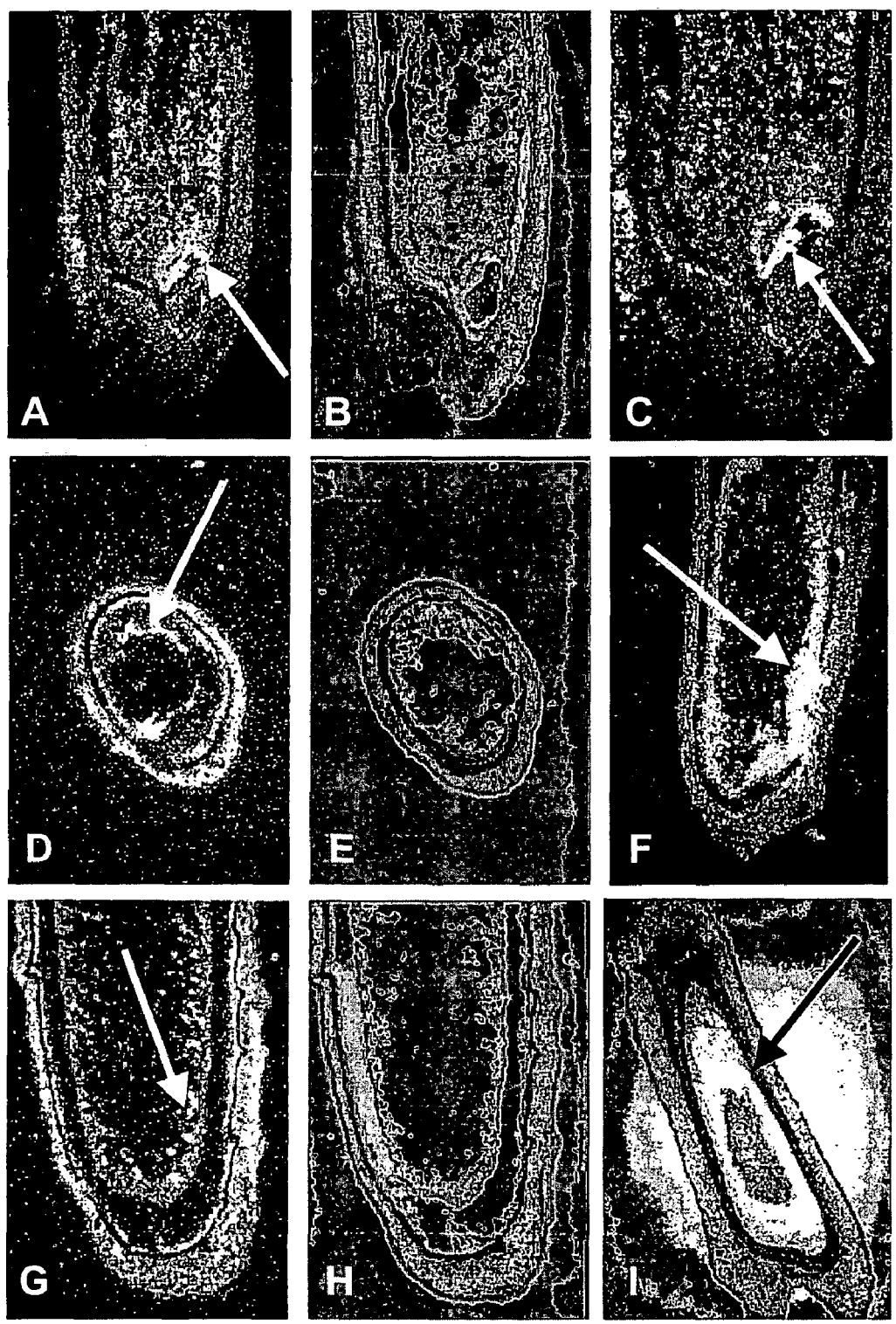
FIGS. 10A-I depicts the results from an in situ hybridization analysis of OsICK2 expression in rice seeds collected 20 days after pollination. (A) and (B) are dark field and bright field microscopic images, respectively, of the same longitudinal section. (C) is a magnification of a part of (A). Clearly visible is the (bright white) hybridization signal in the scutellum (white arrow). (D) and (E) are dark field and bright field microscopic images, respectively, of the same cross section. (F) is a magnification of a part of (D). Hybridization signals in (D) and (F) show expression of OsICK2 in the cell layer(s) lining the developing endosperm (white arrows). (G) and (H) are dark field and bright field microscopic images, respectively, of the same longitudinal section again showing OsICK2 expression in the cell layers surrounding the developing endosperm (white arrow). The same is shown in the bright field microscopic image (I) where the hybridization signal is black (black arrow).

The OsICK4 fragment cloned in pUC 18 as described in Example 2 was used to prepare a probe for the hybridization screening of the rice two-hybrid cDNA library. The primers with SEQ ID NO:31 and SEQ ID NO:32 (see Example 2) were used for this purpose. Approximately 750.000 plaque-forming units from the cell suspension two-hybrid cDNA library were screened. Plaques were transferred to Hybond N+ membranes (Amersham). The filters obtained were prehybridized in sodium phosphate 0.25M, (pH 7.2), SDS 7% at 60° C. for 4 hours. Hybridization was performed with the prehybridization buffer containing 50 ng of $[\alpha]^{32}$P-dCTP-labelled probe at 60° C. overnight (protocol of Church G. M. and Gilbert W. *PNAS USA* 81:1991-1994). The filters were washed twice with 1×SSC, 0.1% SDS at 60° C. for 30 minutes and then once with 0.1×SSC, 0.1% SDS at 60° C. for 30 minutes. The membranes were placed into a film cassette and exposed to film for 6 hours. Four clones were isolated. A second round of screening on these clones was performed. Pure positive plaques were isolated from which the phagemids were excised. Two clones were obtained for sequencing. One of them is a fill length clone with a size of 1.1 kb. This clone contains an ORF of 585 bp encoding a protein of 194 amino acids. This ORF comprises the partial OsICK4 nucleotide sequence as identified in the two-hybrid screening (supra; see FIG. 10).

Figure 18:
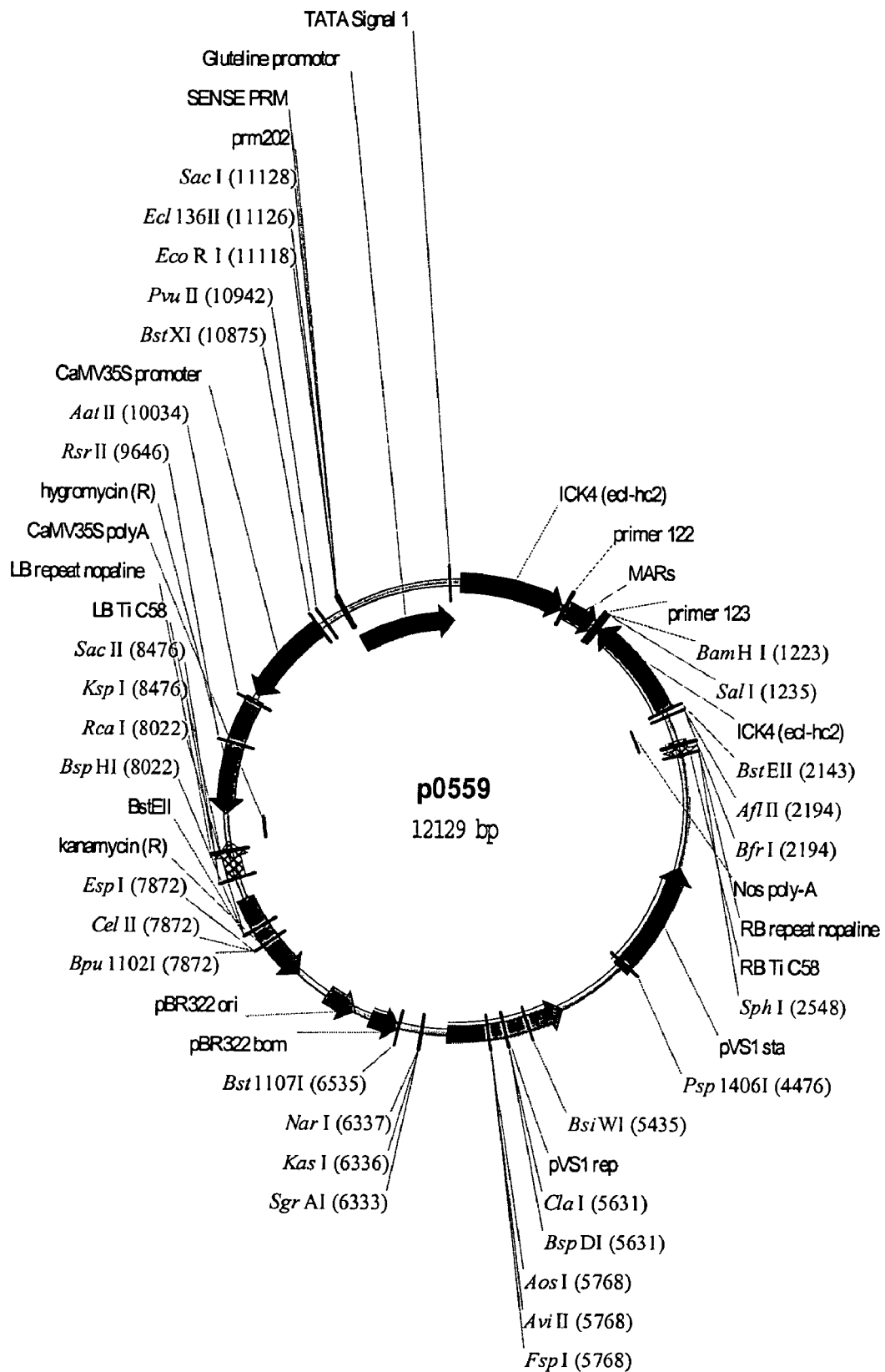
FIG. 18 depicts the binary plant transformation vector p0559 comprising the OsICK4 co-suppression cassette of pUC-ICK4 CS (see FIG. 13) operably linked to the gluteline promoter.

The nucleotide sequence of this full-length OsICK4 is depicted in FIG. 1B and set forth as SEQ ID NO:43. The amino acid sequence of this full-length OsICK4 is depicted in FIG. 11 and set forth as SEQ ID NO:44. The OsICK4 genomic sequence was also determined as is set forth herein in SEQ ID NO:45 and depicted in FIG. 18.

On Sep. 30, 2000, the fifth version of GenBank Accession Number AC069145 was released in GenBank. GenBank Accession Number AC069145 was previously identified by the inventors as containing a putative OsICK sequence (see Example 2). Contrary to previous versions, AC069145.5 now has the putative OsICK annotated as a putative cyclin-dependent kinase inhibitor identified by protein ID=AAG16867.1. The ORF prediction and, thus, the predicted protein sequence is, however, different from the cDNA and protein sequences experimentally determined by the present application. The OsICK protein predicted in GenBank (protein ID=AAG 16867.1) contains an insertion of 48 superfluous amino acids and is, therefore, almost certainly functionally inactive. The comparison of the GenBank predicted protein and the currently experimentally obtained protein is set forth herein in FIG. 11.

The current experiments also clearly demonstrate the physical interaction of the rice cyclin-dependent kinase Cdc2-Os1 with the rice cyclin-dependent kinase inhibitor OsICK4 as a partial clone of the latter was obtained via two-hybrid screening of a rice cDNA library. These data furthermore indicate that the NH$_2$-terminal 66 amino acids of the OsICK4 are apparently not required for interaction with Cdc2-Os1.

Example 5

Characterization of OsICK2 and OsICK4

As described in the preceding example, screening of the rice two-hybrid cDNA library resulted in the identification of the full length OsICK2 cDNA (SEQ ID NO:9) encoding a full-length rice OsICK2 protein (SEQ ID NO:10) and of the full length OsICK4 cDNA (SEQ ID NO:43) encoding a full-length rice OsICK4 protein (SEQ ID NO:44). The partial open reading frame of SEQ ID NO:1 encodes, when taking into account a frame shift at nucleotide 52 of SEQ ID NO:1, the carboxy-terminal part of the OsICK2 protein. When comparing the nucleotide sequences SEQ ID NO:1 and SEQ ID NO:9, however, a stretch of 104 nucleotides (nucleotides 1121-1224 in SEQ ID NO:9) can be discerned in the 3' untranslated region of SEQ ID NO:9 which are not present in SEQ ID NO:1 (see FIG. 1). This indicates that OsICK2 primary transcripts are prone to alternative polyadenylation site selection. A closer examination of the 3' untranslated region in SEQ ID NO:9 reveals the presence of two canonical mRNA polyadenylation sites (Edwards-Gilbert et al. 1997), namely AAUAAA (nucleotides 922-927 in SEQ ID NO:9) and AUUAAA (nucleotides 1156-1161 in SEQ ID NO:9). The second of these sites is not present in the 3' untranslated region of SEQ ID NO:1 which is consistent with the use of alternative polyadenylation sites in primary OsICK2 transcripts.

Another interesting feature of the 3' untranslated regions of the two different transcripts most likely derived from the same OsICK2 gene concerns class I AREs (AU-rich elements). Transcripts corresponding to SEQ ID NO:1 comprise one such ARE (AUUUA, nucleotides 419-423 in SEQ ID NO:1) whereas transcripts corresponding to SEQ ID NO:9 contain two AREs (AUUUA; nucleotides 1076-1080 and 1161-1165 in SEQ ID NO:9). A putative ARE is also present in the 3' untranslated region of OsICK4 (AUUUA; nucleotides 729-733 in SEQ ID NO:43). AREs are also present 3' relative to the stop codons in OsICK1 (stop codon 'TGA': nucleotides 154-156 of SEQ ID NO:2; ARE 'ATTTA': nucleotides 596-600, 600-604, 616-620 and 634-638 of SEQ ID NO:2); in ZmICK1 (stop codon 'TGA': nucleotides 350-352 of SEQ ID NO:5; ARE 'ATTTA': nucleotides 545-549 of SEQ ID NO:5) and in PtICK (stop codon 'TGA': nucleotides 161-163 of SEQ ID NO:8; ARE 'ATTTA': nucleotides 284-288 of SEQ ID NO:8). AREs are known to confer instability to an mRNA (Brewer 1991, Chen and Shiyu 1995, Malter 1989). AREs are furthermore recognized by HuR proteins, i.e., a ubiquitously expressed Elav protein family member.

Binding of HuR to AREs (and the poly-A-tail) enhances transcript stability (Fan and Steitz 1998). Interestingly, transcripts of the mammalian ICK p21Cip1 are stabilized upon UV-C irradiation of cells. Stabilization of p21Cip1 mRNA implies a HuR and increases p21Cip1 protein levels (Wang et al. 2000). p21Cip1 is known to enforce S-phase arrest upon the occurrence of DNA damage, e.g., as a result of UV irradiation (Chen et al. 1995). AREs are the target of Rnase E which is conserved from bacteria to humans. Importantly, mRNAs containing more than one ARE are cleaved more efficiently by Rnase E (Wennborg et al. 1995). Thus, the transcript corresponding to SEQ ID NO:9 may be degraded faster than the transcript corresponding to SEQ ID NO:1. Without wishing to be bound by theory or mode of action, a double function can be envisaged for OsICK2: a first function related to cell cycle control and implying rapid turnover of an unstable transcript and a second function related to differentiation (i.e., cell cycle withdrawal) and/or cell cycle arrest implying a transcript of higher stability. Alternatively, the opposite situation can be envisaged as transcript stability and translation efficiency can be positively or negatively correlated (Edwards-Gilbert et al. 1997 for review).

Another possibility for the regulation of OsICK2 function lies in the fact that alternative transcript polyadenylation can, as the skilled artisan will know, be tissue-specific and/or developmentally-specific and/or cell cycle-regulated (Edwards-Gilbert et al. 1997). Notable examples of cell cycle genes of which the transcripts are alternatively polyadenylated comprise dihydrofolate reductase (DHFR, required for DNA synthesis during S-phase and for DNA repair; Noé et al. 1999) and metazoan cyclin D1 (Kiyokawa et al. 1992, Xiong et al. 1991, Yarden et al. 1995). Alternation in DHFR transcript polyadenylation is moreover cell cycle-regulated (Noé et al. 1999). Changes in polyadenylation site usage in cyclin D1 occur during zebrafish embryonic development (Yarden et al. 1995). The polyadenylation process itself is also regulated by the cell cycle: the poly-A-polymerase (PAP) is inhibited by phosphorylation by mitosis-specific Cdc2-cyclin B complexes (Colgan et al. 1996) and PAP activity is increased in cells stimulated to enter the cell cycle (Benz et al. 1977, Coleman et al. 1997, Hauser et al. 1978). It will be clear to the skilled artisan that the above mentioned mechanisms of regulation of gene expression may also apply to OsICK4 gene expression.

The amino acid sequences of OsICK2 (SEQ ID NO:10) and OsICK4 (SEQ ID NO:44) were aligned with all full-length plant ICK amino acid sequences known in the art (see FIG. 2). The amino acid sequences of OsICK2 (SEQ ID NO:10) and OsICK4 (SEQ ID NO:44) were also aligned with the partial amino acid sequences of the other plant ICKs identified in the present invention: the partial amino acid sequence of OsICK1 (SEQ ID NO: 1, encoded by the nucleotide sequence of SEQ ID NO:2), the partial amino acid sequence of OsICK3 (SEQ ID NO: 12 encoded by the nucleotide sequence of SEQ ID NO:3), the partial amino acid sequence of the *Zea mays* ICK1 (SEQ ID NO:14 encoded by the nucleotide sequence of SEQ ID NO:5), the partial amino acid sequence of the *Zea mays* ICK2 (SEQ ID NO:15 encoded by the nucleotide sequence of SEQ ID NO:6) the partial amino acid sequence of the *Sorghum bicolor* ICK (SEQ ID NO:16 encoded by the nucleotide sequence of SEQ ID NO:7) and the partial amino acid sequence of the *Pinus taeda* ICK (SEQ ID NO:17 encoded by the nucleotide sequence of SEQ ID NO:8) (see FIG. 3).

Identities and similarities between the amino acid sequences of OsICK2 (SEQ ID NO:10) and OsICK4 (SEQ ID NO:44) and the amino acid sequences of other known plant ICKs are set forth in Table 6. The overall identity percentages between all listed ICKs range from 23 to 51% and the similarity percentages between 28 and 59%.

TABLE 6

Percentage of identity (bold) and similarity (italics) between the indicated amino acid sequences. The GAP program belonging to the GCG software (Wisconsin Package version 10.1; Madison, Wisconsin) was used with default settings gap weight = 8 and length weight = 2.

|     | At1 | At2 | At3 | At4 | At5 | At6 | At7 | Os2 | Os4 | Alf | Che |
|-----|-----|-----|-----|-----|-----|-----|-----|-----|-----|-----|-----|
| At1 | 100 | 34 | 31 | 28 | 31 | 30 | 30 | 24 | 28 | 26 | 32 |
| At2 | *44* | 100 | 30 | 23 | 23 | 35 | 28 | 24 | 23 | 29 | 27 |
| At3 | *37* | *38* | 100 | 46 | 51 | 30 | 34 | 26 | 46 | 41 | 37 |
| At4 | *38* | *36* | *55* | 100 | 34 | 26 | 26 | 31 | 38 | 39 | 27 |
| At5 | *39* | *31* | *59* | *45* | 100 | 27 | 28 | 24 | 38 | 39 | 29 |
| At6 | *37* | *46* | *34* | *36* | *34* | 100 | 49 | 30 | 34 | 24 | 30 |
| At7 | *36* | *40* | *44* | *35* | *38* | *56* | 100 | 30 | 27 | 23 | 29 |
| Os2 | *31* | *31* | *42* | *35* | *32* | *37* | *37* | 100 | 46 | 30 | 31 |
| Os4 | *36* | *32* | *53* | *47* | *45* | *41* | *37* | *52* | 100 | 41 | 26 |
| Alf | *28* | *37* | *49* | *50* | *45* | *32* | *30* | *38* | *47* | 100 | 26 |
| Che | *39* | *37* | *42* | *35* | *38* | *37* | *38* | *38* | *36* | *34* | 100 |

At1-7: *Arabidospsis thaliana* ICK1-7
Os2/4: *Oryza sativa* ICK2/4
Alf: *Medicago sativa* (alfalfa) ICK
Che: *Chenopodium rubrum* ICK Identities and similarities were calculated between the amino acid sequences of the relevant parts of the full-length OsICK2 amino acid sequence (SEQ ID NO: 10) and the full-length OsICK4 amino acid sequence (SEQ ID NO:43) with the partial amino acid sequence of OsICK1 (SEQ ID NO:11), the partial amino acid sequence of OsICK3 (SEQ ID NO:12), the partial amino acid sequence of the *Zea mays* ICK1 (SEQ ID NO:14), the partial amino acid sequence of the *Zea mays* ICK2 (SEQ ID NO:15), the partial amino acid sequence of the *Sorghum bicolor* ICK (SEQ ID NO: 16), and the partial amino acid sequence of the *Pinus taeda* ICK (SEQ ID NO: 17). The results of this calculation are included in Table 7.

TABLE 7

Percentage of identity (bold) and similarity (italics) between the indicated amino acid sequences. The GAP program belonging to the GCG software (Wisconsin Package version 10.1; Madison, Wisconsin) was used with default settings gap weight = 8 en length weith = 2.

|        | OsICK1 | OsICK2 | OsICK3 | OsICK4 | ZmICK1 | ZmICK2 | SbICK | PtICK |
|--------|--------|--------|--------|--------|--------|--------|-------|-------|
| OsICK1 | 100 | 50 | 15 | 48 | 52 | 48 | 71 | 55 |
| OsICK2 | *64* | 100 | 40 | 36 | 64 | 33 | 41 | 38 |
| OsICK3 | *35* | *44* | 100 | 29 | 25 | 24 | 43 | 47 |

TABLE 7-continued

Percentage of identity (bold) and similarity (italics) between the indicated amino acid sequences. The GAP program belonging to the GCG software (Wisconsin Package version 10.1; Madison, Wisconsin) was used with default settings gap weight = 8 en length weith = 2.

|  | OsICK1 | OsICK2 | OsICK3 | OsICK4 | ZmICK1 | ZmICK2 | SbICK | PtICK |
|---|---|---|---|---|---|---|---|---|
| OsICK4 | 57 | 42 | 36 | 100 | 37 | 75 | 30 | 56 |
| ZmICK1 | 62 | 69 | 31 | 46 | 100 | 37 | 35 | 39 |
| ZmICK2 | 57 | 38 | 31 | 81 | 41 | 100 | 37 | 50 |
| SbICK | 86 | 46 | 47 | 38 | 44 | 43 | 100 | 42 |
| PtICK | 55 | 49 | 53 | 67 | 49 | 63 | 46 | 100 |

All of the plant ICK protein sequences, including the OsICK2 (SEQ ID NO:10) sequence of the invention, were fed into the PHD secondary structure prediction software (Rost and Sander (1993) *J. Mol. Biol* 232, 584-599 and Rost, B. and Sander, C. (1994) *Proteins* 19, 55-72). The results of this analysis are summarized in FIG. 4. The conserved ICK motifs 1, 2 and 3 (SEQ ID NO:18, 19 and 20, respectively) present in all plant ICKs as described supra are not only conserved at the amino acid sequence level but also at the level of the predicted secondary structure with motif 2 being partially involved in an extended β-sheet and motifs 1 and 3 being (partially) α-helical. When present, motifs 4 and 6 (SEQ ID NO:21 and 23, respectively) are predicted to be (partially) α-helical. Motif 5 (SEQ ID NO:22) is, when present, predicted to be either partially α-helical or partially an extended β-sheet. Outside the conserved motifs, however, the predicted secondary structures of all plant ICKs, including the OsICK2 protein (SEQ ID NO:10) of the present invention, are different and unique. This observation is clearly in line with the low overall homologies between plant ICKs. The OsICK2 protein, in particular, is characterized by extensive α-helical stretches especially in between motifs 5 and 6 and in between motifs 6 and 4. The OsICK2 region between motifs 4 and 3, furthermore, only contains predicted α-helical segments and no extended β-sheets. These characteristics are different from those found in the plant ICKs belonging to the same family as OsICK2, namely alfalfa ICK and *Arabidopsis* ICKs ICK3, ICK4 and ICK5. PHD secondary prediction was not performed for the OsICK4 (SEQ ID NO:44) protein.

The presented sequence and secondary structure data, thus, clearly distinguish OsICK2 from other plant ICKs and, more specifically, from plant ICKs belonging to the same family as OsICK2.

Example 6

Expression Analysis of OsICK1, OsICK2 and OsICK4

RNA Isolation

Total RNA was extracted from 100-200 mg of immature seed, leave, root, shoot or fraction enriched apical meristems. Frozen tissues were ground with liquid nitrogen in an ice cold mortar. Two microliters of extraction buffer (1M Tris-HCl pH 9, 1% SDS, 5% β-mercaptoethanol) and an equal volume of phenol/chloroform/isoamyl alcohol (PCI 25/24/1) were added in the mortar and grinding continued until the paste thawed. The mixture was transferred to a tube and vortexted at 10,000 rpm for 10 minutes. The aqueous layer was removed and re-extracted with an equal volume of PCI. After centrifugation (at 10,000 rpm for 10 minutes) the supernatant was precipitated at 4° C. for 10 minutes with a 1/10 volume of 3M sodium acetate and 0.8 volumes of cold isopropanol. The pellet recovered after centrifugation was washed twice with 70% ethanol/0.1M sodium acetate (pH 5.5) before resuspending in 0.5 ml of $H_2O$. RNA was precipitated by adding an equal volume of 4M LiCl and incubating on ice overnight. The RNA was collected by centrifugation and the pellet washed twice with 70% ethanol/0.1 M sodium acetate. The pellet was drained and dissolved in approximately 80 µl of water.

cDNA Synthesis

The cDNA synthesis was performed using the "Superscript preamplification system for first strand cDNA synthesis" kit from Gibco BRL. Three µg of total RNA were mixed with 0.5 µg of an anchored oligo $(dT)_{25}$ and 12 µl of DEPC water. The mixture was incubated at 70° C. for 10 minutes and then incubated on ice for at least 1 minute. The following solutions were then added: 2 µl of 10× PCR buffer, 2 µl of 25 mM $MgCl_2$, 1 µl of 10 mM dNTP mix, and 2 µl of 0.1 M DTT. After an incubation of the mixture at 42° C. for 5 minutes, 1 µl of Superscript II RT was added and the incubation at 42° C. was continues for 50 minutes. The reaction was terminated at 70° C. for 15 minutes and then chilled on ice. One µl of RNase H was added and the reaction was incubated for 20 minutes at 37° C.

Amplification of the Target cDNA

The first strand cDNA obtained as described in the previous paragraph was amplified using PCR, using the following reactants:

| | |
|---|---|
| 10X PCR buffer | 5 µl |
| 2 mM dNTP mix | 5 µl |
| sense primer (10 µM) | 1 µl |
| antisense primer (10 µM) | 1 µl |
| Taq DNA polymerase (Boerhinger) | 0.5 µl |
| cDNA | 2 µl |
| water | 35.5 µl |

The primers used for the RT-PCR amplifications were as described in Example 2: primers with SEQ ID NOs: 25 and 26 for OsICK1; primers with SEQ ID NOs: 27 and 28 for OsICK2; and primers with SEQ ID NOs: 31 and 32 for OsICK4.

The DNA amplification was carried out using the following conditions (for OsICK4 amplification, the primer annealing temperature was 58° C. instead of 55° C.):

94° C. for 3 min $\left.\begin{array}{l}94° \text{ C. for 45 sec}\\ 55° \text{ C. for 45 sec}\end{array}\right]$ 15 cycles for immature seed 72° C. for 1 min $\left.\begin{array}{l}94° \text{ C. for 45 sec}\\ 55° \text{ C. for 45 sec}\end{array}\right]$ 20 cycles for other tissues 72° C. for 1 min 72° C. for 5 min Hybridization Analysis Fifty μl of the above-described PCR reaction were loaded on an 1.5% agarose gel. The DNA was blotted onto nylon membranes (Hybond N+, Amersham) and the membranes were baked at 80° C. for 2 hours. The hybridization was performed using the "North2South Chemiluminescent Nucleic Acid Hybridization and Detection" kit from Pierce. The DNA was prehybridized for 4 hours at 55° C. in the hybridization buffer supplied by the kit and then hybridized overnight in the same buffer with a biotin-labelled OsICK2 or OsICK1 insert using the North2South Biotin Random Prime Kit (Pierce).

The membranes were washed twice for 20 minutes at room temperature in 2×SSC/G. 1% SDS and twice in 0.5×SSC/0.1% SDS for 15 minutes at 55° C. (at 60° C. in the case of OsICK4). The probe detection and substrate development were performed according to the manufacturer's instructions.

Probe Detection and Substrate Development

The probe detection and substrate development were performed according to the manufacturer's instructions. Briefly, after washing the membranes were blocked with the North2South Blocking buffer for 15 minutes at room temperature (RT). The Streptavidin-HRP conjugate was added to the North2South Blocking buffer at a 1:300 final dilution and incubated for 15 minutes at room temperature. The membranes were washed four times for 5 minutes each with North2South wash buffer at RT and then transferred in the North2South Substrate Equilibration buffer for 5 minutes at RT. The substrate development was carried out by covering the membranes with a mix of luminol/enhancer sotution-peroxyde solution for 10 minutes.

The membranes were placed into a film cassette and exposed to film for 1 minute. The film was developed by incubation for 5 minutes in the developer and for 5 minutes in the fixer solution.

Results

OsICK1 is predominantly expressed in stems. Lower levels of OsICK1 expression are apparent in roots, stem meristems, and seeds, whereas no or only very low expression of OsICK1 could be observed in the leaves (see FIG. 6). OsICK2 is expressed in all rice plant tissues investigated including the leaves (FIG. 6). OsICK4 is also expressed in all rice plant tissues investigated with a lower expression in roots and a higher expression in leaves and seeds (FIG. 6).

Expression of OsICK1 rises very early during seed development with a peak at 2 days after pollination (DAP) and then slowly declines as seed development progresses. OsICK2 transcripts are abundantly present in seeds throughout their development with a peak at 8 DAP (see FIG. 7). OsICK4 transcript levels are highly abundant in unpollinated flowers and during the first 3 days of seed development (i.e., the first 3 days after pollination). Thereafter, OsICK4 expression gradually declines during the remaining period of seed development (see FIG. 7).

Example 7

In Situ Hybridization of OsICK2 in Rice Immature Seeds

In situ hybridization was performed according to the protocol of de Almeida-Engler et al. (2000) (Methods, in press) with slight modifications. Fixation was performed using 4% formaldehyde, 2.5% glutaraldehyde in 0.1 M cacodilate buffer and a 1 hour incubation under vacuum. The fixative was refreshed and treatment continued for 4-5 hours up to overnight at 4° C. The samples were then dehydrated using ethanol, transferred to xyleen and embedded in paraplast. Subsequently, 10 μm sections were cut and placed on Vectabond coated slides. In vitro transcription and radioactive labelling ($S^{35}$) was performed using a transcription kit from Boehringer-Manheim according to the manufacturer's instructions. For this OsICK2 was cloned in a pSP6 vector (Roche Diagnostic) in sense and antisense orientation behind the T7 promoter. Hybridization and developing of the slides were performed according to de Almeida-Engler et al., supra.

Figure 8:
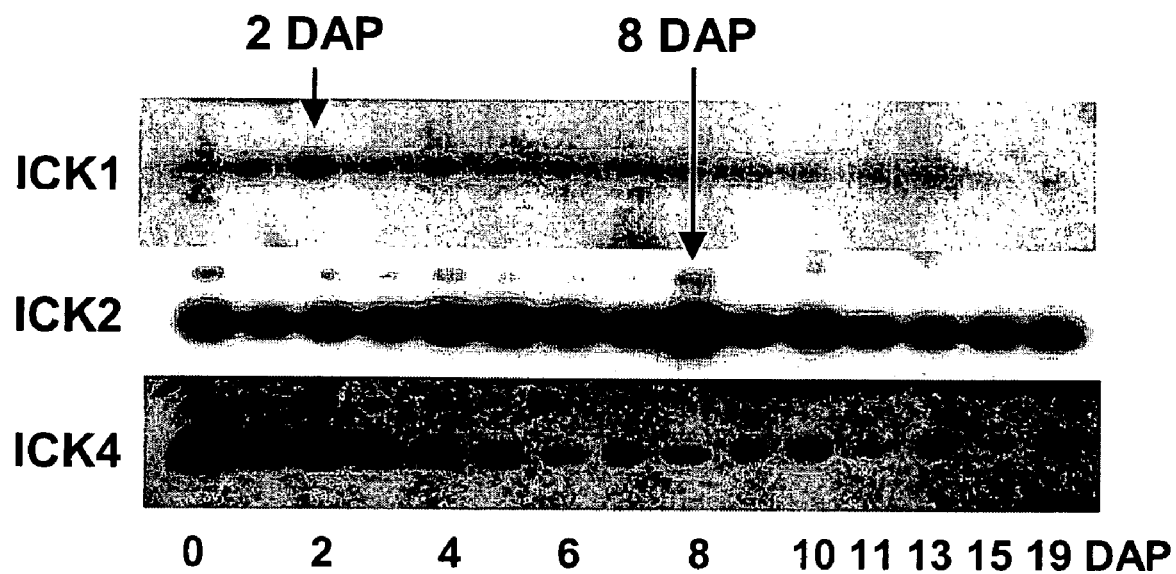
FIG. 8 is a blot depicting the expression of OsICK1 ('ICK1'), OsICK2 ('ICK2') and OsICK4 ('ICK4') in developing rice grains. cDNA obtained by RT-PCR was subjected to DNA gel blot analysis with biotin-labeled probes specific for OsICK1, OsICK2 and OsICK4. (DAP: days after pollination).
Figure 9:
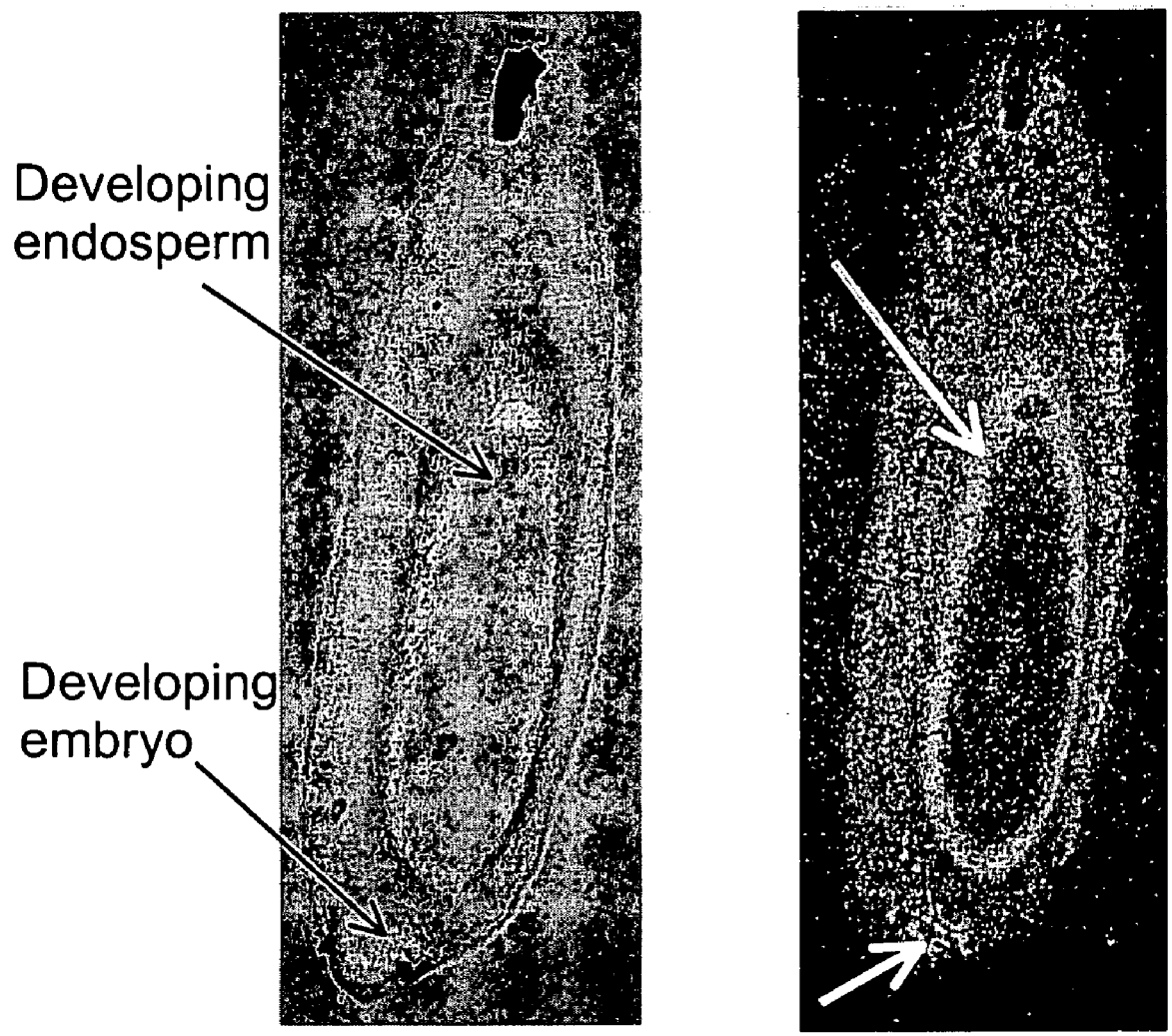
FIG. 9 depicts the results from an in situ hybridization analysis of OsICK2 expression in rice seeds collected 7 days after pollination. Dark field microscopy (right panel) visualizes a clear (bright white) hybridization signal in the cell layer(s) surrounding the developing endosperm (white arrow). A patchy hybridization signal is also obvious in the developing embryo (white arrow). The bright field microscopic image (left panel) shows the morphology of the toluidine blue-stained section.

In situ hybridization analysis of OsICK2 expression in rice seeds revealed that OsICK2 transcripts are spatially confined to the cell layers between the seed coat and the developing endosperm and display a patchy pattern in the developing embryo in seeds collected at 7 DAP (FIG. 8). In seeds collected at 20 DAP, OsICK2 expression is still strong in the cell layers between the seed coat and the developing endosperm, as well as in the scutellum (FIG. 9).

Example 8

Transformation of *Arabidopsis thaliana* with *A. thaliana* ICKs ICK2, ICK3 and ICK4

The full-length coding regions of the *A. thaliana* ICKs ICK2, ICK3 and ICK4 were amplified by polymerase chain reaction using the appropriate primers introducing different restriction sites. The amplified fragments were digested with the corresponding restriction enzymes and cloned in the corresponding sites of pH35S (Hemerly et al. (1995) *EMBO J.* 14, 3925-3936) containing the CaMV35S promoter and NOS terminator. The expression cassettes were subcloned in pGSV4 (Hérouart et al. (1994) *Plant Physiol* 104, 873-880). The resulting vectors were mobilized by the helper plasmid pRK2013 into *Agrobacterium tumefaciens* C58C1Rif$^R$ harboring plasmid pMP90. *A. thaliana* plants of the Col-0 ecotype were transformed by the floral dip method (Clough and Bent (1998) *Plant J.* 16, 735-743). Transgenic plants were obtained on kanamycin-containing media and later transferred to soil for optimal seed production. A total of 39 and 5 transgenic *A. thaliana* lines were generated from the transformations with ICK2 and ICK3, respectively.

Example 9

Transgenic Rice Plants Generated with Different Expression Patterns for OsICK4

A number of different constructs have been produced to either overexpress or down-regulate OsICK4 expression. The binary vector backbone is pCAMBIA1301. Constructs for modulating OsICK4 expression are outlined below.

OsICK4 Overexpression

The binary vector backbone is a proprietary vector, pCDV3 (pCAMBIA1301 derivative), into which the Gateway system (Life Technologies, Inc) has been introduced. Gateway primers have been designed to amplify OsICK4 following the instructions of the manufacturer. The construct for overexpression of OsICK4 under the control of the GOS2 promoter (de Pater et al. (1992) *Plant J.* 2, 837-844) is designated p0428 ICK4 and is depicted in FIG. 12.

OsICK4 Co-Suppression

To down-regulate gene expression, an inverted repeat conformation with a hairpin structure has been produced. The two inverted fragments from OsICK4 are separated by a matrix attachment region (MAR) from *Nicotiana tabacum* (GenBank accession number U67919). The MAR fragment of 315 bp has been PCR-amplified from tobacco genomic DNA using primers sense 5'-CGTTGTCAATATCCTG-GAAATTTTGC-3' (SEQ ID NO:35) and antisense 5'-CTGC-CATTCTTTAGAGGGGATGCTTG-3' (SEQ ID NO:36), and blunt-end subcloned into a SmaI-CIP pUC18.

Figure 13:
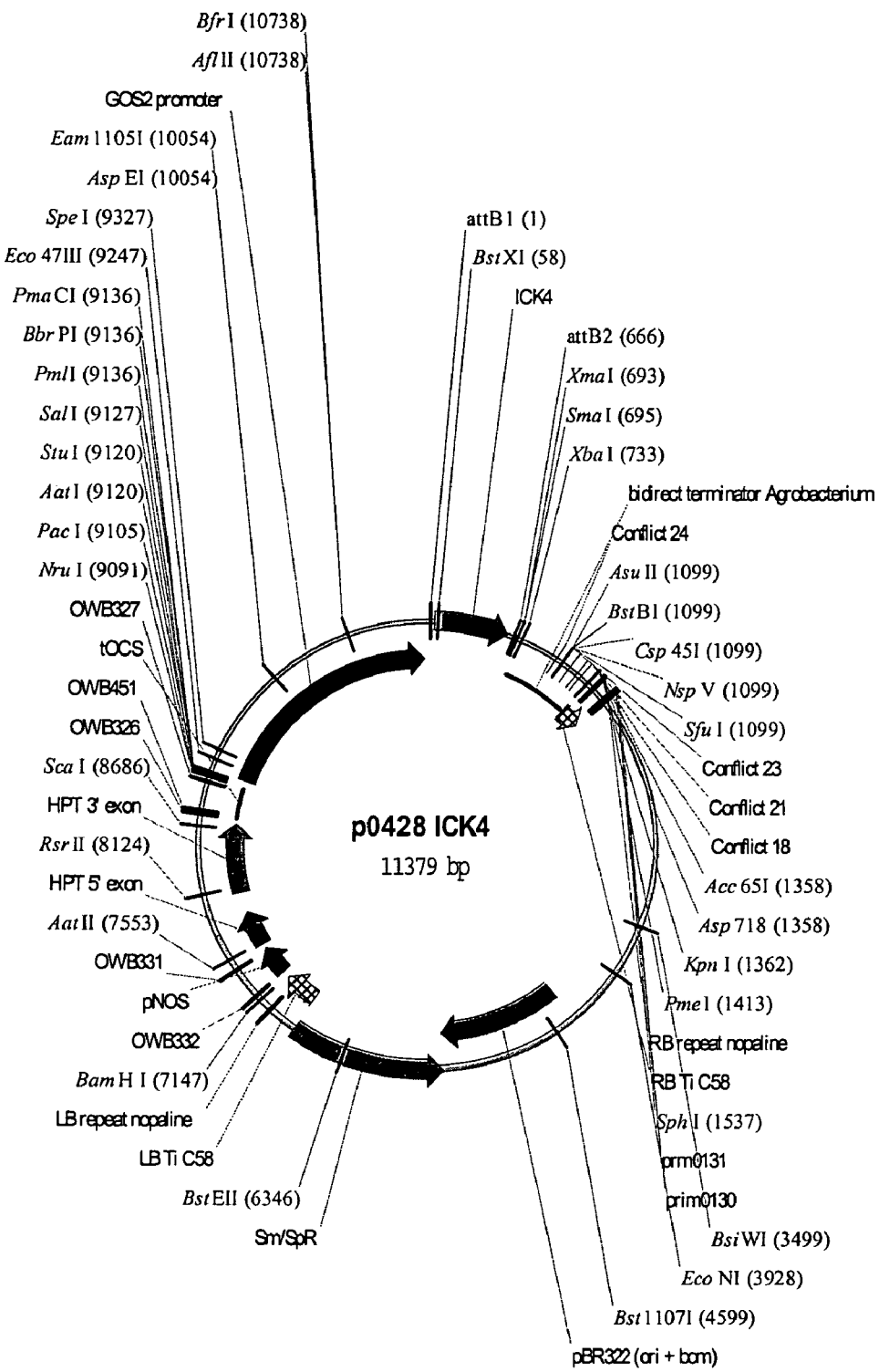
FIG. 13 depicts the binary plant transformation vector p0428 ICK4 comprising the OsICK4 ORF operably linked to the GOS2 promoter.

A first OsICK4 fragment (893 bp) cut out from pAD-OsICK4 (full length) with Ecl136II-HincII is blunt ligated into pUC18-MAR cut with Ecl136 II (blunt). The orientation in which Ecl136 II has been restored is chosen to allow the excision of the whole inverted repeat (IR) cassette in a later stage. The second OsICK4 fragment (921 bp) is cut out from pAD-OsICK4 (full length) with PstI-HincII (Ecl136II is included in the sequence) and subloned into pUC18-Mars-OsICK4 restricted with PstI-HincII in a sticky-blunt ligation. The vector pUC18-Mars-OsICK4 is depicted in FIG. 13. The final inverted repeat cassette (2,129 bp; termed OsICK4 IR) can be taken out using Ecl136II for subcloning in, for example, a plant transformation vector.

OsICK4 IR with GOS2 Promoter

The pCAMBIA vector 1301 containing a 35SCaMV promoter driving GUS expression has been restricted with XbaI and NcoI to replace the 35SCaMV promoter with the GOS2 promoter XbaI-NcoI fragment from rice (de Pater et al. (1992) *Plant J.* 2(6): 837-844).

Figure 14:
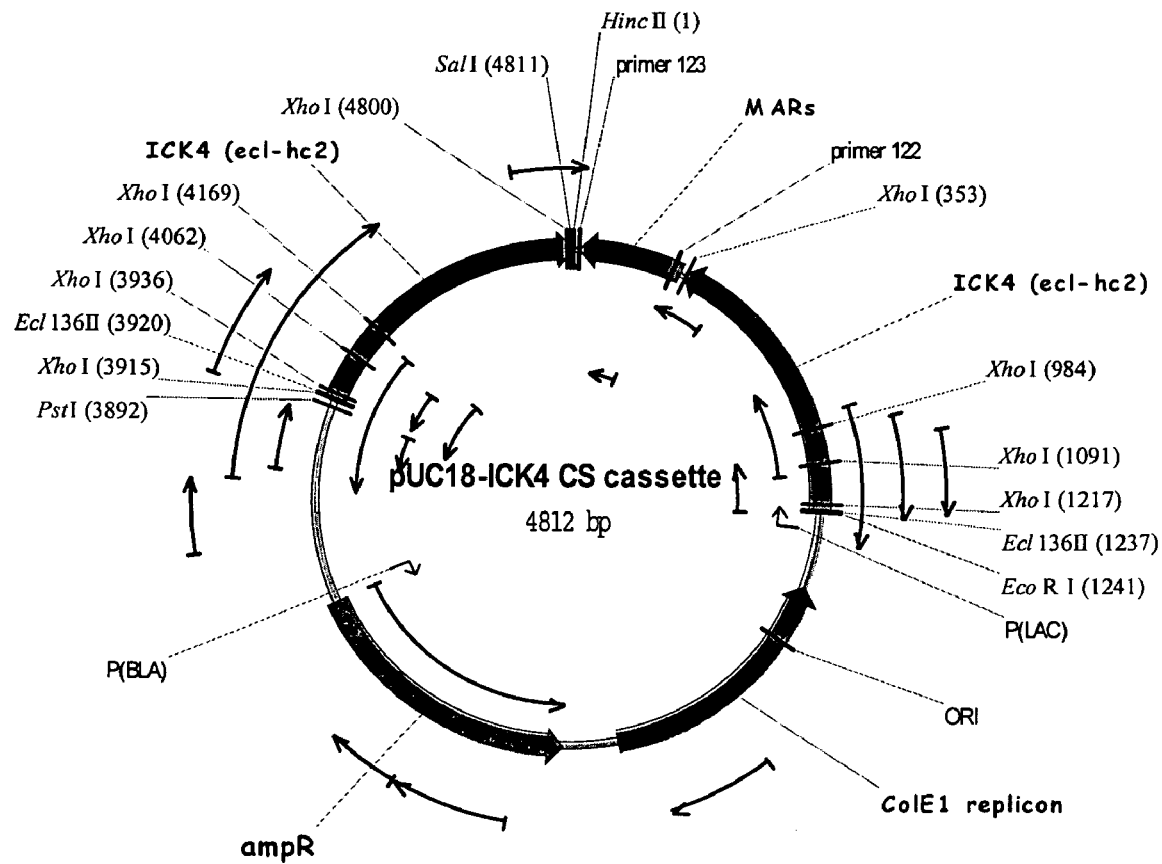
FIG. 14 depicts the pUC18 derivative vector pUC18-ICK4 CS comprising the cassette with inverted repeats of an OsICK4 cDNA fragment separated by the tobacco MAR sequence. This cassette is used for co-suppression of OsICK4 expression in transgenic plants.

This vector is then restricted with NcoI and PmlI, and these sites filled-in to produce blunt ends. The final inverted repeat cassette (OsICK4 IR) from pUC18 is taken out using Ecl136II and ligated into the binary vector. The resulting vector is termed p0490 and depicted in FIG. 14.

OsICK4 IR with Prolamine Promoter

Figure 15:
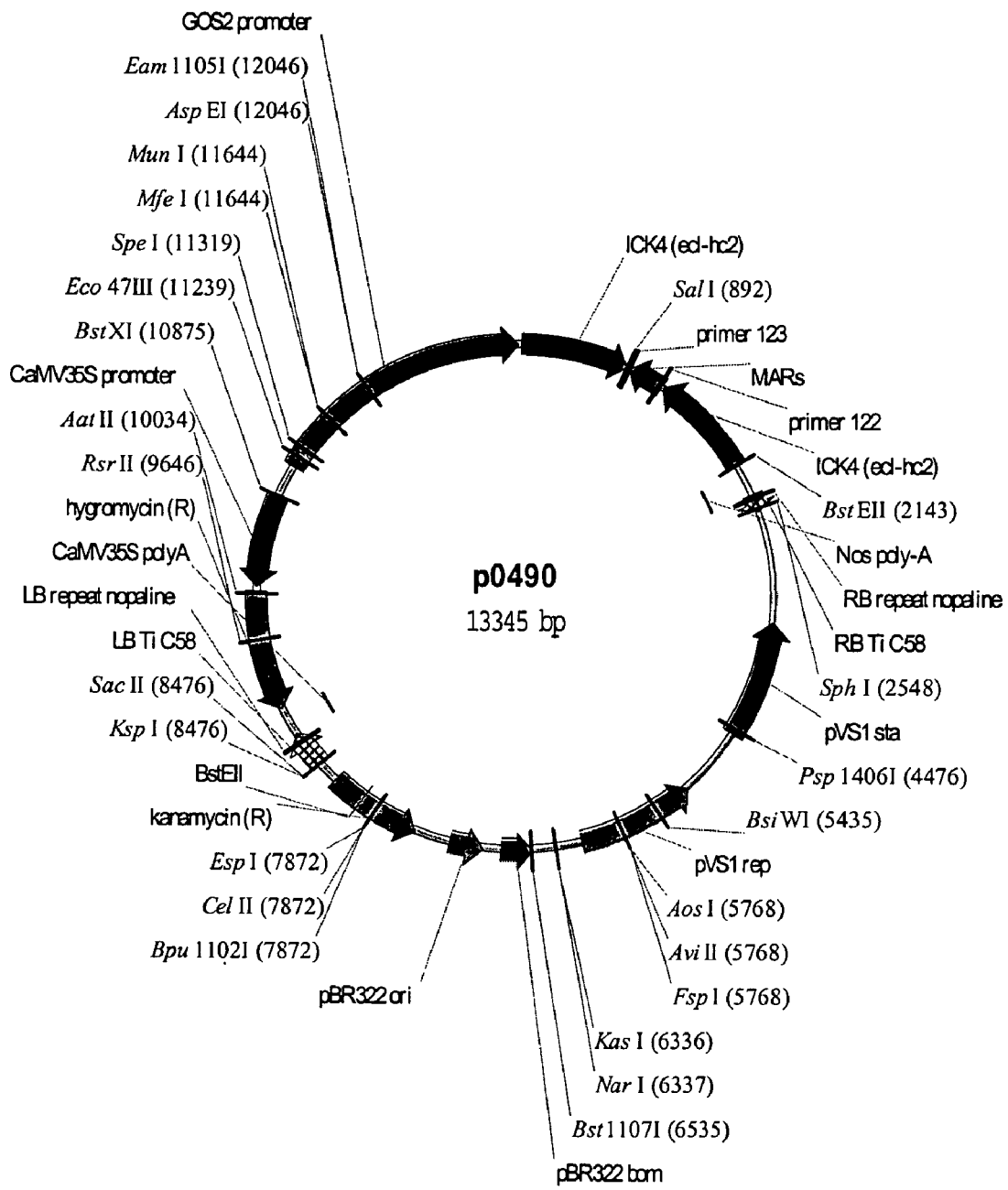
FIG. 15 depicts the binary plant transformation vector p0490 comprising the OsICK4 co-suppression cassette of pUC-ICK4 CS (see FIG. 13) operably linked to the GOS2 promoter.

The 13 kDa prolamine promoter (654 bp) from rice (Wu et al. (1998) *Plant Cell Physiol.* 39:885) has been PCR-amplified using primers sense 5'-GAATTCCTTCTACATCGGCT-TAGGTGTAGC-3' (SEQ ID NO:46) and antisense 5'-CCATGGTGTTGTTGGATTCTACTACTATGC-3' (SEQ ID NO:47) and the subsp. *Japonica genomic* DNA. The fragment was further subcloned in pUC18 SmaI CIP. An XbaI and NcoI restriction produced a promoter fragment that was subcloned into the pCAMBIA 1301 35SCaMV-GUS vector also restricted with XbaI and NcoI. This led to the replacement of the CaMV promoter by the prolamine promoter. This prolamine-GUS binary vector was then restricted with NcoI and PmlI to introduce the IR cassette. After filling-in these sites to produce blunt ends, the Ecl136II final IR cassette (OsICK4 IR) was taken from the pUC18 and ligated into the binary vector. The resulting vector is termed p0489 and depicted in FIG. 15.

OsICK4 IR with Oleosin Promoter

Figure 16:
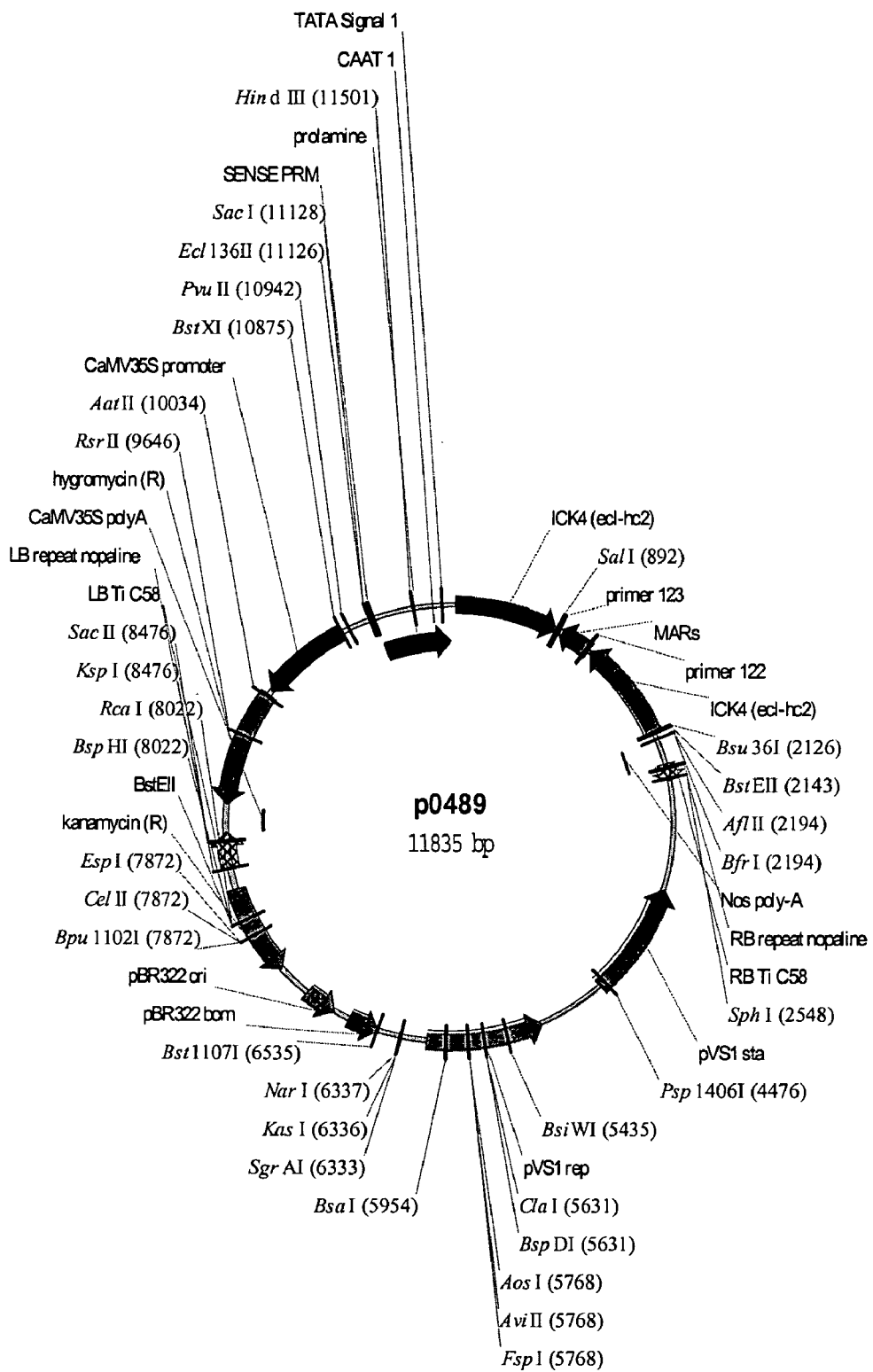
FIG. 16 depicts the binary plant transformation vector p0489 comprising the OsICK4 co-suppression cassette of pUC-ICK4 CS (see FIG. 13) operably linked to the prolamine promoter.

The 18 kDa oleosin promoter (1236 bp) from rice (Wu et al. (1998) *Plant Cell Physiol* 39:885) has been PCR-amplified using primers sense 5'-GAACAAAGATGGTCAGC-CAATACATTGATC-3' (SEQ ID NO:48) and antisense 5'-GGCCATGGCTAAGCTAGCTAGCAAGATGAA-3' (SEQ ID NO:49) and the subsp. Indica genomic DNA. The fragment was further subcloned into pUC18 SmaI CIP. An XbaI and NcoI restriction produced a promoter fragment that was subcloned into the pCAMBIA 1301 35SCaMV-GUS vector also restricted with XbaI and NcoI. This led to the replacement of the CaMV promoter by the oleosin promoter. This oleosin-GUS binary vector was then restricted with NcoI and PmlI to introduce the IR cassette. After filling-in these sites to produce blunt ends, the Ecl136II final IR cassette (OsICK4 IR) was taken from the pUC18 and ligated into the binary vector. The resulting vector is termed p0488 and depicted in FIG. 16.

OsICK4 IR with Glutelin Promoter

Figure 17:
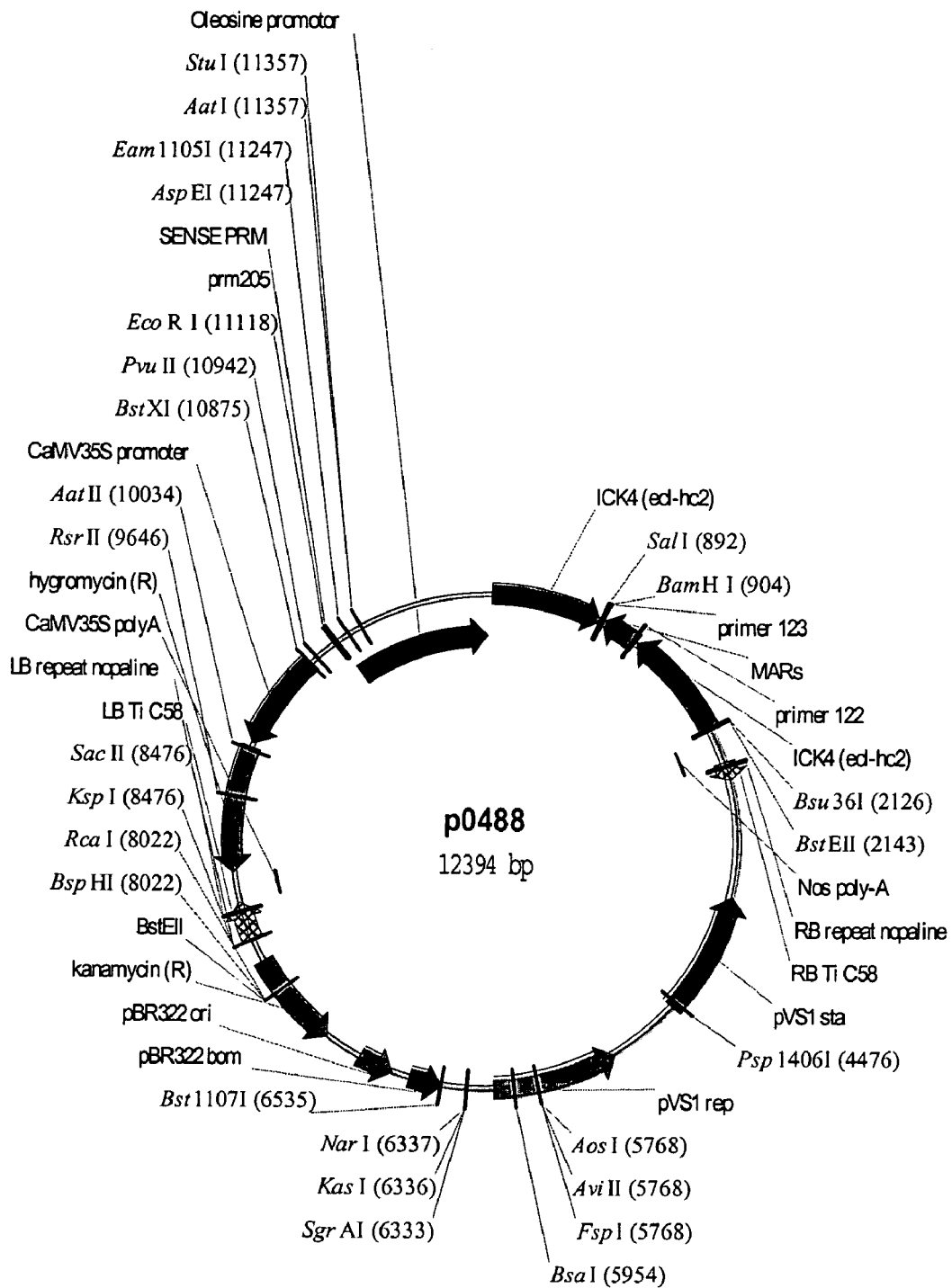
FIG. 17 depicts the binary plant transformation vector p0488 comprising the OsICK4 co-suppression cassette of pUC-ICK4 CS (see FIG. 13) operably linked to the oleosine promoter.

The glutelin 3A promoter (984 bp) from rice (Wu et al. (1998) *J. Biochem.* 123: 386) has been PCR-amplified using primers sense 5'-AGAAGAAAGATAAATAACCGAAAC-TATTTG-3' (SEQ ID NO:50) and antisense 5'-GGACAT-GTTTTTGTGGGACTGAACTCAATG-3' (SEQ ID NO:51) and the subsp. Indica genomic DNA. The amplified fragment was further subcloned into pUC18 SmaI CIP. A SmaI and AflIII restriction produced a promoter fragment that was subcloned into the pCAMBIA 1301 35SCaMV-GUS vector restricted with SmaI and NcoI. This led to the replacement of the CAMV promoter by the glutelin promoter. This glutelin-GUS binary vector was then restricted with BglII and PmlI to introduce the IR cassette. After filling-in these sites to produce blunt ends, the Ecl136II final IR cassette (OsICK4 IR) was taken from the pUC18 and ligated into the binary vector. The resulting vector is termed p0559 and depicted in FIG. 17.

Example 10

*Agrobacterium*-Mediated Rice Transformation

Mature dry seeds of the rice japonica cultivars Nipponbare or Taipei 309 are dehusked, sterilised and germinated on a medium containing 2,4-D (2,4-dichlorophenoxyacetic acid). After incubation in the dark for four weeks, embryogenic, scutellum-derived calli are excised and propagated on the same medium. Selected embryogenic callus is then co-cultivated with *Agrobacterium*. Widely used *Agrobacterium* strains such as LBA4404 or C58 harbouring binary T-DNA vectors can be used. The hpt gene in combination with hygromycin is suitable as a selectable marker system but other systems can be used. Co-cultivated callus is grown on 2,4-D-containing medium for 4 to 5 weeks in the dark in the presence of a suitable concentration of the selective agent. During this period, rapidly growing resistant callus islands develop. After transfer of this material to a medium with a reduced concentration of 2,4-D and incubation in the light, the embryogenic potential is released and shoots develop in the next four to five weeks. Shoots are excised from the callus and incubated for one week on an auxin-containing medium from which they can be transferred to the soil. Hardened shoots are grown under high humidity and short days in a phytotron.

Seeds can be harvested three to five months after transplanting. The method yields single locus transformants at a rate of over 50% (Aldernita and Hodges (1996), Chan et al. 1993, Hiei et al. 1994).

Example 11

Two-Hybrid Interaction of OsICK2 and OsICK4 with CDC2-Os1 and CYCD3Os

The interactions of OsICK2 and OsICK4 with Cdc2-Os1 and CycD3-Os (the rice cyclin D3) were verified using a yeast two hybrid approach. In a preliminary step, yeast strain PJ69-4A (MATa trp1-901 leu2-3,112 ura3-52 his3-200 gal4(deleted) gal80(deleted) LYS2::GAL1-HIS3 GAL2-ADE2 met2::GAL7-lacZ) was transformed with Cdc2-Os1 in bait vector pBDGal4 (Stratagene), using the lithium acetate method, well known to those skilled in the art. The rice Cdc2-Os1 was previously obtained by PCR as described in Example 1. The Cdc2-Os1 was also cloned in the pADGal4 prey vector. The junctions between the pBDGal4 binding domain and the pADGal4 activation domain and the Cdc2-Os1 fragment were sequenced to verify correct in-frame fusion.

The full-length OsICK2 and OsICK4 cDNA clones in the pADGal4 vector were obtained as described in Examples 3 and 4. These cDNAs were also cloned in the pBDGal4 vector. The public databases were screened for conserved motifs found in all D-type cyclins. This search yielded a hit consisting of a rice EST clone (GenBank accession number AU082424). PCR was performed to amplify a part of this clone using the following primers: antisense 5'-ACTCCT-TGTCCCTATCGACACACC-3' (SEQ ID NO:52) and sense 5'-CCATGGGGGACGCCTCGGCATCCA-3' (SEQ ID NO:53). The amplified fragment was cloned in pUC18 and used as a radioactive probe for the two-hybrid cDNA library screening.

Approximately 750,000 plaque-forming units from the cell suspension two-hybrid cDNA library were screened. Plaques were transferred to Hybond N+ membranes (Amersham). The filters obtained were prehybridized in sodium phosphate 0.25M, (pH 7.2), SDS 7% at 60° C. for 4 hours. Hybridization was performed with the prehybridization buffer containing 50 ng of $[\alpha]^{32}$P-dCTP-labelled probe at 60° C. overnight (protocol of Church G. M. and Gilbert W. PNAS USA 81:1991-1994). The filters were washed twice with 1×SSC, 0.1% SDS at 60° C. for 30 minutes and then once with 0.1×SSC, 0.1% SDS at 60° C. for 30 minutes. The membranes were placed into a film cassette and exposed to film for 6 hours.

Two putative positive clones were identified. A second round of screening on these clones was performed. Pure positive plaques were isolated and phagemids were excised therefrom. Sequencing of the two clones revealed that the clones were identical with a full length size of 1.7 kb. The clones contain an ORF of 1140 bp encoding a protein of 380 amino acids. This protein is designated cyclin D3 from rice (CycD3-Os). The yeast stain PJ69-4a containing the bait vector pBD-Gal4 with Cdc2-Os1 was retransformed with the prey vector pADGal4 containing the in-frame OsICK2 or CycD3-Os, and plated on selective Leu-Trp-His- to select for growth. The yeast expressing both proteins could effectively grow, illustrating the interaction of Cdc2-Os1 with OsICK2 and CycD3-Os, respectively.

As positive controls, growth was assessed in yeast containing the prey vector pADGal4 with Cdc2-Os1 and retransformed with the bait vector pBDGal4 containing OsICK2 or CycD3-Os. In all cases, yeast growth did occur. Appropriate negative controls were incorporated in which any of the described bait pBDGal4 or prey pADGal4 vectors containing either Cdc2-Os1, OsICK2 or CycD3-Os were combined with the empty prey pADGal4 or pBDGal4 vectors, respectively. None of these combinations was able to sustain yeast growth on selective medium.

From the molecular cloning of OsICK4 (see Example 4), it is evident that OsICK4 interacts physically with Cdc2-Os1.

In further experiments, the interaction between OsICK2 and OsICK4 with CycD3-Os, respectively, was assessed. Both OsICK2 and OsICK4 were shown to interact with CycD3-Os in a yeast two-hybrid system as described above.

Example 13

Expression of Recombinant ICK Proteins in Bacterial Cells

In this example, the ICK molecules of the present invention are expressed as a recombinant glutathione-S-transferase (GST) fusion polypeptide in E. coli and the fusion polypeptide is isolated and characterized. Specifically, ICK molecules are fused to GST and this fusion polypeptide is expressed in E. coli, e.g., strain PEB199. Expression of the GST-ICK fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 14

Isolation of the Rice OsICK5 Genomic Clone and Prediction of the OsICK5 cDNA and Protein Sequences The public databases were screened for the "GRYEW" amino acid motif located at the carboxy-termini of all ICKs. This research yielded a hit with a non annotated HTGS full length clone (GenBank accession number AP003525). PCR was performed to amplify this genomic clone using the following primers:

-sense:5'-GGGGACAAGTTTGTACAAAAAAGCAG-GCTTCACAATGGGGAAGAA GAAGAAGCGC-GACG-3' (SEQ ID NO:57); and -antisense:5'-GGGGACCACTTTGTACAA-GAAAGCTGGGTTCAGCCGCTGCCCAC CGCGG-3' (SEQ ID NO:58).

The amplified fragment was cloned in the pDON201 (Gateway system; Life Technologies).

Said sense and antisense primers (SEQ ID NO:57 and SEQ ID NO:58, respectively) are subsequently used to isolate the full-length OsICK5 cDNA by RT-PCR (see, e.g., Example 6).

The isolated OsICK5 genomic clone (SEQ ID NO:56; FIG. 19) is part of the HTGS clone with GenBank accession number AP003525 (version 1) but no open reading frame or protein annotation is presented. Therefor, the open reading frame and protein deduced thereof were predicted. The predicted full-length OsICK5 cDNA is defined by SEQ ID NO:54 and the OsICK5 protein sequence deduced thereof is defined by SEQ ID NO:55. During the prediction process, difficulties araised in defining the correct exon-intron borders. These uncertainties are reflected in the OsICK5 cDNA sequence (SEQ ID NO:54; FIG. 20A) by two 'N' nucleotides (i.e. may be any nucleotide (A, T, C or G) or a stretch of such nucleotide residues) at the positions 355 and 356 of SEQ ID NO:54. As defined in SEQ ID NO:54, the stretch of uncertain nucleotides may have a length of zero to 265 nucleotides, i.e. the maximum length between the intron involved. Said uncertain nucleotides being translated into an uncertain amino acid residue X (i.e. may be any amino acid residue or a stretch of such amino acid residues) at the position 119 of SEQ ID NO:55. As defined in SEQ ID NO:55, the stretch of uncertain amino acids may have a length of zero to 88 amino acids, i.e. the maximum protein sequence deducable from the whole intron involved.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. A method for downregulating the activity of a cyclin-dependent kinase inhibitor (ICK) in a monocot plant selected from the group consisting of rice, maize, wheat, barley, sorghum, oats, sugarcane, rye and triticale, said method comprising introducing into the monocot plant an antisense molecule about 20 nucleotides in length and targeted to a nucleic acid molecule encoding an ICK, said nucleic acid molecule encoding an ICK selected from the group consisting of SEQ ID NOs: 4, 43, and 45, or a nucleic acid molecule at least 95% identical thereto.

2. The method of claim 1 wherein plant growth is enhanced, senescence of the plant is delayed, seed yield and/or seed size is increased, or enhanced formation of lateral organs from the plant tissue and/or an organ is obtained.

3. A method for improving tolerance to an environmental stress condition in a monocot plant selected from the group consisting of rice, maize, wheat, barley, sorghum, oats, sugarcane, rye and triticale, said method comprising introducing into the plant an antisense molecule about 20 nucleotides in length and targeted to a nucleic acid molecule encoding a cyclin-dependent kinase inhibitor (ICK), said nucleic acid molecule encoding an ICK selected from the group consisting of SEQ ID NOs: 4, 43, and 45, or a nucleic acid molecule at least 95% identical thereto and wherein the environmental stress condition is selected from the group consisting of drought stress, salt stress, temperature stress, and nutrient deprivation.

4. A method for increasing seed number in a monocot plant selected from the group consisting of rice, maize, wheat, barley, sorghum, oats, sugarcane, rye and triticale, said method comprising introducing into the plant an antisense molecule about 20 nucleotides in length and targeted to a nucleic acid molecule encoding a cyclin dependent kinase inhibitor (ICK) selected from the group consisting of SEQ ID NOs: 4, 43, and 45, or a nucleic acid molecule at least 95% identical thereto, wherein the antisense molecule is under the control of an endosperm-specific promoter.

5. The method of claim 4 wherein the endosperm-specific promoter is the prolamin promoter.

6. The method of claim 4 wherein the plant is rice.

* * * * *

SEQUENCE LISTING

```
<160> NUMBER OF SEQ ID NOS: 59

<210> SEQ ID NO 1
<211> LENGTH: 493
<212> TYPE: DNA
<213> ORGANISM: Oryza sativa
<220> FEATURE:
<221> NAME/KEY: misc_feature
<222> LOCATION: (52)..(52)
<223> OTHER INFORMATION: n = A, T, C or G
<220> FEATURE:
<221> NAME/KEY: misc_feature
<222> LOCATION: (180)..(181)
<223> OTHER INFORMATION: n = A, T, C or G
<220> FEATURE:
<221> NAME/KEY: misc_feature
<222> LOCATION: (186)..(186)
<223> OTHER INFORMATION: n = A, T, C or G
<220> FEATURE:
<221> NAME/KEY: misc_feature
<222> LOCATION: (461)..(461)
<223> OTHER INFORMATION: n = A, T, C or G

<400> SEQUENCE: 1
ccgccgagat cgaggcgttc ttcgcggcgg ccgaggaggc tgaggccaag cnttcgccgc      60
caagtacaac ttcgacgtcg ttcgcggcgt gccctcgac gccggtcggt tcgagtggac     120
tccggtggtc agcagccgaa gctgaagcga gcgtgcagat taagcggaag ctagaaaggn    180
nggtancagg ggggcgccgt gtagaaaggg aaggcgagct agagagagga gaagaagaag    240
aagaaaagat gctcatccaa agggaataaa ctggaaaagt gggagactac aaaaaaagaa    300
gcattatagc ctaacaacca ccgattcgac tcttttttct ttcacatttt ctttgcattt    360
ttactcttac tgtgtactag aaagtagtag cagtagtaaa ctagtaattc gtcccagtat    420
ttatcagagg tttatctcga taggaataga tatattatcc nctaaaaaaa aaaaaaaaaa    480
aaaaaaaaaa aaa                                                      493

<210> SEQ ID NO 2
<211> LENGTH: 696
<212> TYPE: DNA
<213> ORGANISM: Oryza sativa

<400> SEQUENCE: 2
aagctaagct aaatcaagct aattagtttt ttaattaatc tgcttaattt gcaaactaat     60
tacactgcga gctgccggtt ttgcaggtac aattacgaca ttgccctcga ccgcccgttg    120
caaggccgct acgagtggga gccagtgagc acgtgaaagg gaggggtaga agtgtcaact    180
caactcacac ccatgtctgc aactcacaag tgatgcaaag ctagcttaat catcagcagc    240
taattatctg ggagaggctg gggatcgagt tagtgacctc gtttctcctg ctaattctca    300
attagggaat taattaatta ctcctcaatc ctcatctcca cctgttgtca gttggatctc    360
```

| | |
|---|---:|
| actaccatat atatctcagc tctgtcaatt aatcttttgt atagttggta ggaaataatc | 420 |
| aaggataatc caggtgattt ggaggatgct tctgatgagc tcccctcttg ctaattacta | 480 |
| atatgtatct tccacataat ttcgcctaat ttactgttta ttactactta ttaagcccct | 540 |
| tcaaaaataa gtatttcatc cgtttcacaa ggtaagactt tctagcattg tacacattta | 600 |
| tttatatatt aatgaattta gacatatgta ttgatttaga atcattaata tctatatgta | 660 |
| tatgtgcaat gctagattgt cttatattgt aaaacg | 696 |

<210> SEQ ID NO 3
<211> LENGTH: 415
<212> TYPE: DNA
<213> ORGANISM: Oryza sativa

<400> SEQUENCE: 3

| | |
|---|---:|
| ctcctgtgta gtcactaata agcacaaatc ttatatttca aaattaaacc atacgtaagt | 60 |
| cgaaaatttt attttacaaa aggtaattcg tgacaatttt ttttctagct tagtaattaa | 120 |
| ttacactgtc agtctgtcac acactcacac tcactaataa taactcttgc ttctactctc | 180 |
| tccaattcag aaagtctttg aagccaaatt cttgttcccg cgaagtggcg gcggaacacg | 240 |
| ccggcgagca caagcacaac cctgcagccg ccgcggcggc cggccgccgg ccaccgctgt | 300 |
| cgccgccgga agcggagatc gaggcgttct tcgccgccgc ggagctcgcc gagcgccggc | 360 |
| gattcgcaga gaagtacgta tacacacaca cataatcact catctctctc tagct | 415 |

<210> SEQ ID NO 4
<211> LENGTH: 1614
<212> TYPE: DNA
<213> ORGANISM: Oryza sativa

<400> SEQUENCE: 4

| | |
|---|---:|
| ttcttggccc atgccccccaa attgtcacca ccattaaatg tttgaggtga aaggaggggt | 60 |
| cctcccccgt ccccacaagt actagaagtt gatttgttgg tgatctttgg ttcaagctag | 120 |
| ggggatggaa gaacattta ggatcagcta gctaggctac tactactact acttgcttct | 180 |
| gcagttcttg gcaggataat attttagct actactactg tatctcacaa gctagcaaac | 240 |
| gttcttggtt ctagcactat cttgtggagg tggggatct tcctcagcct aaacaggtca | 300 |
| aagaccctat tttgctggcg tgtcctttgg tgtaggatag ctccatttgt tagcttgaat | 360 |
| tgtgtgaaaa atacatgggt tgcaccatca ccgaagtacc caagagtggg ggcaacttgc | 420 |
| ttgcaaggga caaagggcgt gccgtatgag agagatgagc aagtgctgcg tcatttttgg | 480 |
| tttgtcatct tgggtgcaag atcaagcagc aggtgtcaca ggactcacca cagcttgggc | 540 |
| tgtccttggt gccccatgtc caagggtgca ttcattgcac ctcctctagc catggcctaa | 600 |
| tggtgcatac ttctgtgcct caaggactgt tgtctttgaa ccattgatgg atatctatct | 660 |
| gcatccattt gttttaatcc ttggaagcac catgcgtggc ctaaatagtg tgatctgaac | 720 |
| agtgagcatc taagctagcc atggccctcc caagcatttg ccatggtgga agctgcagtg | 780 |
| cagagtcagc atgtggtgtt gttgctgggc cactgttggt gaccgtccta ccaccttttg | 840 |
| catgcagcag cagccagcag cagcttcgga tgccggtgct tgggtctcta ggatggagtt | 900 |
| atggccgggg ggatcacctc acctgagcta gtcatgtgat tcagatatgg gagctcctta | 960 |
| gaccaaacca ttttcttgtt tcacttggcc ttgtgtttgg ttgtcccta gcctttttt | 1020 |
| ggcatgtgag ataaacattc agaggtggaa catggtttat tttgcaggac cacggcgatg | 1080 |

| | |
|---|---:|
| ctgattttttt ttctcaatat taccggtgca ttttcttgt ttagttttg gtacaaaaga | 1140 |
| aaaaaaagct tacgttgcat gttctgtttt aaatttgtat gcttttgttt cttgcaggaa | 1200 |
| taccagggag acgacacctt gcagcttgat cagggacccc gatacgatta gcacccctgg | 1260 |
| atctaccaca aggcgcagcc actcgagttc tcattgcaag gtgcaaacac ccgtgcgcca | 1320 |
| caacattatt ccagcatcag cagagctgga agcgttcttc gctgccgaag agcaacggca | 1380 |
| acgacaggct ttcatcgaca agtacgatct tgctttgctc ttctattatg ttcagtaaat | 1440 |
| atatccctgg atgcattgtg ataatgtcca tggccttgca acttagaaat actataatgg | 1500 |
| tgtattatcg ctgactgaca atttaacttc tttgtcgtaa tcttcaggta taactttgat | 1560 |
| cctgtgaatg actgccctct tcccggccgg tttgaatggg tcaagctaga ctga | 1614 |

<210> SEQ ID NO 5
<211> LENGTH: 568
<212> TYPE: DNA
<213> ORGANISM: Zea mays
<220> FEATURE:
<221> NAME/KEY: misc_feature
<222> LOCATION: (32)..(32)
<223> OTHER INFORMATION: n = A, T, C or G

<400> SEQUENCE: 5

| | |
|---|---:|
| aggttacggg gatcacgtcc cggatgtcgt cnccgcgagc aactcgggga gcgtcccgga | 60 |
| ccgcgagagg agagagacga cgccatcgtc gagccgggcg cacggcggcg agctcagcga | 120 |
| tctggagtcg gatctggtgg ggcggcagaa gactggctgc tcgtcgtcgc cggcgacaac | 180 |
| aacatcggct gcggagctga tcgtgccgcc agcacaggag atccaggaat tcttcgcggc | 240 |
| cgccgaggcg gccatgcca aacgctttgc ttccaagtac aacttcgact tcgtccgcgg | 300 |
| cgtgccctc gacgccggcc ggttcgagtg gacgccaggg gtcagcatct gaagcgagcg | 360 |
| tgcggtgcaa ggtgaagcta ctactagcta gaaagtgagg agaaaaaaag aaagatgcc | 420 |
| gccaaaaaaa cataacggaa aggagaaaag gcaaggagc tttataggct agctaagcta | 480 |
| accaccattc aacatctgcc ttgcttttttt ctccggagta gacttgtaga atgacagcgt | 540 |
| agttatttac tgtttatcca gaggttat | 568 |

<210> SEQ ID NO 6
<211> LENGTH: 543
<212> TYPE: DNA
<213> ORGANISM: Zea mays

<400> SEQUENCE: 6

| | |
|---|---:|
| cgagtcggag gccatgggga ggaataccag ggagacgacg ccctgcagct tgattaactc | 60 |
| tgagatgatc agcactcccg gatccacaac aagatccagc cactcttccc accgcagggt | 120 |
| gaaagctcct cctgtgcacg ccatcccaag ttcaacggag atgaacgagt acttcgctgc | 180 |
| tgaacagcga cgccaacaac aggctttcat tgacaagtac aactttgatc ctgtaaatga | 240 |
| ctgccctctc ccaggcaggt ttgaatgggt gaagctagac tgatagattc agaggacatg | 300 |
| agagcagcag catggaactc acctccgctc cctccaccgc cgcagcgtcg tggcagaggc | 360 |
| gcataccgtc gtgttagctt tgtttctgtt gtaaaaactt agcgttagct tgtagcctta | 420 |
| attgtcgcgt gtcacagtac agaactgatg ctgagttaca gcaccctgat atgatctggt | 480 |
| ccctcaactc caatgtaacc cttaacagct cattctgtaa ggaacctatc atcctgttac | 540 |
| cag | 543 |

<210> SEQ ID NO 7
<211> LENGTH: 1334
<212> TYPE: DNA
<213> ORGANISM: Sorghum bicolor

<400> SEQUENCE: 7

| | | | | | |
|---|---|---|---|---|---|
| atgggcaagt | gcgtcaggat | ccgcggcagc | agcagcaagc | cggccccggc | ggcggccgcc | 60 |
| gaggccgagg | ccgcgtcgtc | gtgcctcacg | ctgcgcagcg | gccgccgcgt | gccgccggtg | 120 |
| gcagcggcgt | gcggcccgcc | gaggaccagc | ggcaggccgc | ggcgccaccg | cgcggggtct | 180 |
| gccctccgac | gatggtgcgg | cgccgccgag | gccgcggaca | gcaggtgca | gcagcgcgcg | 240 |
| tgcggcagcc | cccggcgcgg | gagtgcagca | ggccgggtgc | tcggtctcgg | actcggtgca | 300 |
| cgccggcagc | tctgccacga | cgacgggcgg | acgacggagg | cggaggtgcc | gccgtcgcgg | 360 |
| gcggcagata | tcggcgtcga | cgacgggcgt | ggagactgct | tgagtgagtg | cagttttat | 420 |
| ttattcctgc | tgcctttcat | tcttcggatc | acaattcaca | aaacaaagcc | agtttttagt | 480 |
| gtttttttt | tgcgaggata | agccagtttt | cagttaatcg | caaaggaaa | gccaattttc | 540 |
| agtttcgagg | aaatttacga | aacaatatat | atcatatact | ctctccattc | caaattgtaa | 600 |
| gtcattacaa | gaatcttgga | gagtcaaact | tttctaagtt | tgaccaaatt | tatattataa | 660 |
| aataataata | attatgatac | taactaagta | tcattagatt | ctttcttaat | tatattttaa | 720 |
| tagtatactc | actttacgtt | ataaatctta | gtattttct | ttataatttt | ggtcaaacgt | 780 |
| gaaaatgctt | tgactctta | agattcttaa | aatgatttac | aatttgggat | ggagagagta | 840 |
| tttgcacagg | ttattttttt | ttttgagca | tgtcaagtta | tatattcatc | aggacacaat | 900 |
| cgttaattaa | ccagttgttt | ttaatgcttt | caaatcgtgt | ttatatatat | acatatataa | 960 |
| gcagaccaaa | gacgcccctg | atgaccggcg | acgactgcga | cgcggccgtg | gtgaaagtga | 1020 |
| aggcgaaaca | cgagaacgag | agccgctgca | ggggcctcgt | cgccgccaga | cgccgtcgcc | 1080 |
| accgccgccg | ccgccgccgc | cgccgacgga | agccgagata | gaggccttct | tcgcgggcgg | 1140 |
| cggagctcgc | cgagcgccgg | cgatttgcag | aggcgtaagc | accacggcgt | ttgggacgtt | 1200 |
| ggtgtactgt | aatctagctt | gtacaagtcg | ttggctgacg | ggagctcggc | acgccttcct | 1260 |
| gcaggtacaa | ttacgacgtt | gccctcgact | gcccgttgga | agggcgcttc | gaatggacgc | 1320 |
| cggtgaacac | gtga | | | | | 1334 |

<210> SEQ ID NO 8
<211> LENGTH: 595
<212> TYPE: DNA
<213> ORGANISM: Pinus taeda
<220> FEATURE:
<221> NAME/KEY: misc_feature
<222> LOCATION: (520)..(520)
<223> OTHER INFORMATION: n = A, T, C or G
<220> FEATURE:
<221> NAME/KEY: misc_feature
<222> LOCATION: (531)..(531)
<223> OTHER INFORMATION: n = A, T, C or G
<220> FEATURE:
<221> NAME/KEY: misc_feature
<222> LOCATION: (537)..(537)
<223> OTHER INFORMATION: n = A, T, C or G
<220> FEATURE:
<221> NAME/KEY: misc_feature
<222> LOCATION: (574)..(574)
<223> OTHER INFORMATION: n = A, T, C or G
<220> FEATURE:
<221> NAME/KEY: misc_feature
<222> LOCATION: (584)..(584)
<223> OTHER INFORMATION: n = A, T, C or G
<220> FEATURE:

| <221> NAME/KEY: misc_feature |
| <222> LOCATION: (594)..(594) |
| <223> OTHER INFORMATION: n = A, T, C or G |

<400> SEQUENCE: 8

| gcaaaacgaa ggtaggagtg ctccaacctc acatgaaatg gaggaattct ttgctggggc | 60 |
| agagcaacag caacaaaggc tgttcataga aaggtacaat tatgatcctg tcaatgactt | 120 |
| gccccttttct ggacggtatg agtgggtcag gttgagacca tgagagtagc gtcatctctt | 180 |
| cagactgggc aaaatcactt acttattgtt gaagtgactt cccttcacat atctttttg | 240 |
| gtcaaaatga aaaatacaaa ggaagaggca tttcctgcac atcatttatt agttccagtc | 300 |
| agtgcagact gtgaagattg ttacagaaat gtagctgtat gatgtcaatg tataatatgg | 360 |
| gagagttggg cactttcagt tttgtacaga ttcttactgg gatattctcc ttttaaacag | 420 |
| aatccccaag catctgtagg aaaaaatgat gcctgttttg ttcatggatc acttactgca | 480 |
| atcaaccgcc ttgcctcgtt tcaatgaaac ttttttgacn ccaatctttc ngctgtntat | 540 |
| cccccgggtg gttactgctc actcattgta aacncctcga ttcnctacaa aaana | 595 |

<210> SEQ ID NO 9
<211> LENGTH: 1242
<212> TYPE: DNA
<213> ORGANISM: Oryza sativa

<400> SEQUENCE: 9

| ggcacgaggc ggcgcagatg ggcaagtaca tgaggaagtt cagggggggcc acggggagg | 60 |
| agttggccgc catggaggtc acgcaggtgg ttggcgtccg gacgaggtcg aggtcggcag | 120 |
| cggcggcggg cgcgacgacg acgaaggtgc aggcggcgtc ggcggcgtcc accaggagga | 180 |
| ggaaggcgct gctgccgacg gcggtcgtgg ggactactcg ccgtgacggc gggagctgct | 240 |
| acctccagct gaggagccgc atgctgttca tggccccgcc gaggccggcg ccggccgcga | 300 |
| gggctccggt tgtagcggag gcggcgggtt ccgggaacgg agcggcggcg catgcggcgg | 360 |
| ctggcctctc gcgttgctcc agcacggcgt cgtccgtgga cgcggcggct caggacagga | 420 |
| gcctcgcgtg ccgctccgac gtcgcggagg caggcagcga gcatgtcccg gagggctccg | 480 |
| cgagcgactc ggcgagcggc cgtgaccgcg agaggagaga aacaactcca tcaagctttc | 540 |
| tccccggcga ggtgagcgat ctggagtcgg atctggctgg aggacagaag cgcagccgtc | 600 |
| cactaccttc tgcggcaaca gcctcagcac agcaagccac gcggccgaag attccgccgg | 660 |
| ccgccgagat cgaggcgttc ttcgcggcgg ccgaggaggc tgaggccaag cgcttcgccg | 720 |
| ccaagtacaa cttcgacgtc gttcgcggcg tgccctcga cgccggtcgg ttcgagtgga | 780 |
| ctccggtggt cagcagccga agctgaagcg agcgtgcaga ttaagcggaa gctagaaagg | 840 |
| aaggtacagg ggggcgccgt gtagaaaggg aaggcgagct agagagagga gaagaagaag | 900 |
| aaaagatgct catccaaagg gaataaacgg gaaaagtggg agactacaaa aaaagaagca | 960 |
| ttatagccta acaaccaccg attcgactct ttttctttc acattttctt tgcattttta | 1020 |
| ctcttactgt gtactagaaa gtagtagcag tagtaaacta gtaattcgtc ccagtattta | 1080 |
| tcagaggttt atctcgatag gaatagatat attatcccct tactgtaatt gcctccatct | 1140 |
| tgtatttgga tggaaattaa atttactgta cagcagcagc agctgttctg caagtttaag | 1200 |
| ttaaccatca ccgttttatt acttaaaaaa aaaaaaaaaa aa | 1242 |

<210> SEQ ID NO 10
<211> LENGTH: 262

<212> TYPE: PRT
<213> ORGANISM: Oryza sativa

<400> SEQUENCE: 10

Met Gly Lys Tyr Met Arg Lys Phe Arg Gly Ala Thr Gly Glu Glu Leu
1               5                   10                  15

Ala Ala Met Glu Val Thr Gln Val Val Gly Val Arg Thr Arg Ser Arg
            20                  25                  30

Ser Ala Ala Ala Gly Ala Thr Thr Lys Val Gln Ala Ala Ser
        35                  40                  45

Ala Ala Ser Thr Arg Arg Arg Lys Ala Leu Leu Pro Thr Ala Val Val
    50                  55                  60

Gly Thr Thr Arg Arg Asp Gly Gly Ser Cys Tyr Leu Gln Leu Arg Ser
65                  70                  75                  80

Arg Met Leu Phe Met Ala Pro Pro Arg Pro Ala Pro Ala Ala Arg Ala
                85                  90                  95

Pro Val Val Ala Glu Ala Ala Gly Ser Gly Asn Gly Ala Ala Ala His
            100                 105                 110

Ala Ala Ala Gly Leu Ser Arg Cys Ser Ser Thr Ala Ser Ser Val Asp
        115                 120                 125

Ala Ala Ala Gln Asp Arg Ser Leu Ala Cys Arg Ser Asp Val Ala Glu
    130                 135                 140

Ala Gly Ser Glu His Val Pro Glu Gly Ser Ala Ser Asp Ser Ala Ser
145                 150                 155                 160

Gly Arg Asp Arg Glu Arg Arg Glu Thr Thr Pro Ser Ser Phe Leu Pro
                165                 170                 175

Gly Glu Val Ser Asp Leu Glu Ser Asp Leu Ala Gly Gly Gln Lys Arg
            180                 185                 190

Ser Arg Pro Leu Pro Ser Ala Ala Thr Ala Ser Ala Gln Gln Ala Thr
        195                 200                 205

Arg Pro Lys Ile Pro Pro Ala Ala Glu Ile Glu Ala Phe Phe Ala Ala
    210                 215                 220

Ala Glu Glu Ala Glu Ala Lys Arg Phe Ala Ala Lys Tyr Asn Phe Asp
225                 230                 235                 240

Val Val Arg Gly Val Pro Leu Asp Ala Gly Arg Phe Glu Trp Thr Pro
                245                 250                 255

Val Val Ser Ser Arg Ser
            260

<210> SEQ ID NO 11
<211> LENGTH: 22
<212> TYPE: PRT
<213> ORGANISM: Oryza sativa

<400> SEQUENCE: 11

Tyr Asn Tyr Asp Ile Ala Leu Asp Arg Pro Leu Gln Gly Arg Tyr Glu
1               5                   10                  15

Trp Glu Pro Val Ser Thr
            20

<210> SEQ ID NO 12
<211> LENGTH: 87
<212> TYPE: PRT
<213> ORGANISM: Oryza sativa

<400> SEQUENCE: 12

Leu Ile Thr Leu Ser Val Cys His Thr Leu Thr Leu Thr Leu Ile Asn

```
                1               5                  10                 15
Ser Cys Phe Tyr Ser Leu Gln Phe Arg Lys Ser Leu Lys Pro Asn Ser
                20                 25                 30

Cys Ser Arg Glu Val Ala Ala Glu His Ala Gly Glu His Lys His Asn
                35                 40                 45

Pro Ala Ala Ala Ala Ala Gly Arg Arg Pro Pro Leu Ser Pro Pro
            50                  55                 60

Glu Ala Glu Ile Glu Ala Phe Phe Ala Ala Ala Glu Leu Ala Glu Arg
65                  70                 75                 80

Arg Arg Phe Ala Glu Lys Tyr
                85

<210> SEQ ID NO 13
<211> LENGTH: 90
<212> TYPE: PRT
<213> ORGANISM: Oryza sativa

<400> SEQUENCE: 13

Arg Asn Thr Arg Glu Thr Thr Pro Cys Ser Leu Ile Arg Asp Pro Asp
1               5                  10                 15

Thr Ile Ser Thr Pro Gly Ser Thr Thr Arg Arg Ser His Ser Ser Ser
                20                 25                 30

His Cys Lys Val Gln Thr Pro Val Arg His Asn Ile Ile Pro Ala Ser
                35                 40                 45

Ala Glu Leu Glu Ala Phe Phe Ala Ala Glu Glu Gln Arg Gln Arg Gln
            50                  55                 60

Ala Phe Ile Asp Lys Tyr Asn Phe Asp Pro Val Asn Asp Cys Pro Leu
65                  70                 75                 80

Pro Gly Arg Phe Glu Trp Val Lys Leu Asp
                85                 90

<210> SEQ ID NO 14
<211> LENGTH: 116
<212> TYPE: PRT
<213> ORGANISM: Zea mays
<220> FEATURE:
<221> NAME/KEY: misc_feature
<222> LOCATION: (11)..(11)
<223> OTHER INFORMATION: Xaa = any amino acid

<400> SEQUENCE: 14

Gly Tyr Gly Asp His Val Pro Asp Val Val Xaa Ala Ser Asn Ser Gly
1               5                  10                 15

Ser Val Pro Asp Arg Glu Arg Glu Thr Thr Pro Ser Ser Ser Arg
                20                 25                 30

Ala His Gly Gly Glu Leu Ser Asp Leu Glu Ser Asp Leu Val Gly Arg
            35                  40                 45

Gln Lys Thr Gly Cys Ser Ser Pro Ala Thr Thr Ser Ala Ala
            50                  55                 60

Glu Leu Ile Val Pro Pro Ala Gln Glu Ile Gln Glu Phe Phe Ala Ala
65                  70                 75                 80

Ala Glu Ala Ala His Ala Lys Arg Phe Ala Ser Lys Tyr Asn Phe Asp
                85                 90                 95

Phe Val Arg Gly Val Pro Leu Asp Ala Gly Arg Phe Glu Trp Thr Pro
                100                105                110

Gly Val Ser Ile
            115
```

<210> SEQ ID NO 15
<211> LENGTH: 93
<212> TYPE: PRT
<213> ORGANISM: Zea mays

<400> SEQUENCE: 15

Glu Ser Glu Ala Met Gly Arg Asn Thr Arg Glu Thr Pro Cys Ser
1               5                   10                  15

Leu Ile Asn Ser Glu Met Ile Ser Thr Pro Gly Ser Thr Thr Arg Ser
            20                  25                  30

Ser His Ser Ser His Arg Arg Val Lys Ala Pro Pro Val His Ala Ile
        35                  40                  45

Pro Ser Ser Thr Glu Met Asn Glu Tyr Phe Ala Ala Glu Gln Arg Arg
    50                  55                  60

Gln Gln Gln Ala Phe Ile Asp Lys Tyr Asn Phe Asp Pro Val Asn Asp
65                  70                  75                  80

Cys Pro Leu Pro Gly Arg Phe Glu Trp Val Lys Leu Asp
                85                  90

<210> SEQ ID NO 16
<211> LENGTH: 108
<212> TYPE: PRT
<213> ORGANISM: Sorghum bicolor

<400> SEQUENCE: 16

Val Phe Asn Ala Phe Lys Ser Cys Leu Tyr Ile Tyr Ile Tyr Lys Gln
1               5                   10                  15

Thr Lys Asp Ala Pro Asp Asp Arg Arg Arg Leu Arg Arg Gly Arg Gly
            20                  25                  30

Glu Ser Glu Gly Glu Thr Arg Glu Arg Glu Pro Leu Gln Gly Pro Arg
        35                  40                  45

Arg Arg Gln Thr Pro Ser Pro Pro Pro Pro Pro Pro Pro Thr
    50                  55                  60

Glu Ala Glu Ile Glu Ala Phe Phe Ala Ala Ala Glu Leu Ala Glu Arg
65                  70                  75                  80

Arg Arg Phe Ala Glu Ala Tyr Asn Tyr Asp Val Ala Leu Asp Cys Pro
                85                  90                  95

Leu Glu Gly Arg Phe Glu Trp Thr Pro Val Asn Thr
            100                 105

<210> SEQ ID NO 17
<211> LENGTH: 53
<212> TYPE: PRT
<213> ORGANISM: Pinus taeda

<400> SEQUENCE: 17

Gln Asn Glu Gly Arg Ser Ala Pro Thr Ser His Glu Met Glu Glu Phe
1               5                   10                  15

Phe Ala Gly Ala Glu Gln Gln Gln Gln Arg Leu Phe Ile Glu Arg Tyr
            20                  25                  30

Asn Tyr Asp Pro Val Asn Asp Leu Pro Leu Ser Gly Arg Tyr Glu Trp
        35                  40                  45

Val Arg Leu Arg Pro
    50

<210> SEQ ID NO 18
<211> LENGTH: 8
<212> TYPE: PRT

```
<213> ORGANISM: Artificial sequence
<220> FEATURE:
<223> OTHER INFORMATION: consensus ICK motif 1
<220> FEATURE:
<221> NAME/KEY: misc_feature
<222> LOCATION: (2)..(3)
<223> OTHER INFORMATION: Xaa = any amino acid
<220> FEATURE:
<221> NAME/KEY: misc_feature
<222> LOCATION: (7)..(7)
<223> OTHER INFORMATION: Xaa = any amino acid

<400> SEQUENCE: 18

Phe Xaa Xaa Lys Tyr Asn Xaa Asp
1               5

<210> SEQ ID NO 19
<211> LENGTH: 8
<212> TYPE: PRT
<213> ORGANISM: Artificial sequence
<220> FEATURE:
<223> OTHER INFORMATION: consensus ICK motif 2
<220> FEATURE:
<221> NAME/KEY: misc_feature
<222> LOCATION: (1)..(1)
<223> OTHER INFORMATION: Xaa = any amino acid
<220> FEATURE:
<221> NAME/KEY: misc_feature
<222> LOCATION: (3)..(3)
<223> OTHER INFORMATION: Xaa = any amino acid
<220> FEATURE:
<221> NAME/KEY: misc_feature
<222> LOCATION: (6)..(6)
<223> OTHER INFORMATION: Xaa = any amino acid

<400> SEQUENCE: 19

Xaa Leu Xaa Gly Arg Xaa Glu Trp
1               5

<210> SEQ ID NO 20
<211> LENGTH: 10
<212> TYPE: PRT
<213> ORGANISM: Artificial sequence
<220> FEATURE:
<223> OTHER INFORMATION: consensus ICK motif 3
<220> FEATURE:
<221> NAME/KEY: misc_feature
<222> LOCATION: (2)..(2)
<223> OTHER INFORMATION: Xaa = any amino acid
<220> FEATURE:
<221> NAME/KEY: misc_feature
<222> LOCATION: (4)..(4)
<223> OTHER INFORMATION: Xaa = any amino acid
<220> FEATURE:
<221> NAME/KEY: misc_feature
<222> LOCATION: (7)..(9)
<223> OTHER INFORMATION: Xaa = any amino acid

<400> SEQUENCE: 20

Glu Xaa Glu Xaa Phe Phe Xaa Xaa Xaa Glu
1               5                   10

<210> SEQ ID NO 21
<211> LENGTH: 8
<212> TYPE: PRT
<213> ORGANISM: Artificial sequence
<220> FEATURE:
<223> OTHER INFORMATION: consensus ICK motif 4
<220> FEATURE:
<221> NAME/KEY: misc_feature
<222> LOCATION: (2)..(2)
<223> OTHER INFORMATION: Xaa = any amino acid
```

```
<400> SEQUENCE: 21

Tyr Xaa Gln Leu Arg Ser Arg Arg
1               5

<210> SEQ ID NO 22
<211> LENGTH: 9
<212> TYPE: PRT
<213> ORGANISM: Artificial sequence
<220> FEATURE:
<223> OTHER INFORMATION: consensus ICK motif 5
<220> FEATURE:
<221> NAME/KEY: misc_feature
<222> LOCATION: (5)..(6)
<223> OTHER INFORMATION: Xaa = any amino acid
<220> FEATURE:
<221> NAME/KEY: misc_feature
<222> LOCATION: (8)..(9)
<223> OTHER INFORMATION: Xaa = any amino acid

<400> SEQUENCE: 22

Met Gly Lys Tyr Xaa Xaa Lys Xaa Xaa
1               5

<210> SEQ ID NO 23
<211> LENGTH: 8
<212> TYPE: PRT
<213> ORGANISM: Artificial sequence
<220> FEATURE:
<223> OTHER INFORMATION: consensus ICK motif 6
<220> FEATURE:
<221> NAME/KEY: misc_feature
<222> LOCATION: (2)..(2)
<223> OTHER INFORMATION: Xaa = any amino acid

<400> SEQUENCE: 23

Ser Xaa Gly Val Arg Thr Arg Ala
1               5

<210> SEQ ID NO 24
<211> LENGTH: 4
<212> TYPE: PRT
<213> ORGANISM: Artificial sequence
<220> FEATURE:
<223> OTHER INFORMATION: Cy-box
<220> FEATURE:
<221> NAME/KEY: misc_feature
<222> LOCATION: (2)..(3)
<223> OTHER INFORMATION: Xaa = any amino acid

<400> SEQUENCE: 24

Arg Xaa Xaa Phe
1

<210> SEQ ID NO 25
<211> LENGTH: 24
<212> TYPE: DNA
<213> ORGANISM: Artificial sequence
<220> FEATURE:
<223> OTHER INFORMATION: probe or primer

<400> SEQUENCE: 25
taactcgatc cccagcctct ccca                                            24

<210> SEQ ID NO 26
<211> LENGTH: 24
<212> TYPE: DNA
<213> ORGANISM: Artificial sequence
<220> FEATURE:
<223> OTHER INFORMATION: probe or primer
```

```
<400> SEQUENCE: 26
tacaattacg acattgccct cgac                                          24

<210> SEQ ID NO 27
<211> LENGTH: 24
<212> TYPE: DNA
<213> ORGANISM: Artificial sequence
<220> FEATURE:
<223> OTHER INFORMATION: probe or primer

<400> SEQUENCE: 27
ccgccgagat cgaggcgttc ttcg                                          24

<210> SEQ ID NO 28
<211> LENGTH: 24
<212> TYPE: DNA
<213> ORGANISM: Artificial sequence
<220> FEATURE:
<223> OTHER INFORMATION: probe or primer

<400> SEQUENCE: 28
aaacctctga taaatactgg gacg                                          24

<210> SEQ ID NO 29
<211> LENGTH: 24
<212> TYPE: DNA
<213> ORGANISM: Artificial sequence
<220> FEATURE:
<223> OTHER INFORMATION: probe or primer

<400> SEQUENCE: 29
ctgtcacaca ctcacactca cact                                          24

<210> SEQ ID NO 30
<211> LENGTH: 20
<212> TYPE: DNA
<213> ORGANISM: Artificial sequence
<220> FEATURE:
<223> OTHER INFORMATION: probe or primer

<400> SEQUENCE: 30
cgaagaacgc ctcgatctcc                                               20

<210> SEQ ID NO 31
<211> LENGTH: 25
<212> TYPE: DNA
<213> ORGANISM: Artificial sequence
<220> FEATURE:
<223> OTHER INFORMATION: probe or primer

<400> SEQUENCE: 31
gaataccagg gagacgacac cttgc                                         25

<210> SEQ ID NO 32
<211> LENGTH: 25
<212> TYPE: DNA
<213> ORGANISM: Artificial sequence
<220> FEATURE:
<223> OTHER INFORMATION: probe or primer

<400> SEQUENCE: 32
tcagtctagc ttgacccatt caaac                                         25

<210> SEQ ID NO 33
```

-continued

```
<211> LENGTH: 21
<212> TYPE: DNA
<213> ORGANISM: Artificial sequence
<220> FEATURE:
<223> OTHER INFORMATION: probe or primer

<400> SEQUENCE: 33
agggatgttt aataccacta c                                              21

<210> SEQ ID NO 34
<211> LENGTH: 21
<212> TYPE: DNA
<213> ORGANISM: Artificial sequence
<220> FEATURE:
<223> OTHER INFORMATION: probe or primer

<400> SEQUENCE: 34
gcacagttga agtgaacttg c                                              21

<210> SEQ ID NO 35
<211> LENGTH: 26
<212> TYPE: DNA
<213> ORGANISM: Artificial sequence
<220> FEATURE:
<223> OTHER INFORMATION: probe or primer

<400> SEQUENCE: 35
cgttgtcaat atcctggaaa ttttgc                                         26

<210> SEQ ID NO 36
<211> LENGTH: 26
<212> TYPE: DNA
<213> ORGANISM: Artificial sequence
<220> FEATURE:
<223> OTHER INFORMATION: probe or primer

<400> SEQUENCE: 36
ctgccattct ttagagggga tgcttg                                         26

<210> SEQ ID NO 37
<211> LENGTH: 12
<212> TYPE: PRT
<213> ORGANISM: Artificial sequence
<220> FEATURE:
<223> OTHER INFORMATION: Tag.100 epitope

<400> SEQUENCE: 37

Glu Glu Thr Ala Arg Phe Gln Pro Gly Tyr Arg Ser
1               5                   10

<210> SEQ ID NO 38
<211> LENGTH: 10
<212> TYPE: PRT
<213> ORGANISM: Artificial sequence
<220> FEATURE:
<223> OTHER INFORMATION: c-myc epitope

<400> SEQUENCE: 38

Glu Gln Lys Leu Ile Ser Glu Glu Asp Leu
1               5                   10

<210> SEQ ID NO 39
<211> LENGTH: 7
<212> TYPE: PRT
<213> ORGANISM: Artificial sequence
<220> FEATURE:
<223> OTHER INFORMATION: FLAG-epitope
```

<400> SEQUENCE: 39

Asp Tyr Lys Asp Asp Asp Lys
1               5

<210> SEQ ID NO 40
<211> LENGTH: 9
<212> TYPE: PRT
<213> ORGANISM: Artificial sequence
<220> FEATURE:
<223> OTHER INFORMATION: HA-epitope

<400> SEQUENCE: 40

Tyr Pro Tyr Asp Val Pro Asp Tyr Ala
1               5

<210> SEQ ID NO 41
<211> LENGTH: 12
<212> TYPE: PRT
<213> ORGANISM: Artificial sequence
<220> FEATURE:
<223> OTHER INFORMATION: protein C epitope

<400> SEQUENCE: 41

Glu Asp Gln Val Asp Pro Arg Leu Ile Asp Gly Lys
1               5                   10

<210> SEQ ID NO 42
<211> LENGTH: 11
<212> TYPE: PRT
<213> ORGANISM: Artificial sequence
<220> FEATURE:
<223> OTHER INFORMATION: VSV epitope

<400> SEQUENCE: 42

Tyr Thr Asp Ile Glu Met Asn Arg Leu Gly Lys
1               5                   10

<210> SEQ ID NO 43
<211> LENGTH: 1067
<212> TYPE: DNA
<213> ORGANISM: Oryza sativa

<400> SEQUENCE: 43

```
gaaaccctag cccccteccca tcccgagtcc cgaccgccat gggcaagtac atgcgcaagg      60
ccaaggtggt ggtctccggc gaggtggtgg ccgccgccgt catggagctc gccgcggcgc     120
cgctcggggt gcgcacccgc gcccgctccc tcgcgctgca agaggcag ggcggggagt       180
acctcgagct caggagccgc aggctcgaga agctccctcc tccccgccg ccgccgccga     240
ggaggagggc gacggctgcg gctgcgactg ctgatgcgac ggcgacggag agcgcggagg     300
cggaggtgtc gttcgggggg gagaacgtcc tcgagctgga ggccatggaa aggaatacca     360
gggagacgac accttgcagc ttgatcaggg accccgatac gattagcacc cctggatcta     420
ccacaaggcg cagccactcg agttctcatt gcaaggtgca acacccgtg cgccacaaca      480
ttattccagc atcagcagag ctggaagcgt tcttcgcygc cgaagagcaa cggcaacgac     540
aggctttcat cgacaagtat aactttgatc ctgtgaatga ctgccctctt cccggccgrt     600
ttgaatgggt caagctagac tgatagattt tcaggaaaag aagggcacca tggacctctc     660
tgctccctcc acagtagtag cgtggcagag gcgcttaccg tcaagttagc tttgatcctg     720
ttgtaaaaat ttagggttag cctgtagact caatggtcaa tgtgaacata cagaactgat     780
```

-continued

```
gctgagttac aaccctaatc cctcaactac aatgtaaccc ttaacagctc attctgtaag    840
gaaccacctc ctcctctagg gcctagctag ccttatcatc tgttattacc agttgctgga    900
ttaatgaagt tagatctaga tattgtgtca cagtttaacc tgttgtgtgt gtggtggtag    960
cattggcatt ggcaatgggg tatggcagtg tgtgtgtggt gctgcactgc acctcccgaa   1020
gtgctgtaat ttttgtctat acttctgcta aaaaaaaaaa aaaaaaa                 1067
```

<210> SEQ ID NO 44
<211> LENGTH: 194
<212> TYPE: PRT
<213> ORGANISM: Oryza sativa

<400> SEQUENCE: 44

```
Met Gly Lys Tyr Met Arg Lys Ala Lys Val Val Ser Gly Glu Val
1               5                   10                  15

Val Ala Ala Val Met Glu Leu Ala Ala Pro Leu Gly Val Arg
            20                  25                  30

Thr Arg Ala Arg Ser Leu Ala Leu Gln Lys Arg Gln Gly Gly Glu Tyr
            35                  40                  45

Leu Glu Leu Arg Ser Arg Arg Leu Glu Lys Leu Pro Pro Pro Pro
        50                  55                  60

Pro Pro Pro Arg Arg Arg Ala Thr Ala Ala Ala Thr Ala Asp Ala
65                  70                  75                  80

Thr Ala Thr Glu Ser Ala Glu Ala Glu Val Ser Phe Gly Gly Glu Asn
                85                  90                  95

Val Leu Glu Leu Glu Ala Met Glu Arg Asn Thr Arg Glu Thr Thr Pro
            100                 105                 110

Cys Ser Leu Ile Arg Asp Pro Asp Thr Ile Ser Thr Pro Gly Ser Thr
        115                 120                 125

Thr Arg Arg Ser His Ser Ser Ser His Cys Lys Val Gln Thr Pro Val
    130                 135                 140

Arg His Asn Ile Ile Pro Ala Ser Ala Glu Leu Glu Ala Phe Phe Ala
145                 150                 155                 160

Ala Glu Glu Gln Arg Gln Arg Gln Ala Phe Ile Asp Lys Tyr Asn Phe
                165                 170                 175

Asp Pro Val Asn Asp Cys Pro Leu Pro Gly Arg Phe Glu Trp Val Lys
            180                 185                 190

Leu Asp
```

<210> SEQ ID NO 45
<211> LENGTH: 3364
<212> TYPE: DNA
<213> ORGANISM: Oryza sativa

<400> SEQUENCE: 45

```
gaaaccctag ccccctcccc tcccgagtcc cgaccgccat gggcaagtac atgcgcaagg     60
ccaaggtggt ggtctccggc gaggtggtgg ccgccgccgt catggagctc gccgcggcgc    120
cgctcggggt gcgcacccgc gcccgctccc tcgcgctgca aagaggcag ggcggggagt    180
acctcgagct caggagccgc aggctcgaga agctccctcc tccccgccg ccgccgcga    240
ggaggagggc gacggctgcg gctgcgactg ctgatgcgac ggcggcgag agcgcggagg    300
cggaggtgtc gttcggggg gagaacgtcc tcgagctgga ggccatggaa aggtggggat    360
tctctctctc ttcttattgt gcgattcttt ttttgttttt cgtgggtttc ttggttggat    420
tgattggggg aatcgcgtga ttagggttca gggtttaagc accgtacggg agttcttggg    480
```

```
gttcgatgtt tctatccggt tttcgcatc ggaaaatttt ggggattttt tttcggtgcg    540
attgtggcgc tcggaattcc tgtggccagt tttggggttt cgaaagtatc gaaatggagg    600
cgaggaatct ttttttttc catcacacgc ggttgtaaag ccccgatgct tcttggtgg     660 gattcttgtc cctttgctaa ttgagacatg caattcgtgc tttccttgtt gcctaaattt    720 gttcttttc catgtttctt gtggcgatac agccttttct ttttgccaat tcttgtccc     780 ttagcttgtt tacaagttag aacccatttt aacttctttt gaagaaggga aaaaagaag    840 aagagaaggt gttcccaagt tttaatccaa atggttgcaa gaaccacttc tttgccccccc   900 aaatttacct cgaagaatcc ccccaaattt gttattgttt tggatgataa aaaggtagga    960
actgtgcagt agtgctcaag ctctcaactc aaatcccaat tgaaacttga tcaattgatt   1020 gagccccct cttagtgggg ttactcccag tggccatggc ctcctgcttt tccttagtgg    1080
aagggaaaag cagcatcctt tccctcctgt tctttgtgtt ttgtttgggg ggtagggacc   1140
cctctcaatc ttttaccaat caaaagccct cacctttgc aagaaatttc tctcataaac     1200
atccttccca aaggcacccc ccatctcacc acccacctca aggcctcatt cttgcaacta   1260
actagcctgt cacttctctg ggttctggaa gggtgatgaa atggcatgcc ttggtaaaac   1320
catcttcctg ggccatgccc ccaaattgtc accaccatta aatgtttgag gtgaaaggag   1380
ggggtcctcc ccctccccac aagtactaga agttgatttg ttggtgatct ttggttcaag   1440 ctaggggggat ggaagaacat tttaggatca gctagctagg ctactactac tactacttgc   1500
ttctgcagtt cttggcagga taatattttt agctactact actgtatctc acaagctagc   1560
aaacgttctt ggttctagca ctatcttgtg gaggtgggg atcttcctca gcctaaacag    1620
gtcaaagacc ctatttttgct ggcgtgtcct ttggtgtagg atagctccat ttgttagctt   1680
gaattgtgtg aaaaatacat gggttgcacc atcaccgaag tacccaagag tgggggcaac   1740
ttgcttgcaa gggacaaagg gcgtgccgta tgagagagat gagcaagtgc tgcgtcattt   1800
ttggtttgtc atcttgggtg caagatcaag cagcaggtgt cacaggactc accacagctt   1860
gggctgtcct tggtgcccca tgtccaaggg tgcattcatt gcacctcctc tagccatggc   1920
ctaatggtgc atacttctgt gcctcaagga ctgttgtctt tgaaccattg atggatatct   1980
atctgcatcc atttgttta atccttggaa gcaccatgcg tggcctaaat agtgtgatct   2040
gaacagtgag catctaagct agccatggcc ctcccaagca tttgccatgg tggaagctgc   2100
agtgcagagt cagcatgtgg tgttgttgct gggccactgt tggtgaccgt cctaccacct   2160
tttgcatgca gcagcagcca gcagcagctt cggatgccgg tgcttgggtc tctaggatgg   2220
agttatggcc ggggggatca cctcacctga gctagtcatg tgattcagat atgggagctc   2280
cttagaccaa accattttct tgtttcactt ggccttgtgt ttggttgtcc cctagccttt   2340
ttttggcatg tgagataaac attcagaggt ggaacatggt ttattttgca ggaccacggc   2400
gatgctgatt tttttctca atattaccgg tgcattttc ttgtttagtt tttggtacaa    2460
aagaaaaaaa agcttacgtt gcatgttctg ttttaaattt gtatgctttt gtttcttgca   2520
ggaataccag ggagacgaca ccttgcagct tgatcaggga ccccgatacg attagcaccc   2580
ctggatctac cacaaggcgc agccactcga gttctcattg caaggtgcaa acacccgtgc   2640
gccacaacat tattccagca tcagcagagc tggaagcgtt cttcgctgcc gaagagcaac   2700
ggcaacgaca ggctttcatc gacaagtacg atcttgcttt gctcttctat tatgttcagt   2760
aaatatatcc ctggatgcat tgtgataatg tccatggcct tgcaacttag aaatactata   2820
```

-continued

```
atggtgtatt atcgctgact gacaatttaa cttctttgtc gtaatcttca ggtataactt      2880
tgatcctgtg aatgactgcc ctcttcccgg ccggtttgaa tgggtcaagc tagactgata      2940
gattttcagg aaaagaaggg caccatggac ctctctgctc cctccacagt agtagcgtgg      3000
cagaggcgct taccgtcaag ttagctttga tcctgttgta aaaatttagg gttagcctgt      3060
agactcaatg gtcaatgtga acatacagaa ctgatgctga gttacaaccc taatccctca      3120
actacaatgt aacccttaac agctcattct gtaaggaacc acctcctcct ctagggccta      3180
gctagcctta tcatctgtta ttaccagttg ctggattaat gaagttagat ctagatattg      3240
tgtcacagtt taacctgttc tgtgtgtggt ggtagcattg gcattggcaa tggggtatgg      3300
cagtgtgtgt gtggtgctgc actgcacctc ccgaagtgct gtaattttg tctatacttc       3360 tgct                                                                  3364
```

<210> SEQ ID NO 46
<211> LENGTH: 30
<212> TYPE: DNA
<213> ORGANISM: Artificial sequence
<220> FEATURE:
<223> OTHER INFORMATION: probe or primer

<400> SEQUENCE: 46
gaattccttc tacatcggct taggtgtagc     30

<210> SEQ ID NO 47
<211> LENGTH: 30
<212> TYPE: DNA
<213> ORGANISM: Artificial sequence
<220> FEATURE:
<223> OTHER INFORMATION: probe or primer

<400> SEQUENCE: 47
ccatggtgtt gttggattct actactatgc     30

<210> SEQ ID NO 48
<211> LENGTH: 30
<212> TYPE: DNA
<213> ORGANISM: Artificial sequence
<220> FEATURE:
<223> OTHER INFORMATION: probe or primer

<400> SEQUENCE: 48
gaacaaagat ggtcagccaa tacattgatc     30

<210> SEQ ID NO 49
<211> LENGTH: 30
<212> TYPE: DNA
<213> ORGANISM: Artificial sequence
<220> FEATURE:
<223> OTHER INFORMATION: probe or primer

<400> SEQUENCE: 49
ggccatggct aagctagcta gcaagatgaa     30

<210> SEQ ID NO 50
<211> LENGTH: 30
<212> TYPE: DNA
<213> ORGANISM: Artificial sequence
<220> FEATURE:
<223> OTHER INFORMATION: probe or primer

<400> SEQUENCE: 50
agaagaaaga taaataaccg aaactatttg     30

<210> SEQ ID NO 51
<211> LENGTH: 30
<212> TYPE: DNA
<213> ORGANISM: Artificial sequence
<220> FEATURE:
<223> OTHER INFORMATION: probe or primer

<400> SEQUENCE: 51
ggacatgttt ttgtgggact gaactcaatg                              30

<210> SEQ ID NO 52
<211> LENGTH: 24
<212> TYPE: DNA
<213> ORGANISM: Artificial sequence
<220> FEATURE:
<223> OTHER INFORMATION: probe or primer

<400> SEQUENCE: 52
actccttgtc cctatcgaca cacc                                    24

<210> SEQ ID NO 53
<211> LENGTH: 24
<212> TYPE: DNA
<213> ORGANISM: Artificial sequence
<220> FEATURE:
<223> OTHER INFORMATION: probe or primer

<400> SEQUENCE: 53
ccatggggga cgcctcggca tcca                                    24

<210> SEQ ID NO 54
<211> LENGTH: 681
<212> TYPE: DNA
<213> ORGANISM: Artificial sequence
<220> FEATURE:
<223> OTHER INFORMATION: probe or primer
<220> FEATURE:
<221> NAME/KEY: misc_feature
<222> LOCATION: (355)..(356)
<223> OTHER INFORMATION: n = A, T, C or G

<400> SEQUENCE: 54
atggggaaga agaagaagcg cgacggcgcg gcggcgagga ggcaggcgcg ggtggtggtc    60
ggcggcgtcc gtacgcgggc cgccgtcacg gcgaggaggg tggtggcgag cgcggaggag   120
ggttgtggtt tggtgggccg tggcggtggc ggtggcagtg gcggagacga tggcgagggc   180
ggatgctatc tgcgtctgcg gagcaggagg ctgcccttcg tggcggccgc ggtggtgtcg   240
tcgcggaggg aggaggcgct cggtgattcg gtggcggagg cggcttcgtc gtcgtcgtcg   300
cgggcggtgg aattgttggg ctgttctggt gaggaggagg ctatggccga gaagnngagc   360
gcgacgacgc cgtcgagccg ccggccgccg ggagacgcgg actcgagcga cgcggagtca   420
aaccaggagg ccaagcagca aatgtgccgc cggagttcga cgacctcagc agctgcattt   480
cacgcgggag cgacgacgag gagcttcagg atgatggcac cgccggcggc ggcggcagag   540
atcgaggagt tcctcgccgc tgcggagagg tccgaggccg agcgcttcgc cgccaagtac   600
aacttcgacg tggtgcgcgg cgtgccgctc gacgccggcg gcgccgggcg gttcgaatgg   660
accgcggtgg gcagcggctg a                                           681

<210> SEQ ID NO 55
<211> LENGTH: 226
<212> TYPE: PRT

<213> ORGANISM: Artificial sequence
<220> FEATURE:
<223> OTHER INFORMATION: probe or primer
<220> FEATURE:
<221> NAME/KEY: misc_feature
<222> LOCATION: (119)..(119)
<223> OTHER INFORMATION: Xaa = any amino acid

<400> SEQUENCE: 55

Met Gly Lys Lys Lys Arg Asp Gly Ala Ala Arg Arg Gln Ala
1               5                   10                  15

Arg Val Val Gly Gly Val Arg Thr Arg Ala Ala Val Thr Ala Arg
            20                  25                  30

Arg Val Val Ala Ser Ala Glu Glu Gly Cys Gly Leu Val Gly Arg Gly
        35                  40                  45

Gly Gly Gly Gly Ser Gly Gly Asp Asp Gly Glu Gly Gly Cys Tyr Leu
    50                  55                  60

Arg Leu Arg Ser Arg Arg Leu Pro Phe Val Ala Ala Val Val Ser
65                  70                  75                  80

Ser Arg Arg Glu Glu Ala Leu Gly Asp Ser Val Ala Glu Ala Ala Ser
                85                  90                  95

Ser Ser Ser Ser Arg Ala Val Glu Leu Leu Gly Cys Ser Gly Glu Glu
            100                 105                 110

Glu Ala Met Ala Glu Lys Xaa Ser Ala Thr Thr Pro Ser Ser Arg Arg
        115                 120                 125

Pro Pro Gly Asp Ala Asp Ser Ser Asp Ala Glu Ser Asn Gln Glu Ala
    130                 135                 140

Lys Gln Gln Met Cys Arg Arg Ser Ser Thr Thr Ser Ala Ala Ala Phe
145                 150                 155                 160

His Ala Gly Ala Thr Thr Arg Ser Phe Arg Met Met Ala Pro Pro Ala
                165                 170                 175

Ala Ala Ala Glu Ile Glu Glu Phe Leu Ala Ala Ala Glu Arg Ser Glu
            180                 185                 190

Ala Glu Arg Phe Ala Ala Lys Tyr Asn Phe Asp Val Val Arg Gly Val
        195                 200                 205

Pro Leu Asp Ala Gly Gly Ala Gly Arg Phe Glu Trp Thr Ala Val Gly
    210                 215                 220

Ser Gly
225

<210> SEQ ID NO 56
<211> LENGTH: 1073
<212> TYPE: DNA
<213> ORGANISM: Oryza sativa

<400> SEQUENCE: 56
atggggaaga agaagaagcg cgacggcgcg gcggcgagga ggcaggcgcg ggtggtggtc      60
ggcggcgtcc gtacgcgggc cgccgtcacg gcgaggaggg tggtggcgag cgcggaggag     120
ggttgtggtt tggtgggccg tggcggtggc ggtggcagtg gcggagacga tggcgagggc     180
ggatgctatc tgcgtctgcg gagcaggagg ctgcccttcg tggcggccgc ggtggtgtcg     240
tcgcggaggg aggaggcgct cggtgattcg gtggcggagg cggcttcgtc gtcgtcgtcg     300
cgggcggtgg aattgttggg ctgttctggt gaggaggagg ctatgccgga aaggtgattt       360
gatgagccct agaattcctc gcggctcga gtgctcgatc gcccgcttcc atctcttgct       420
gaatgatgcg gcttgggatg tggtggtttt gcaggtttgc acgcaggcag gcaggatca       480

-continued

```
cgacgaggag agctccgtcg gcgactccgg ctgcggccgc gagaggtgat cgagctcctc    540
tccacgcgtt cttgcttgtc cttgacatga ttaattacaa ccgccgttct ctcaattgaa    600
ttatcgcaat tcaatccagg agcgcgacga cgccgtcgag ccgccggccg ccgggagacg    660
cggactcgag cgacgcggag tcaaaccagg aggccaagca gcaaatgtgc cgccggagtt    720
cgacgacctc agcagctgca tttcacgcgg gagcgacgac gaggagcttc aggatgatgg    780
caccgccggc ggcggcggca gagatcgagg agttcctcgc cgctgcggag aggtccgagg    840
ccgagcgctt cgccgccaag tgagtgctgc atcacatatt gtcgtccgtg cgtcgtgtcg    900
tacatatcgt cgtcgtcgtc aaaatcggcc tcgatcgcga catgcatggc cgcatgggag    960
ctgattaacg tgcgctcctc ctcctcaggt acaacttcga cgtggtgcgc ggcgtgccgc   1020
tcgacgccgg cggcgccggg cggttcgaat ggaccgcggt gggcagcggc tga          1073

<210> SEQ ID NO 57
<211> LENGTH: 59
<212> TYPE: DNA
<213> ORGANISM: Artificial sequence
<220> FEATURE:
<223> OTHER INFORMATION: sense primer OsICK5

<400> SEQUENCE: 57
ggggacaagt ttgtacaaaa aagcaggctt cacaatgggg aagaagaaga agcgcgacg     59

<210> SEQ ID NO 58
<211> LENGTH: 49
<212> TYPE: DNA
<213> ORGANISM: Artificial sequence
<220> FEATURE:
<223> OTHER INFORMATION: antisense primer OsICK5

<400> SEQUENCE: 58
ggggaccact ttgtacaaga aagctgggtt cagccgctgc ccaccgcgg                49

<210> SEQ ID NO 59
<211> LENGTH: 265
<212> TYPE: DNA
<213> ORGANISM: Oryza sativa

<400> SEQUENCE: 59
gtgattgatg agccctagaa ttcctccgcg gctcgagtgc tcgatcgccc gcttccatct     60
cttgctgaat gatgcggctt gggatgtggt ggttttgcag gtttgcacgc aggcaggcga    120
ggatcacgac gaggagagct ccgtcggcga ctccggctgg ggccgcgaga ggtgatcgag    180
ctcctctcca cgcgttcttg cttgtccttg acatgattaa ttacaaccgc cgttctctca    240
attgaattat cgcaattcaa tccag                                          265
```